US010888593B2

(12) United States Patent
Liles et al.

(10) Patent No.: US 10,888,593 B2
(45) Date of Patent: Jan. 12, 2021

(54) USE OF PECTIN OR PECTIN-RELATED SACCHARIDES TO ENHANCE EFFICACY OF PLANT GROWTH-PROMOTING RHIZOBACTERIA (PGPR) STRAINS FOR PROMOTING GROWTH AND HEALTH IN PLANTS AND ANIMALS

(71) Applicant: Auburn University, Auburn, AL (US)

(72) Inventors: Mark R. Liles, Auburn, AL (US); Joseph Kloepper, Auburn, AL (US)

(73) Assignee: AUBURN UNIVERSITY, Auburn, AL (US)

( * ) Notice: Subject to any disclaimer, the term of this patent is extended or adjusted under 35 U.S.C. 154(b) by 0 days.

(21) Appl. No.: 15/473,975

(22) Filed: Mar. 30, 2017

(65) Prior Publication Data

US 2017/0202888 A1 Jul. 20, 2017

Related U.S. Application Data

(63) Continuation-in-part of application No. PCT/US2015/053239, filed on Sep. 30, 2015.

(60) Provisional application No. 62/057,667, filed on Sep. 30, 2014.

(51) Int. Cl.
| | |
|---|---|
| *A61K 35/742* | (2015.01) |
| *A01N 63/00* | (2020.01) |
| *A61K 35/74* | (2015.01) |
| *A61K 48/00* | (2006.01) |
| *A01H 3/00* | (2006.01) |
| *A61K 31/7004* | (2006.01) |
| *A61P 1/00* | (2006.01) |
| *A23K 20/163* | (2016.01) |
| *A23K 50/80* | (2016.01) |
| *A23K 10/18* | (2016.01) |
| *A61K 31/732* | (2006.01) |

(52) U.S. Cl.
CPC ............. *A61K 35/742* (2013.01); *A01H 3/00* (2013.01); *A01N 63/00* (2013.01); *A23K 10/18* (2016.05); *A23K 20/163* (2016.05); *A23K 50/80* (2016.05); *A61K 31/7004* (2013.01); *A61K 31/732* (2013.01); *A61K 35/74* (2013.01); *A61K 48/00* (2013.01); *A61P 1/00* (2018.01)

(58) Field of Classification Search
CPC .... A01N 63/00; A01N 63/04; A61K 2300/00; A61K 35/742; A61K 35/74
See application file for complete search history.

(56) References Cited

U.S. PATENT DOCUMENTS

| | | | | |
|---|---|---|---|---|
| 5,472,952 A | * | 12/1995 | Smidt | C08B 37/0045 424/600 |
| 6,133,196 A | * | 10/2000 | Ocamb | A01N 63/00 504/100 |
| 6,524,998 B1 | | 2/2003 | Kloepper | |
| 6,884,754 B1 | * | 4/2005 | Schlatter | A01N 25/02 504/100 |
| 8,404,476 B2 | * | 3/2013 | Fernandez Martinez | A01N 63/00 435/252.5 |
| 8,445,255 B2 | | 5/2013 | Kloepper | |
| 9,205,116 B2 | | 12/2015 | Terhune | |
| 9,282,745 B2 | | 3/2016 | Kloepper | |

FOREIGN PATENT DOCUMENTS

CA 2869036 A1 * 10/2013 ............... C12R 1/07

OTHER PUBLICATIONS

Adesemoye AO, Torbert HA, & Kloepper JW (2009) Plant Growth-Promoting Rhizobacteria Allow Reduced Application Rates of Chemical Fertilizers. Microbial Ecology 58(4):921-929.
Aphis. (2003) Off-flavor in U.S. catfish operations. USDA: Animal and Plant Health Inspection Service. Veterinary Services.
Askelson, T.E., Campasino, A., Lee, J.T., Duong, T. (2014) Evaluation of phytate-degrading Lactobacillus culture administration to broiler chickens. Appl. Environ. Microbiol., 80, 943-950.
Balcazar, J.L., de Blas, I., Ruiz-Zarzuela, I., Cunningham, D., Vendrell, D. and Muzquiz, J.L. (2006) The role of probiotics in aquaculture. Vet Microbiol 114, 173-186.
Benson D.A., Karsch-Mizrachi I., Lipman D.J., Ostell J., Sayers E.W. (2009) GenBank. Nucleic Acids Res. Jan. 2009;37(Database issue):D26-31. Epub Oct. 21, 2008.
Bower, C.E., Holm-Hansen, T., (1980) A Salicylate-hypochlorite Method for Determining Ammonia in Seawater. Can. J. Fish. Aquat. Sci. 37, 794-798.
Cao, L., Wang, W., Yang, C., Yang, Y., Diana, J., Yakupitiyage, A., Luo, Z., Li, D. (2007) Application of microbial phytase in fish feed. Enzyme and Microbial Technology: 40: 4.
Caporaso J.G., Bittinger K., Bushman F.D., DeSantis T.Z., Andersen G.L., Knight R. (2010) PyNAST: a flexible tool for aligning sequences to a template alignment. Bioinformatics 26:266-267.
Caporaso J.G., et al, QIIME allows analysis of high-throughput community sequencing data. Nature Methods (2010) 7(5): 335-336.
Casula G., Cutting S.M. (2002) Bacillus probiotics: spore germination in the gastrointestinal tract. Appl Environ Microbiol 68: 2344-2352.
Cole, J. R., Chai, B., Marsh, T. L, Farris, R. J., Wang, Q., Kulam, S. A., Tiedje, J. M. (2003) The Ribosomal Database Project (RDP-II): previewing a new autoaligner that allows regular updates and the new prokaryotic taxonomy. Nucleic Acids Research, 31(1), 442-443.
DeSantis T.Z., Hugenholtz P., Larsen N., Rojas M., Brodie E.L., Keller K., et al. (2006) Greengenes, a chimera-checked 16S rRNA gene database and workbench compatible with ARB. Appl Environ Microb 72(7): 5069-5072.

(Continued)

*Primary Examiner* — Johann R Richter
(74) *Attorney, Agent, or Firm* — Quarles & Brady LLP

(57) ABSTRACT

Disclosed are compositions and methods that include or utilize plant growth promoting rhizobacteria (PGPR) for improving growth and health in plants and animals. The compositions and methods include or utilize a plant growth promoting rhizobacteria (PGPR) that expresses a protein associated with pectin metabolism, and a saccharide comprising pectin or a pectin-related saccharide.

11 Claims, 4 Drawing Sheets

Specification includes a Sequence Listing.

(56) References Cited

OTHER PUBLICATIONS

Diana, J. S. (2009) Aquaculture and biodiversity conservation. Bioscience, 59(1): 27-38.
Edgar R.C. (2010) Search and clustering orders of magnitude faster than BLAST. Bioinformatics 26(19):2460-2461.
FDA (2011) Aquaculture Drugs. In Fish and Fishery Products Hazards and Controls Guide ed. U. S. Department of Health and Human Services pp. 183-207. Washington, DC: FDA, Center for Food Safety and Applied Nutrition, Office of Food Safety.
Garcia, S. M., Rosenberg, A. A. (2010) Food security and marine capture fisheries: characteristics, trends, drivers and future perspectives. Phil. Trans. R. Soc. B 2010 365 2869-2880; DOI: 10.1098/rstb.2010.0171.
Gross, A., Boyd, C.E., Seo, J. (1999) Evaluation of the ultraviolet spectrophotometric method for the measurement of total nitrogen in water. Journal of the World Aquaculture Society 30:388-393.
Hong H.A., Duc L.H., Cutting S.M. (2005) The use of bacterial spore formers as probiotics. FEMS Microbiol Rev 29: 813-835.
Hossain MJ, et al., Implication of Lateral Genetic Transfer in the Emergence of Aeromonas hydrophila Isolates of Epidemic Outbreaks in Channel Catfish (2013) PLoS One 8.
Hossain MJ, et al., Deciphering the conserved genetic loci implicated in plant disease control through comparative genomics of *Bacillus amyloliquefaciens* subsp plantarum (2015) Front Plant Sci 6.
Hyronimus B., Le Marrec C., Hadji Sassi A., Deschamps A. (2000) Acid and bile tolerance of spore-forming lactic acid bacteria. Int J Food Microbiol 61: 193-197.
Kumar, V., Sinha, A.K., Makkar, H.P.S., Boeck, G.D., Becker, K. (2012) Phytate and phytase in fish nutrition. J. Anim. Physiol. Anim. Nutr., 96,335-364.
Lazzari, R., Baldisserotto, B. (2008) Nitrogen and phosphorous waste in fish farming. B. Inst. Pesca, São Paulo, 34(4): 591-600.
Le, P.T.T., Boyd, C.E. (2012) Comparison of Phenate and Salicylate Methods for Determination of Total Ammonia Nitrogen in Freshwater and Saline Water. J. World Aquacult. Soc. 43, 885-889.
Li, M. H., Robinson, E. H. (2008) Feeding catfish in commercial ponds. SRAC, 181.
Macfarlane, G. T., & Cummings, J. H. (1999). Probiotics and prebiotics: can regulating the activities of intestinal bacteria benefit health? BMJ☐: British Medical Journal, 318(7189), 999-1003.
Merino, G., Barange, M., Blanchard, J. L. et al. (2012) Can marine fisheries and aquaculture meet fish demand from a growing human population in a changing climate? Global Environmental Change 22, 795-806.
Naylor, R. L., Hardy, R. W., Bureau, A.C. et al. (2009) Feeding aquaculture in an era of finite resources. PNAS, 106(36), 15103-15110.
Ran, C., Carrias A., Williams M.A., Capps N., Dan B.C.T., Newton, J.C., Kloepper, J.W., Ooi, E.L., Browdy, C.L., Terhune, J.S., Liles, M.R. (2012) Identification of Bacillus Strains for Biological Control of Catfish Pathogens. PLoS ONE 7(9): e45793. doi:10.1371/journal.pone.0045793.
Rasmussen-Ivey, C., Hossain, M.J., Odom, S. E., Terhune, J.S., Hemstreet, W.G., Shoemaker, C.A., Zhang, D., Xu, D., Griffin, M.J., Liu, Y., Figueras, M.J., Santos, S.R., Newton, J.C. and Liles, M.R. Classification of a hypervirulent Aeromonas hydrophila pathotype responsible for epidemic outbreaks in warm-water fishes. Accepted for publication in Frontiers in Microbiology.
Rodgers, J. H. (2008) Algal Toxins in Pond Aquaculture. SRAC. 4605.
Sales, J. (2009) The effect of fish meal replacement by soyabean products on fish growth: a meta-analysis. Brit J Nutr 102: 1709-1722.
Sayers E.W., et al., (2009) Database resources of the National Center for Biotechnology Information. Nucleic Acids Res. Jan. 2009;37(Database issue):D5-15. Epub Oct. 21, 2008.
Schisler, D.A., et al., "Formulation of *Bacillus* spp. for Biological Control of Plant Diseases", NCAUR, vol. 94, No. 11, 2004, pp. 1267-1271.
Shaw, G. R., Moore, D., Garnett, C. M. (2003) Eutrophication and algal blooms. In Aleksandar Sabljic (Ed.), Encyclopedia of Life Support Systems (EOLSS) (pp. 1-21) Oxford, UK: Eolss Publishers.
Storebakken, T., Shearer, K D., Roem, A. J. (1998) Availability of protein, phosphorus and other elements in fish meal, soy-protein concentrate and phytase-treated soy-protein-concentrate-based diets to Atlantic salmon, Salmo salar. Aquacultue: 161: 1-4.
Summerfelt, Robert C., "Water Quality Considerations for Aquaculture", Dept. of Animal Ecology, Iowa State University.
Tucker, C. S., Ploeg, M. (1999) Managing off-flavor problems in pond-raised catfish. SRAC. 192.
US Department of Agriculture, USDA (2003) Part I: Reference of Fingerling Catfish Health and Production Practices in the United States. Fort Collins, CO, USA: National Health Monitoring System.
US Department of Agriculture, USDA (2003) Part II: Reference of Foodsize Catfish Health and Production Practices in the United States. Fort Collins, CO, USA: National Health Monitoring System.
Wang Y.B., Li J.R., Lin J. (2008) Probiotics in aquaculture: challenges and outlook. Aquaculture 281: 1-4.
Zhu, Y., X. Qiu, Q. Ding, M. Duan and C. Wang, 2014. Combined effects of dietary phytase and organic acid on growth and phosphorus utilization of juvenile yellow catfish Pelteobagrus fulvidraco. Aquaculture. 430: 1-8.
International Search Report and Written Opinion for PCT/US2015/053239 dated Jan. 13, 2016.
International Preliminary Report on Patentability for PCT/US2015/053239 dated Apr. 4, 2017.
Dunlap, christopher, et al., "Bacillus velezensis is not a later heterotypic synonym of Bacillus amyloliquefaciens; Bacillus methylotrophicus, *Bacillus amyloliquefaciens* subsp. plantarum and 'Bacillus oryzicola' are later heterotypic synonyms of Bacillus velezensis based on phylogenomics", Int. J. Systematic and Evolutionary Microbiology, 2016, 66, 1212-1217.
Brazil Instituto Nacional Da Propriedade Industrial, Office Action for application BR112017006629-7, dated Aug. 23, 2020. With translation.
He P. et al, "Genome sequence of the plant growth promoting strainBacillus amyloliquefacienssubsp. plantarumB9601-Y2 and expression of mersacidin and other secondary metabolites", Journal of Biotechnology, Elsevier Science Publishers, Amsterdam, NL, (2013), vol. 164, No. 2, doi:10.1016/J. JBIOTEC.2012.12.014, ISSN 0168-1656, pp. 281-291.
Niazi a. et al, "Genome Analysis of Bacillus amyloliquefaciens Subsp. plantarum UCMB5113: A Rhizobacterium That Improves Plant Growth and Stress Management", PLOS ONE, (2014), vol. 9, No. 8, doi:10.1371/journal.pone.0104651, p. e104651.
Wu K., et al, "Pectin Enhances Bio-Control Efficacy by Inducing Colonization and Secretion of Secondary Metabolites by Bacillus amyloliquefaciens SQY 162 in the Rhizosphere of Tobacco", PLOS ONE, (2015), vol. 10, No. 5, doi:10.1371/journal.pone.0127418, p. e0127418,.
Yegorenkova IV et al, "Composition and immunochemical characteristics of exopolysaccharides from the rhizobacterium Paenibacillus polymyxa 1465", Microbiology, US, (2008), vol. 77, No. 5, doi:10.1134/S002626170805007X, ISSN 0026-2617, pp. 553-558.

* cited by examiner

USE OF PECTIN OR PECTIN-RELATED SACCHARIDES TO ENHANCE EFFICACY OF PLANT GROWTH-PROMOTING RHIZOBACTERIA (PGPR) STRAINS FOR PROMOTING GROWTH AND HEALTH IN PLANTS AND ANIMALS

CROSS-REFERENCE TO RELATED APPLICATIONS

The present application is a continuation-in-part (CIP) under 35 U.S.C. § 365(c) of International Application No. PCT/US2015/053239, filed on Sep. 30, 2015, which international application claims the benefit of priority under 35 U.S.C. § 119(e) to U.S. provisional application No. 62/057,667, filed on Sep. 30, 2015, the content of which applications are incorporated herein by reference in their entireties.

FIELD

The presently disclosed subject matter relates to the field of plant growth-promoting rhizobacteria (PGPR). In particular, the present subject matter relates to the use of pectin or pectin-related saccharide to enhance the efficacy of PGPR in regard to promoting growth and health in plants and animals.

BACKGROUND

Plant-associated microorganisms have been extensively examined for their roles in natural and induced suppressiveness of soilborne diseases. Among the many groups of such organisms are root-associated bacteria, which generally represent a subset of soil bacteria. Rhizobacteria are a subset of total rhizosphere bacteria which have the capacity, upon re-introduction to seeds or vegetative plant parts (such as potato seed pieces), to colonize the developing root system in the presence of competing soil microflora. Root colonization is typically examined by quantifying bacterial populations on root surfaces; however, some rhizobacteria can also enter roots and establish at least a limited endophytic phase. Hence, root colonization may be viewed as a continuum from the rhizosphere to the rhizoplane to internal tissues of roots.

Rhizobacteria which exert a beneficial effect on the plant being colonized are termed "plant-growth promoting rhizobacteria" or "PGPR." PGPR may benefit the host by causing plant growth promotion or biological disease control. The same strain of PGPR may cause both growth promotion and biological control. Among the soilborne pathogens shown to be negatively affected by PGPR are *Aphanomyces* spp., i Fusarium oxysporum, Gaeumannomyces graminis, Phytophthora spp., *Pythium* spp., *Rhizoctonia solani, Sclerotium rolfsii, Thielaviopsis basicola*, and *Verticillium* spp. In most of these cases, biological control results from bacterial production of metabolites which directly inhibit the pathogen, such as antibiotics, hydrogen cyanide, iron-chelating siderophores, and cell wall-degrading enzymes. Plant growth promotion by PGPR may also be an indirect mechanism of biological control, leading to a reduction in the probability of a plant contracting a disease when the growth promotion results in shortening the time that a plant is in a susceptible state, e.g. in the case where PGPR cause enhanced seedling emergence rate, thereby reducing the susceptible time for pre-emergence damping-off. An alternative mechanism for biological control by PGPR is induced systemic resistance. PGPR and uses thereof are disclosed in the prior art. (See, e.g., U.S. Pat. Nos. 8,445,255; 6,524,998; 5,935,839; 5,640,803; 5,503,652; and 5,503,651; the contents of which are incorporated herein by reference in their entirety).

In addition to their observed association in nature with plants, PGPR also may be utilized as probiotics for animals in order to improve animal growth or animal health. For example, *Bacillus amyloliquefaciens* subsp. *plantarum* (now *Bacillus velezensis*) AP193 has been described as a probiotic for fish. (See U.S. Published Application No. 2012/0328572).

In swine, probiotics have been used to have a positive influence on gut microbiota balance, intestinal epithelium integrity and maturation of gut-associated tissue. (See Corcionivoshi et al., Animal Science and Biotechnologies, 2010, 43(1)). In poultry, probiotics have been used to maintain digestive microbial balance and to reduce potential pathogenic bacteria which results in improving growth, egg production, and feed conversion. (See id.). In cattle, probiotics have been used to prevent and combat digestive disorders such as diarrhea during lactation, to influence ruminal metabolism of nutrients, which helps maintain health and improve productive performance. (See id.). In sheep, probiotics have been used to prevent and combat pathological conditions that arise from digestive balance. (See id.).

Therefore, new compositions and methods of use for PGPR in promoting growth and health in plants and animals are desirable.

SUMMARY

Disclosed are compositions and methods that include or utilize plant growth promoting rhizobacteria (PGPR) for improving growth and health in plants and animals. The compositions and methods include or utilize a plant growth promoting rhizobacteria (PGPR) that expresses a protein associated with pectin metabolism, and a saccharide comprising pectin or a pectin-related saccharide.

The disclosed compositions may include inoculants which comprise: (a) a plant growth promoting rhizobacteria (PGPR) that expresses a protein associated with pectin metabolism; and (b) a saccharide comprising pectin or a pectin-related saccharide. Suitable PGPR may include *Bacillus* species such as *Bacillus amyloliquefaciens* subspecies *plantarum* (now *Bacillus velezensis*). The pectin or pectin-related saccharides may include pectin-derived saccharides such as hydrolyzed pectin, D-galacturonate, D-glucuronate, or mixtures thereof. Optionally, the pectin or pectin-related saccharide functions as a carrier for the PGPR and/or the inoculant includes a carrier other than the pectin or pectin-related saccharide.

The disclosed compositions may be used to treat plants, seeds, and soils in order to improve plant growth or plant health. The disclosed compositions may be formulated as a plant treatment composition, a coating for seeds, or a soil amendment composition.

The disclosed compositions also may be administered to animals in order to improve animal growth or animal health. The disclosed compositions may be formulated as an animal feed, such as a pelleted animal feed.

Also disclosed are methods of using pectin or pectin-related saccharides and PGPR in regard to promoting growth or health in plants and animals. The disclosed methods for improving plant growth or plant health may include: (a) treating plants, seeds, or soil with a plant growth promoting rhizobacteria (PGPR) that expresses a protein associated with pectin metabolism and (b) treating the plants, seeds, or soil with a saccharide comprising pectin or a pectin-related saccharide, where the plants, seeds, or soil may be treated with the PGPR and the saccharide concurrently or are treated with the PGPR and saccharide non-currently in either order.

The disclosed methods for improving animal growth or animal health may include (a) administering to an animal a plant growth promoting rhizobacteria (PGPR) that expresses a protein associated with pectin metabolism and (b) administering to the animal a saccharide comprising pectin or a pectin-related saccharide, where the animals may be administered the PGPR and the saccharide concurrently or are treated with the PGPR and saccharide non-currently in either order.

Also disclosed are methods of using pectin or pectin-related saccharides and PGPR in regard to promoting and/or increasing nodulation in nitrogen-fixing plants such as nitrogen-fixing legumes. The disclosed methods for promoting and/or increasing nodulation in a legume may include: (a) treating the legume, seeds of the legume, or soil surrounding the legume with a plant growth promoting rhizobacteria (PGPR) that expresses a protein associated with pectin metabolism and (b) treating the legume, seeds of the legume, or soil surrounding the legume with a saccharide comprising pectin or a pectin-related saccharide, where the legume, seeds of the legume, or soil surrounding the legume may be treated with the PGPR and the saccharide concurrently or the legume, seeds of the legume, or soil surrounding the legume are treated with the PGPR and saccharide non-currently in either order.

Also disclosed are methods of using pectin or pectin-related saccharides to prepare compositions and inoculants as disclosed herein. The methods may include combining PGPR and pectin, which has been extracted from pectin-containing plant material, or pectin-related saccharides to prepare the disclosed compositions and inoculants. Optionally, a carrier may be combined with the PGPR and pectin or pectin-related saccharides to prepare the disclosed compositions and inoculants.

DETAILED DESCRIPTION

Figure 1:
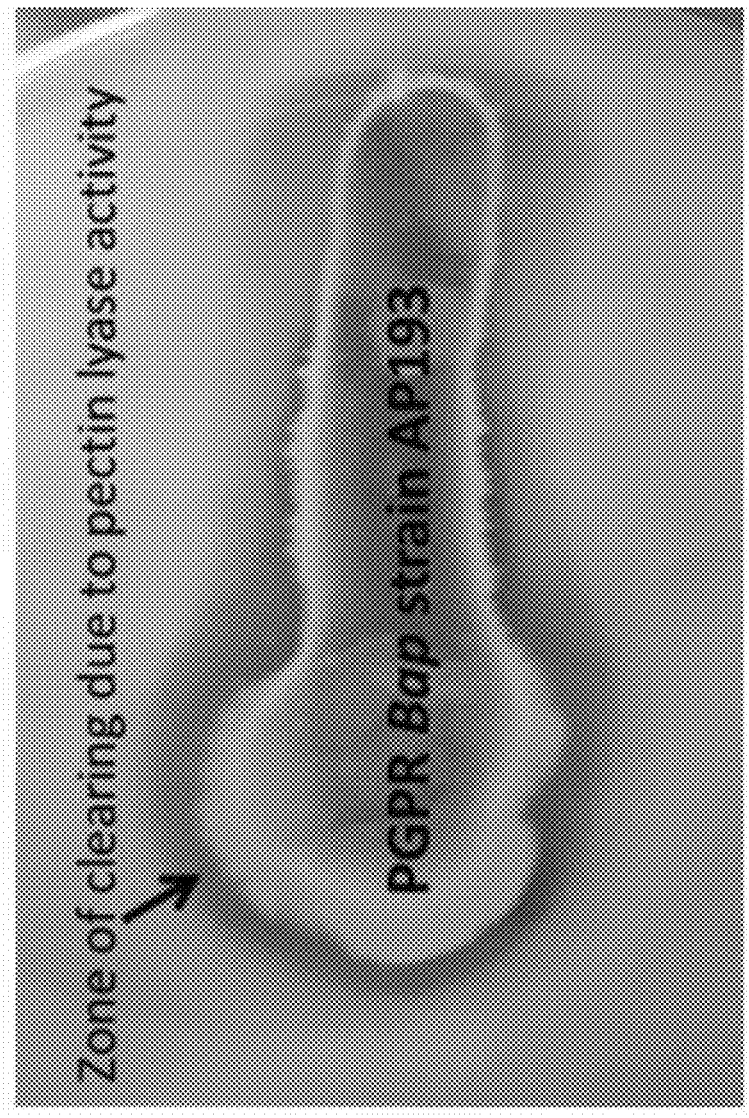
FIG. 1. Expression of a pectin lyase activity by PGPR Bap (now Bv) strain AP193. Note the cleared halo around the growth of the Bap (now Bv) strain due to pectin degradation.

The disclosed subject matter of the invention may be described using various terms as described below.

Unless otherwise specified or indicated by context, the terms "a", "an", and "the" mean "one or more." For example, "a sugar" should be interpreted to mean "one or more sugars" unless otherwise specified or indicated by context.

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≤10% of the particular term and "substantially" and "significantly" will mean plus or minus >10% of the particular term.

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and allowing the inclusion only of additional components that do not fundamentally alter the nature of the claimed subject matter.

The term "plant" as utilized herein should be interpreted broadly and may include angiosperms and gymnosperms, dicots and monocots, and trees. Examples of angiosperm dicots may include, but are not limited to tomato, tobacco, cotton, rapeseed, field beans, soybeans, peppers, lettuce, peas, alfalfa, clover, cabbage, broccoli, cauliflower, brussel sprouts), radish, carrot, beets, eggplant, spinach, cucumber, squash, melons, cantaloupe, and sunflowers. Example of angiosperm monocots may include, but are not limited to asparagus, field and sweet corn, barley, wheat, rice, sorghum, onion, pearl millet, rye, oats, and sugar cane. Woody plants may include, but are not limited to fruit trees, acacia, alder, aspen, beech, birch, sweet gum, sycamore, poplar, willow, fir, pine, spruce, larch, cedar, and hemlock.

The term "plant" may include nitrogen-fixing plants such as nitrogen-fixing legumes. As is understood in the art, a "legume" is a plant belonging to the family Facaceae or Leguminosae. Most legumes have root nodules comprising symbiotic nitrogen-fixing bacteria. The symbiotic nitrogen-fixing bacteria of root nodules are capable of taking atmospheric nitrogen ($N_2$) and reducing the atmospheric $N_2$ to ammonia via the reaction: $N_2 + 8H^+ + 8e^- \rightarrow 2NH_3 + H_2$. The ammonia thus produced can be further reduced to ammonium by the following reaction: $NH_3 + H^+ \rightarrow NH_4^+$. The ammonium thus produced can be used by the legume as a nitrogen source for growth. As such, root nodules and the symbiotic nitrogen-fixing bacteria therewithin are important for plant growth and methods and compositions that promote and/or increase nodulation are desirable.

The term "animal" as utilized herein should be interpreted broadly and may include mammals and non-mammals.

Mammals may include human and non-human mammals, such as cows, pigs, sheep, and the like. Non-mammals may include birds (e.g., chickens, turkeys, ducks, and the like) and fish.

Non-human animals may include aquatic animals. In particular, aquatic animals may include farmed fish (e.g. catfish or tilapia) and crustaceans (e.g., shrimp).

The present inventors have identified a collection of plant growth-promoting rhizobacteria (PGPR) that are capable of improving the growth of plants, and also have disease- and pest-controlling activity. From an analysis of genome sequences from the best-performing *Bacillus amyloliquefaciens* subspecies *plantarum* (now *Bacillus velezensis*) PGPR strains, the inventors identified some genetically encoded functions that are always present within these *Bacillus* PGPR strains and are not present in other *Bacillus* species that are not plant-related. In particular, these PGPR strains can use sugars derived from plant pectin as a carbon and/or energy source. By supplementing pectin on plant seeds that are inoculated with *Bacillus* spores, or by supplementing the amount of pectin available for *Bacillus* PGPR strain post-seed germination, this will result in an enhancement of 1) the *Bacillus* strain colonization of the plant rhizosphere and/or 2) better persistence of *Bacillus* within the plant rhizosphere and/or 3) better plant growth performance in response to PGPR strain+pectin administration and/or 4) better biological control of disease (e.g., bacteria, fungi, viruses) or pests (e.g., nematodes) as a result of PGPR strain+pectin administration.

PGPR

The term "plant growth promoting rhizobacteria" or "PGPR" refers to a group of bacteria that colonize plant roots, and in doing so, promote plant growth and/or reduce disease or damage from predators. Bacteria that are PGPR may belong to genera including, but not limited to *Actinobacter, Alcaligenes, Bacillus, Burkholderia, Buttiauxella, Enterobacter, Klebsiella, Kluyvera, Pseudomonas, Rahnella, Ralstonia, Rhizobium, Serratia, Stenotrophomonas, Paenibacillus*, and *Lysinibacillus*. The PGPR utilized in the disclosed methods and composition may be a single strain, species, or genus of bacteria or may comprise a mixture of bacterial strains, species, or genera. For example, the PGPR may be selected from genera including, but not limited to, *Actinobacter, Alcaligenes, Bacillus, Burkholderia, Buttiauxella, Enterobacter, Klebsiella, Kluyvera, Pseudomonas, Rahnella, Ralstonia, Rhizobium, Serratia, Stenotrophomonas, Paenibacillus*, and *Lysinibacillus*.

The genus *Bacillus* as used herein refers to a genus of Gram-positive, rod-shaped bacteria which are members of the division Firmicutes. Under stressful environmental conditions, the *Bacillus* bacteria produce oval endospores that can stay dormant for extended periods. *Bacillus* bacteria may be characterized and identified based on the nucleotide sequence of their 16S rRNA or a fragment thereof (e.g., approximately a 1000 nt, 1100 nt, 1200 nt, 1300 nt, 1400 nt, or 1500 nt fragment of 16S rRNA or rDNA nucleotide sequence). *Bacillus* bacteria may include, but are not limited to *B. acidiceler, B. acidicola, B. acidiproducens, B. aeolius, B. aerius, B. aerophilus, B. agaradhaerens, B. aidingensis, B. akibai, B. alcalophilus, B. algicola, B. alkalinitrilicus, B. alkalisediminis, B. alkalitelluris, B. altitudinis, B. alveayuensis, B. amyloliquefaciens, B. anthracis, B. aquimaris, B. arsenicus, B. aryabhattai, B. asahii, B. atrophaeus, B. aurantiacus, B. azotoformans, B. badius, B. barbaricus, B. bataviensis, B. beijingensis, B. benzoevorans, B. beveridgei, B. bogoriensis, B. boroniphilus, B. butanolivorans, B. canaveralius, B. carboniphilus, B. cecembensis, B. cellulosilyticus, B. cereus, B. chagannorensis, B. chungangensis, B. cibi, B. circulans, B. clarkii, B. clausii, B. coagulans, B. coahuilensis, B. cohnii, B. decisifrondis, B. decolorationis, B. drentensis, B. farraginis, B. fastidiosus, B. firmus, B. flexus, B. foraminis, B. fordii, B. fortis, B. fumarioli, B. funiculus, B. galactosidilyticus, B. galliciensis, B. gelatini, B. gibsonii, B. ginsengi, B. ginsengihumi, B. graminis, B. halmapalus, B. halochares, B. halodurans, B. hemicellulosilyticus, B. herbertsteinensis, B. horikoshi, B. horneckiae, B. horti, B. humi, B. hwajinpoensis, B. idriensis, B. indicus, B. infantis, B. infernus, B. isabeliae, B. isronensis, B. jeotgali, B. koreensis, B. korlensis, B. kribbensis, B. krulwichiae, B. lehensis, B. lentus, B. licheniformis, B. litoralis, B. locisalis, B. luciferensis, B. luteolus, B. macauensis, B. macyae, B. mannanilyticus, B. marisflavi, B. marmarensis, B. massiliensis, B. megaterium, B. methanolicus, B. methylotrophicus, B. mojavensis, B. muralis, B. murimartini, B. mycoides, B. nanhaiensis, B. nanhaiisediminis, B. nealsonii, B. neizhouensis, B. niabensis, B. niacini, B. novalis, B. oceanisediminis, B. odysseyi, B. okhensis, B. okuhidensis, B. oleronius, B. oshimensis, B. panaciterrae, B. patagoniensis, B. persepolensis, B. plakortidis, B. pocheonensis, B. polygoni, B. pseudoalcaliphilus, B. pseudofirmus, B. pseudomycoides, B. psychrosaccharolyticus, B. pumilus, B. qingdaonensis, B. rigui, B. runs, B. safensis, B. salarius, B. saliphilus, B. schlegelii, B. selenatarsenatis, B. selenitireducens, B. seohaeanensis, B. shackletonii, B. siamensis, B. simplex, B. siralis, B. smithii, B. soli, B. solisalsi, B. sonorensis, B. sporothermodurans, B. stratosphericus, B. subterraneus, B. subtilis, B. taeansis, B. tequilensis, B. thermantarcticus, B. thermoamylovorans, B. thermocloacae, B. thermolactis, B. thioparans, B. thuringiensis, B. tripoxylicola, B. tusciae, B. vallismortis, B. vedderi, B. vietnamensis, B. vireti, B. wakoensis, B. weihenstephanensis, B. xiaoxiensis*, and mixtures or blends thereof.

The PGPR and inoculants thereof disclosed herein may include *B. amyloliquefaciens* or a *Bacillus* species that is closely related to *B. amyloliquefaciens*. A *Bacillus* species that is closely related to *B. amyloliquefaciens* may be defined as a species having a 16S rDNA sequence comprising SEQ ID NO:26 or comprising a 16S rDNA sequence having at least about 98% or 99% sequence identity to SEQ ID NO:26. The PGPR preferably is *B. amyloliquefaciens* subspecies *plantarum* (now *B. velezensis*) or a *Bacillus* species that is closely related to *B. amyloliquefaciens* subspecies *plantarum* (now *B. velezensis*). *B. amyloliquefaciens* subspecies *plantarum* (now *B. velezensis*) is a subspecies of *B. amyloliquefaciens* which is colonizes plant roots and typically exhibits amylase activity. Suitable PGPR strains for the disclosed methods and compositions may include PGPR strains having a gyrB gene that exhibits sequence identity to the gyrB gene from strains of *Bacillus amyloliquefaciens* subspecies *plantarum* (now *Bacillus velezensis*). In some embodiment, the PGPR strain utilized in the disclosed methods and compositions has at gyrB gene having at least about 80%, 90%, 95%, 96%, 97%, 98%, 99% or 100% sequence identity to the polynucleotide sequence of SEQ ID NO:25, which is the polynucleotide sequence of the gyrB gene from strains of *Bacillus amyloliquefaciens* subsp. *plantarum* (now *Bacillus velezensis*).

Suitable strains of *B. amlyoliquefaciens* subsp. *plantarum* (*B. velezensis*) for use in the disclosed compositions and methods may include but are not limited to *Bacillus amyloliquefaciens* subsp. *plantarum* (now *Bacillus velezensis*) AS43.3, *Bacillus amyloliquefaciens* subsp. *plantarum* (now *Bacillus velezensis*) TrigoCor1448, *Bacillus amyloliquefaciens* subsp. *plantarum* (now *Bacillus velezensis*)

UCMB5033, *Bacillus amyloliquefaciens* subsp. *plantarum* (now *Bacillus velezensis*) UCMB5113, *Bacillus amyloliquefaciens* subsp. *plantarum* (now *Bacillus velezensis*) EBL11, *Bacillus amyloliquefaciens* subsp. *plantarum* (now *Bacillus velezensis*) W2, *Bacillus amyloliquefaciens* subsp. *plantarum* (now *Bacillus velezensis*) UCMB5036, *Bacillus amyloliquefaciens* subsp. *plantarum* (now *Bacillus velezensis*) IT-45, *Bacillus amyloliquefaciens* subsp. *plantarum* (now *Bacillus velezensis*) UASWS BA1, *Bacillus amyloliquefaciens* subsp. *plantarum* (now *Bacillus velezensis*) LFB 112, *Bacillus amyloliquefaciens* subsp. *plantarum* (now *Bacillus velezensis*) CAUB946, *Bacillus amyloliquefaciens* subsp. *plantarum* (now *Bacillus velezensis*) M27, *Bacillus amyloliquefaciens* subsp. *plantarum* (now *Bacillus velezensis*) B1895, *Bacillus amyloliquefaciens* subsp. *plantarum* (now *Bacillus velezensis*) SQR9, *Bacillus amyloliquefaciens* subsp. *plantarum* (now *Bacillus velezensis*) AH159-1, *Bacillus amyloliquefaciens* subsp. *plantarum* (now *Bacillus velezensis*) DC-12, *Bacillus amyloliquefaciens* subsp. *plantarum* (now *Bacillus velezensis*) YAU B9601-Y2, *Bacillus amyloliquefaciens* subsp. *plantarum* (now *Bacillus velezensis*) Y2, *Bacillus amyloliquefaciens* subsp. *plantarum* (now *Bacillus velezensis*) EGD_AQ14, *Bacillus amyloliquefaciens* subsp. *plantarum* (now *Bacillus velezensis*) NAU-B3, *Bacillus amyloliquefaciens* subsp. *plantarum* (now *Bacillus velezensis*) FZB42, *Bacillus amyloliquefaciens* subsp. *plantarum* (now *Bacillus velezensis*) CC 178, *Bacillus amyloliquefaciens* subsp. *plantarum* (now *Bacillus velezensis*) AP79, *Bacillus amyloliquefaciens* subsp. *plantarum* (now *Bacillus velezensis*) AP71, *Bacillus amyloliquefaciens* subsp. *plantarum* (now *Bacillus velezensis*) AP143, *Bacillus amyloliquefaciens* subsp. *plantarum* (now *Bacillus velezensis*) AP193, *Bacillus amyloliquefaciens* subsp. *plantarum* (now *Bacillus velezensis*) AB01, and *Bacillus amyloliquefaciens* subsp. *plantarum* (now *Bacillus velezensis*) GB03.

Suitable PGPR strains and inoculants thereof for the methods and compositions disclosed herein may include PGPR strains that express one or more proteins associated with pectin metabolism. In some embodiments, the PGPR strain may express one or more proteins associated with pectin metabolism, which may include but are not limited to proteins encoded by a gene selected from the group consisting of uxaA (altronate dehydratase), uxaB (altronate oxidoreductase), uxaC (uronate isomerase), uxaA (mannonate dehydratase, uxuB (D-mannonate oxidoreductase), kdgA (4-hydroxy-2-oxoglutarate aldolase), kdgK (2-dehydro-3-deoxygluconokinase), exuR (hexuronate utilization operon transcriptional repressor), exuT (hexuronate transporter), and combinations thereof. In some embodiments, the PGPR strain may express one or more pectinase enzymes selected from a group consisting of pectin lyase, pectate lyase, polygalacturonase, and pectin esterase.

The uxaA gene encodes an enzyme which is an altronate dehydratase (EC:4.2.1.7) which converts D-altronate to 2-dehydro-3-deoxy-D-gluconate and water. Therefore, suitable PGPR strains and inoculants thereof for the methods and composition disclosed herein may include a PGPR strain that expresses altronate dehydratase. SEQ ID NO:1 provides the polynucleotide sequence encoding for altronate dehydratase. SEQ ID NO:2 provides the amino acid sequence for altronate dehydratase.

The uxaB gene encodes an enzyme which is an altronate oxidoreductase (EC:5.3.1.12) which converts D-altronate and NAD$^+$ to D-tagaturonate and NADH. Therefore, suitable PGPR strains and inoculants thereof for the methods and composition disclosed herein may include a PGPR strain that expresses altronate oxidoreductase. SEQ ID NO:3 provides the polynucleotide sequence encoding for altronate oxidoreductase. SEQ ID NO:4 provides the amino acid sequence for altronate oxidoreductase.

The uxaC gene encodes an enzyme which is an uronate isomerase (EC:1.3.1.12) which converts D-glucuronate to D-fructuronate and which converts D-galacturonate to D-tagaturonate. Therefore, suitable PGPR strains and inoculants thereof for the methods and composition disclosed herein may include a PGPR strain that expresses uronate isomerase. SEQ ID NO:5 provides the polynucleotide sequence encoding for altronate oxidoreductase. SEQ ID NO:6 provides the amino acid sequence for altronate oxidoreductase.

The uxuA gene encodes an enzyme which is a mannonate dehydratase (EC:4.2.1.8) which converts D-mannonate to 2-dehydro-3-deoxy-D-gluconate. Therefore, suitable PGPR strains and inoculants thereof for the methods and composition disclosed herein may include a PGPR strain that expresses mannonate dehydratase. SEQ ID NO:7 provides the polynucleotide sequence encoding for mannonate dehydratase. SEQ ID NO:8 provides the amino acid sequence for mannonate dehydratase.

The uxuB gene encodes an enzyme which is a D-mannonate oxidoreductase (EC:1.1.1.57) which converts D-mannonate and NAD$^+$ to D-fructuronate and NADH. Therefore, suitable PGPR strains and inoculants thereof for the methods and composition disclosed herein may include a PGPR strain that expresses D-mannonate oxidoreductase. SEQ ID NO:9 provides the polynucleotide sequence encoding for altronate oxidoreductase. SEQ ID NO:10 provides the amino acid sequence for altronate oxidoreductase.

The kdgA gene encodes an enzyme which is a 4-hydroxy-2-oxoglutarate aldolase (EC 4.1.3.16) which converts 4-hydroxy-2-oxoglutarate to pyruvate and glyoxylate, and which converts 2-dehydro-3-deoxy-6-phosphate-D-gluconate to pyruvate and D-glyceraldehyde 3-phosphate. Therefore, suitable PGPR strains and inoculants thereof for the methods and composition disclosed herein may include a PGPR strain that expresses 4-hydroxy-2-oxoglutarate aldolase. SEQ ID NO:11 provides the polynucleotide sequence encoding for 4-hydroxy-2-oxoglutarate aldolase. SEQ ID NO:12 provides the amino acid sequence for 4-hydroxy-2-oxoglutarate aldolase.

The kdgK gene encodes an enzyme which is 2-dehydro-3-deoxygluconokinase (EC 2.7.1.45) which phosphorylates 2-keto-3-deoxygluconate (KDG) to produce 2-keto-3-deoxy-6-phosphogluconate (KDPG). Therefore, suitable PGPR strains and inoculants thereof for the methods and composition disclosed herein may include a PGPR strain that expresses 2-dehydro-3-deoxygluconokinase. SEQ ID NO:13 provides the polynucleotide sequence encoding for 2-dehydro-3-deoxygluconokinase. SEQ ID NO:14 provides the amino acid sequence for 2-dehydro-3-deoxygluconokinase.

The exuR gene encodes a hexuronate utilization operon transcriptional repressor. Therefore, suitable PGPR strains and inoculants thereof for the methods and composition disclosed herein may include a PGPR strain that expresses a hexuronate utilization operon transcriptional repressor. SEQ ID NO:15 provides the polynucleotide sequence encoding for a hexuronate utilization operon transcriptional repressor. SEQ ID NO:16 provides the amino acid sequence for a hexuronate utilization operon transcriptional repressor.

The exuT gene encodes a hexuronate transporter which exhibits hexuronate transmembrane transporter activity. Therefore, suitable PGPR strains and inoculants thereof for the methods and composition disclosed herein may include a PGPR strain that expresses a hexuronate transporter. SEQ ID NO:17 provides the polynucleotide sequence encoding for a hexuronate transporter. SEQ ID NO:18 provides the amino acid sequence for a hexuronate transporter.

In some embodiments, the PGPR strain may express one or more pectinase enzymes selected from a group consisting of pectin lyase (EC 4.2.2.10), pectate lyase (EC 4.2.2.2), polygalacturonase (EC 3.2.1.15), and pectin esterase (EC 3.1.1.11). SEQ ID NO:19 provides the polynucleotide sequence encoding for a pectate lyase precursor. SEQ ID NO:20 provides the amino acid sequence for a pectate lyase precursor. SEQ ID NO:21 provides the polynucleotide sequence encoding for a pectin-lyase like protein. SEQ ID NO:22 provides the amino acid sequence for a pectin-lyase like protein. SEQ ID NO:23 provides the polynucleotide sequence encoding for a pectin lyase. SEQ ID NO:24 provides the amino acid sequence for a pectin lyase.

"Percentage sequence identity" may be determined by aligning two sequences of equivalent length using the Basic Local Alignment Search Tool (BLAST) available at the National Center for Biotechnology Information (NCBI) website (i.e., "bl2seq" as described in Tatiana A. Tatusova, Thomas L. Madden (1999), "Blast 2 sequences—a new tool for comparing protein and nucleotide sequences", FEMS Microbiol Lett. 174:247-250, incorporated herein by reference in its entirety). For example, percentage sequence identity between SEQ ID NO:1 and another sequence for comparison may be determined by aligning these two sequences using the online BLAST software provided at the NCBI website.

"Percentage sequence identity" between two deoxyribonucleotide sequences may also be determined using the Kimura 2-parameter distance model which corrects for multiple hits, taking into account transitional and transversional substitution rates, while assuming that the four nucleotide frequencies are the same and that rates of substitution do not vary among sites (Nei and Kumar, 2000) as implemented in the MEGA 4 (Tamura K, Dudley J, Nei M & Kumar S (2007) MEGA4: Molecular Evolutionary Genetics Analysis (MEGA) software version 4.0. *Molecular Biology and Evolution* 24:1596-1599), preferably version 4.0.2 or later. The gap opening and extension penalties are set to 15 and 6.66 respectively. Terminal gaps are not penalized. The delay divergent sequences switch is set to 30. The transition weight score is 35 set to 0.5, as a balance between a complete mismatch and a matched pair score. The DNA weight matrix used is the TUB scoring matrix where x's and n's are matches to any IUB ambiguity symbol, and all matches score 1.9, and all mismatched score O.

Pectin and Pectin-Related Saccharides

The disclosed compositions and methods include or utilize pectin or pectin-derived sugars in order to sugars to enhance the efficacy of PGPR in regard to promoting plant growth and plant health. "Pectin" is a heteropolysaccharide found natively in the primary cell walls of terrestrial plants having a typical molecular weight of 60,000-130,000 g/mol, which varies based on the origin of the pectin and the extraction conditions. As used herein, "pectin" is meant to include extracted pectin that has been extracted from its native condition (e.g., extracted pectin from primary cell walls of terrestrial plants).

The compositions and methods disclosed herein may comprise and/or utilize a relatively high molecular weight polysaccharide such as a relatively high molecular weight pectin. In some embodiments, the compositions and methods disclosed herein comprise and/or utilize pectin having an average molecular weight of at least about 1000, 2000, 5000, 10000, 15000, 20000, 25000, 30000, 35000, 40000, 45000, 50000, 55000, or 60000 g/mol. Is some embodiments, the relatively high molecular weight polysaccharide represents at least about 10%, 20%, 30%, 40%, 50%, 60%, 70%, 80%, 90%, 95%, or higher of the total amount of carbohydrate in a composition as contemplated herein.

The disclosed composition and methods may include and/or utilize pecting and/or pectin derived sugars in any form. In some embodiments, the pectin and/or pectin derivated sugars are in powder form. The powder form may be utilized to prepare a solution of the pectin and/or pectin derivated sugars. Solutions of pectin prepared for use in the presently disclosed methods may have a concentration (w/w) of about 0.0001%, 0.0005%, 0.001%, 0.005%, 0.01%, 0.05%, 0.1%, 0.5%, 1%, 2%, 3%, 4%, or 5%, or solutions of pectin prepared for use in the presently disclosed methods may have a concentration of pectin within a range bounded by any of these percentage values (e.g., within a range of 0.01%-1%). A solution thus prepared may be utilized in the methods disclosed herein, including methods for treating plants, increasing nodulation in legumes, and/or treating animals.

The pectin or pectin-related saccharides utilized in the disclosed composition and methods may be isolated or substantially purified. The terms "isolated" or "substantially purified" refers to pectin or pectin-related saccharides that have been removed from a natural environment and have been isolated or separated, and are at least 60% free, preferably at least 75% free, and more preferably at least 90% free, even more preferably at least 95% free, and most preferably at least 100% free from other components with which they were naturally associated, which other components may include but are not limited to cellulose or other non-pectin polysaccharides.

Although the composition of pectin may vary among plants, pectin typically has a composition in which D-galacturonic acid is the main monomeric constituent (i.e., typically D-galacturonic acid represents >50% of the monomeric constituents of pectin). The D-galacturonic residues of pectin optionally may be substituted with D-xylose or D-apiose to form xylogalacturonan and apiogalacturonan, respectively, branching from a D-galacturonic acid residue. So-called "rhamnogalcturonan pectins" contain a backbone of repeating disaccharides of D-galacturonic acid and L-rhamnose. Pectins and pectin-derived products suitable for use in the presently disclosed compositions and methods may include pectin in which D-galacturonic acid represents >50% of the monomeric constituents of the pectin, optionally where one or more of the D-galacturonic residues of pectin are substituted with D-xylose or D-apiose to form xylogalacturonan and apiogalacturonan, respectively, branching from a D-galacturonic acid residue. Pectins and pectin-derived products suitable for use in the presently disclosed compositions and methods may include so-called "rhamnogalcturonan pectins" that contain a backbone of repeating disaccharides of D-galacturonic acid and L-rhamnose.

In nature, the majority of carboxyl groups of galacturonic acid in pectin are esterified with methanol (i.e., >50% and as much as 80% of the carboxyl groups of galacturonic acid in pectin are esterified with methanol). During extraction, this percentage may decrease where extraction may result in hydrolysis of the ester bond, and extracted pectins may be categorized as high-ester versus low-ester pectins having <50% of galacturonic acid residues being esterified. Non-esterified galacturonic acid units can be either free acids (i.e., carboxyl groups) or salts with sodium, potassium, or calcium (i.e., galacturonate salts). Pectins and pectin-derived products suitable for use in the presently disclosed compositions and methods may include pectins in which the majority of carboxyl groups of galacturonic acid in pectin are esterified with methanol (i.e., >50% and as much as 80% of the carboxyl groups of galacturonic acid in pectin are esterified with methanol). After extraction, pectins and pectin-derived products suitable for use in the presently disclosed compositions and methods may include extracted pectins (e.g., high-ester pectins or low-ester pectins having <50% of galacturonic acid residues being esterified).

In nature, D-galacturonic acid may be synthesized from D-gluconoric acid derivatives (e.g., from UDP-D-glucuronate via 4-epimerization) and conversely, D-galacturonic acid in pectin may be metabolized to form D-gluconoric acid derivatives (e.g., 5-dehydro-4-deoxy-D-glucuronate via oligogalacturonate lysis). As used herein, pectin-related saccharides include pectin-derived saccharides such as hydrolyzed pectin, D-galacturonic acid (or D-galacturonate salts), and D-gluconoric acid (or D-gluconorate salts), polymers thereof, or combinations thereof.

The compositions and methods disclosed herein may include or utilize a saccharide that is a substrate for an enzyme or transporter encoded by a gene selected from the group consisting of uxaA (altronate dehydratase), uxaB (altronate oxidoreductase), uxaC (uronate isomerase), uxuA (mannonate dehydratase), uxuB (D-mannonate oxidoreductase), kdgA (4-hydroxy-2-oxoglutarate aldolase), kdgK (2-dehydro-3-deoxygluconokinase), exuR (hexuronate utilization operon transcriptional repressor), exuT (hexuronate transporter), and combinations thereof. The compositions and methods disclosed herein may include or utilize a saccharide that is a substrate for a pectinase enzyme (e.g., a pectinase enzyme selected from a group consisting of pectin lyase, pectate lyase, polygalacturonase, and pectin esterase).

Substrates as such may include but are not limited to saccharides derived from pectin such as D-galacturonate and D-glucuronate. The saccharide may comprise a mixture of sugars or the saccharide may comprise a heteropolysaccharide. In embodiments in which the saccharide is a heterogeneous mixture of sugars or the saccharide is a heteropolysaccharide, preferably D-galacturonate monomeric units, D-glucuronate monomeric units, or the sum of D-galacturonate monomeric units and D-glucuronate monomeric units represent >50%, >60%, >70%, >80%, >90%, or >95% of total monomeric units in the heterogeneous mixture of sugars or the heteropolysaccharide.

The disclosed pectin and pectin-related substances may include synthetic pectin. Synthetic pectin may include pectin synthesized by polymerizing pectin monomers (e.g., uronic acid) in vitro to form pectin-like substance referred to as synthetic pectin. (See, e.g., U.S. Pat. No. 2,156,223. Furthermore, the disclosed pectin and pectin-related substances may include naturally and non-naturally occurring polyuronic acids.

In the disclosed methods and compositions, pectin may be present at a desirable concentration, for example, in soil surrounding a plant, in a seed coating, or in animal feed. When pectin is administered to soil, the pectin may be administered, for example, to achieve a concentration in soil (w/w) of about 0.0001%, 0.0005%, 0.001%, 0.005%, 0.01%, 0.05%, 0.1%, 0.5%, 1%, 2%, 3%, 4%, or 5%, or to achieve a concentration in soil within a concentration range bounded by any of these percentage values (e.g., within a range of 0.001%-0.01%). When pectin is present in a seed coating, the pectin may be present at a concentration (w/w) in the coating of about 0.001%, 0.005%, 0.01%, 0.05%, 0.1%, 0.5%, 1%, 5%, 10%, 20%, 30%, 40%, 50%, or higher, or the pectin may be present at concentration (w/w) in the coating within a concentration range bounded by any two of these values (e.g., within a range of 0.1%-1%). When pectin is present in animal feed, the pectin may be present at a concentration (w/w) in the animal feed of about 0.005%, 0.01%, 0.05%, 0.1%, 0.5%, 1%, 2%, 3%, 4%, 5%, 10% or higher or the pectin may be present in the animal feed at within range concentration bounded by any two of these values (e.g., within a range of 0.1%-1%).

Inoculants

The presently disclosed PGPR may be formulated as an inoculant for a plant. The term "inoculant" means a preparation that includes an isolated culture of a PGPR and optionally a carrier. Inoculants comprising PGPR and carriers are known in the art. (See, e.g., Bashan, "Inoculants of Plant Growth-Promoting Bacteria for use in Agriculture," Biotechnology Advances, Vol. 16, No. 4, pp. 729-770, 1998). PGPR inoculants may be administered to plants (e.g. to the roots of plants), to seeds (e.g., as a coating for the seed or at the time that the seed is planted), or to soil (e.g., to soil surrounding plants to be treated).

A PGPR inoculant may be described as a formulation containing one or more PRPR species in a carrier material, which may be an organic carrier, an inorganic carrier, or a carrier synthesized from defined molecules. Optionally, the carrier may be sterile or sterilized prior to be formulated with the PGPR to form the PGPR inoculant. Preferably, the carrier is nontoxic, biodegradable and nonpolluting. In the disclosed inoculants comprising a pectin saccharide, the pectin saccharide optionally may function as a carrier or optionally the inoculants may comprise a carrier other than the pectin saccharide.

The carrier of the PGPR inoculant is the delivery vehicle for the live PGPR to the plant, seeds, or soil. The carrier represent is the major portion by volume or weight of the inoculant. Suitable carriers may include liquids, powders (e.g., having an average effective particle diameter of 0.075 to 0.25 mm), granulars (e.g., having an average effective particle diameter of 0.35 to 1.18 mm), and slurries which have the capacity to deliver a sufficient number of viable PGPR cells to the plant, seeds, or soil. Preferably, the carrier extends the shelf-life of the PGPR (e.g., such that the PGPR has a shelf-life of at least 1 or 2 years at room temperature). Examples of carriers include but are not limited to peat, coal, clays, inorganic soil material, plant waste materials, composts, farmyard manure, soybean meal, soybean oil, peanut oil, wheat bran, inert materials such as vermiculite, perlite, phosphate, polyacrylamide, alginate beads, oil-dried bacteria. In some embodiments, the PGPR may be encapsulated by a carrier, for example, where the carrier is a carbohydrate that forms a matrix around the PGPR.

The PGPR utilized in the disclosed composition and methods may be isolated or substantially purified. The terms "isolated" or "substantially purified" refers to PGPR that have been removed from a natural environment and have been isolated or separated, and are at least 60% free, preferably at least 75% free, and more preferably at least 90% free, even more preferably at least 95% free, and most preferably at least 100% free from other components with which they were naturally associated. An "isolated culture" refers to a culture of the PGPR that does not include significant amounts of other materials such as other materials which normally are found in soil in which the PGPR grows and/or from which the PGPR normally may be obtained. An "isolated culture" may be a culture that does not include any other biological, microorganism, and/or bacterial species in quantities sufficient to interfere with the replication of the "isolated culture." Isolated cultures of PGPR may be combined to prepare a mixed culture of PGPR.

The inoculant typically includes a suitable amount of PGPR relative to carrier. In some embodiments, the inoculant includes $10^2$-$10^{12}$ cfu PGPR per ml carrier (or per gram carrier), or $10^4$-$10^{10}$ cfu PGPR per ml carrier (or per gram carrier), or $10^6$-$10^8$ cfu PGPR per ml carrier (or per gram carrier). The composition may include additional additives including buffering agents, surfactants, adjuvants, or coating agents. Suitable carriers may include, but are not limited to, water or other aqueous solutions, slurries, solids (e.g., peat, wheat, bran, vermiculite, and pasteurized soil) or dry powders.

In the disclosed methods and compositions, PGPR may be present at a desirable concentration, for example, in soil surrounding a plant, in a seed coating, or in animal feed. In some embodiments where PGPR is applied to soil, PGPR may be applied as a seedling root-dip or as a soil drench at a concentration of about $10^2$-$10^{12}$ cfu/ml, $10^4$-$10^{10}$ cfu/ml, or about $10^6$-$10^8$ cfu/ml. In some embodiments where PGPR is present as a coating on a seed, suitable application concentrations may be between $10^2$-$10^8$ cfu per seed, preferably $10^4$-$10^7$ cfu per seed. In some embodiments where PGPR is present in animal feed, the PGPR may be presented at a concentration of at least about $10^4$ CFU/g of feed. More preferably, the spore-forming strain of the genus *Bacillus* is present in the composition at a concentration of at least about $10^5$ CFU/g of feed. Even more preferably, the spore-forming strain of the genus *Bacillus* is present in the composition at a concentration of at least about $10^6$ CFU/g of feed or per ml of water or at least about $10^7$ CFU/g of feed or per ml of water. A suitable concentration range may include $10^4$-$10^7$ CFU/g of feed or per ml of water or sub-ranges there within.

The disclosed inoculants and compositions may include additional agents for promoting plant growth and health, including additional agents for promoting nodulation. The additional agents may include additional bacterial inoculants, including, but not limited to, additional rhizobacteria such as a nitrogen-fixing bacteria and/or a phosphate-solubilizing bacteria. Additional agents may include fungal inoculants, for example mycorrhizae. Additional agents may include plant nutrients such as nitrogen salts and/or phosphate salts and/or potassium salts.

Methods of Treating Plants, Seeds, or Soil

Also disclosed are methods of using pectin or pectin-related saccharides to improve the efficacy of PGPR in regard to promoting growth or health in plant. The disclosed methods for promoting growth or health in plant may include, but are not limited to, methods of increasing nodulation in legumes. The disclosed methods may include administering the above-described inoculants comprising a PGPR and a pectin saccharide to plants, seeds, or soil. In some embodiments, the disclosed methods for improving plant growth or plant health may include: (a) treating plants, seeds, or soil with a plant growth promoting rhizobacteria (PGPR) that expresses a protein associated with pectin metabolism and (b) treating the plants, seeds, or soil with a saccharide comprising pectin or a pectin-related saccharide (e.g., hydrolyzed pectin, D-galacturonate, D-glucuronate, or mixtures thereof), where the plants, seeds, or soil may be treated with the PGPR and the saccharide concurrently or in either order (i.e., the PGPR may be administered before, concurrently with, or after the saccharide is administered). The PGPR and pectin saccharide may be formulated as an inoculant and administered concurrently to treat plants (e.g., administered to the roots of plants), to seeds (e.g., as a coating for seeds), or to soil (e.g., as a soil amendment).

The disclosed methods may be utilized to improve plant growth or plant health by controlling soil-borne pests. Soil-borne pests controlled by the disclosed methods may include but are not limited to nematodes and herbivorous insects. The disclosed methods may be utilized to improve plant growth or plant health by controlling or treating a disease. Disease controlled or treated by the disclosed methods may include but are not limited to a bacterial disease, a fungal disease, and a viral disease.

The presently disclosed PGPR and pectin saccharide may be administered as an inoculant for treating plants. The methods of treatment contemplated herein may include treating a plant directly including treating leaves, stems, or roots of the plant directly. The methods of treatment contemplated herein may include treating seeds of the plant, e.g., coating the seeds prior to the seeds being planted to produce a treated plant. The methods contemplated herein also may include treating a plant indirectly, for example, by treating soil or the environment surrounding the plant (e.g., in-furrow granular or liquid applications). Suitable methods of treatment may include applying an inoculant including the PGPR and the saccharide via high or low pressure spraying, drenching, and/or injection. Plant seeds may be treated by applying low or high pressure spraying, coating, immersion, and/or injection. After plant seeds have been thusly treated, the seeds may be planted and cultivated to produce plants. Plants propagated from such seeds may be further treated with one or more applications. Suitable application concentrations may be determined empirically. In some embodiments where the PGPR and pectin saccharide are applied as a spray to plants, suitable application concentrations may include spraying $10^6$-$10^{18}$ colony forming units (cfu) per hectare of plants, more commonly $10^7$-$10^{15}$ cfu per hectare. For coated seeds, in some embodiments, suitable application concentrations may be between $10^2$-$10^8$ cfu per seed, preferably $10^4$-$10^7$ cfu per seed. In other embodiments, the PGPR and pectin saccharide may be applied as a seedling root-dip or as a soil drench at a concentration of about $10^2$-$10^{12}$ cfu/ml, $10^4$-$10^{10}$ cfu/ml, or about $10^6$-$10^8$ cfu/ml.

Methods of Treating Animals

*Bacillus* species isolates cultured from plant rhizospheres have the ability to utilize complex plant polysaccharides as a carbon and energy source. Increasingly, animal feeds are plant based and many of the plant-derived polysaccharides and other compounds (e.g. phytic acid) are not readily degraded or utilized by fish, poultry or livestock. In fact, in many cases these plant-derived compounds such as phytic acid serve as an anti-nutrient that can make animals anemic. Using *Bacillus* or other species that can degrade complex plant polysaccharides can promote feed conversion efficiency and these rhizosphere isolates are ideally suited to help improve animal feeds and degrade phytic acid to improve animal nutrition.

As such, also disclosed are methods of using pectin or pectin-related saccharides to improve the efficacy of PGPR in regard to promoting growth or health in animals. The disclosed methods may include administering the afore-described inoculants comprising a PGPR and a pectin saccharide to animals (e.g., in the form of an animal feed composition such as a pelleted feed composition comprising the afore-described inoculants). In some embodiments, the disclosed methods for improving animal growth or animal health may include: (a) administering to an animal a plant growth promoting rhizobacteria (PGPR) that expresses a protein associated with pectin metabolism and (b) administering to the animal a pectin saccharide comprising pectin or a pectin-related saccharides (e.g., hydrolyzed pectin, D-galacturonate, D-glucuronate, or mixtures thereof), where the animals may be administered the PGPR and the pectin saccharide concurrently or in either order (i.e., the PGPR may be administered before, concurrently with, or after the saccharide is administered).

Feed compositions comprising the PGPR and pectin saccharide may be administered to animals orally. Oral administration includes, but is not limited to, delivery in feed, water, by oral gavage or aerosol spray. If supplied in an animal feed, the feed may comprise between $10^4$ and $10^9$ cfu PGPR/gm of finished feed. Suitably the feed comprises between $10^5$ and $5 \times 10^7$ cfu PGPR/gm feed. The PGPR and pectin saccharide may be added to the feed during production, after production by the supplier, or by the person feeding the animals, just prior to providing the food to the animals.

An animal feed composition may be prepared by forming a mixture of the animal feed and an inoculant as discussed above, and then optionally forming a compressed or pelleted animal feed from the mixture. Animal feed suitable for preparing animal feed compositions as disclosed herein may include animal feed comprising plant material (e.g., hay straw, silage, grains (e.g., maize, soybean, wheat, oats, barley, sorghum, and rice), and legumes). Animal feed suitable for preraing animal feed compositions as disclosed herein any include fish products (e.g., fish oils and fish proteins).

The disclosed methods for promoting growth or health in animals may be practiced in order to increase overall gastrointestinal health, improve production performance, and reduce enteric bacterial pathogens of importance to both animal health and human food safety. These PGPR and pectin saccharide may be added to animal diets at the rate of about $10^4$ to $10^9$ PGPR per gram of finished feed for optimal inclusion rate, if the bacteria or probiotic compositions being administered continuously, and a higher inclusion rate may be necessary if the PGPR or the compositions are provided intermittently. While administration though the feed is a preferred route of administration, the PGPR and pectin saccharide may also be administered via drinking water, through course spray, through aerosol spray, or through any other means by which the agricultural animals may ingest these PGPR and pectin saccharide.

The disclosed methods may include methods of promoting growth or health in aquatic animals, which may include farmed fish (e.g. catfish or tilapia) and crustaceans (e.g., shrimp). The term "catfish" refers to a fish belonging to the genus *Ictaluri*. Catfish may include the species *Ictaluri punctatus* Rafinesque.

Methods for Preparing the Disclosed Compositions and Inoculants

Also disclosed are methods of using pectin or pectin-related saccharides to prepare compositions and inoculants as disclosed herein. The methods may include combining PGPR and pectin, which has been extracted from pectin-containing plant material, or pectin-related saccharides to prepare the disclosed compositions and inoculants. Optionally, a carrier may be combined with the PGPR and pectin or pectin-related saccharides to prepare the disclosed compositions and inoculants.

In some embodiments, the methods may include combining $10^2$-$10^{12}$ cfu PGPR per ml carrier (or per gram carrier), or $10^4$-$10^{10}$ cfu PGPR per ml carrier (or per gram carrier), or $10^6$-$10^8$ cfu PGPR per ml carrier (or per gram carrier). In some embodiments, the methods may include combining pectin, which has been extracted from pectin-containing plant material, or pectin-related saccharides may be combined with PGPR and optionally a carrier to prepare the disclosed compositions and inoculants, wherein the pectin or pectin-related saccharides are present in the prepared compositions and inoculants at a concentration of at least about 0.1%, 0.5%, 1.0%, 1.5%, or 2.0% (w/w or w/v) to about 0.5%, 1.0%, 1.5%, 2.0%, or 5.0% (w/w or w/v). In some embodiments, the methods may include combining PGPR and pectin at a concentration of about at least about $10^2$, $10^3$, $10^4$, $10^5$, $10^6$, $10^7$, $10^8$, $10^9$, $10^{10}$, $10^{11}$, $10^{12}$, $10^{13}$, or $10^{14}$ cfu PGPR per gram pectin or pectin-related saccharides, to about $10^3$, $10^4$, $10^5$, $10^6$, $10^7$, $10^8$, $10^9$, $10^{10}$, $10^{11}$, $10^{12}$, $10^{13}$, $10^{14}$, $10^{15}$ cfu PGPR per gram pectin or pectin-related saccharides (e.g., ranges such as $10^7$ to $10^{12}$ cfu PGPR per gram pectin or pectin-related saccharides are contemplated herein). In the methods, additional additives including buffering agents, surfactants, adjuvants, and coating agents may be combined with the PGPR, pectin or pectin-related saccharides, and optional carrier in order to prepare the disclosed compositions and inoculants. Compositions and inoculants prepared by the afore-disclosed methods also are contemplated herein.

EXAMPLES

The following Examples are illustrative and are not intended to limit the scope of the claimed subject matter.

Example 1—Deciphering the Conserved Genetic Loci Implicated in Plant Disease Through Comparative Genomics of *Bacillus amyloliquefaciens* Subsp. *Plantarum* (Now *Bacillus velezensis*) Strains Reference is made to Hossain et al., "Deciphering the conserved genetic loci implicated in plant disease through comparative genomics of *Bacillus amyloliquefaciens* subsp, *plantarum* [(now *Bacillus velezensis*)] strains," Frontiers in Plant Science, 2015 Aug. 17; 6:631 doi: 10.3389/fpls.2015.00631. eCollection 2015, (hereinafter referred to as "Hossain et al., Frontiers Plant Science 2015), the content of which is incorporated herein by reference in its entirety.

Abstract

To understand the growth-promoting and disease-inhibiting activities of plant growth-promoting rhizobacteria (PGPR) strains, the genomes of 12 *Bacillus subtilis* group strains with PGPR activity were sequenced and analyzed. These *B. subtilis* strains exhibited high genomic diversity, whereas the genomes of *B. amyloliquefaciens* strains (a member of the *B. subtilis* group) are highly conserved. A pairwise BLASTp matrix revealed that gene family similarity among *Bacillus* genomes ranges from 32-90%, with 2,839 genes within the core genome of *B. amyloliquefaciens* subsp. *plantarum* (now *B. velezensis*). Comparative genomic analyses of *B. amyloliquefaciens* strains identified genes that are linked with biological control and colonization of roots and/or leaves, including 73 genes uniquely associated with subsp. *plantarum* (now *B. velezensis*) strains that have predicted functions related to signaling, transportation, secondary metabolite production, and carbon source utilization. Although *B. amyloliquefaciens* (now *B. velezensis*) strains contain gene clusters that encode many different secondary metabolites, only polyketide biosynthetic clusters that encode difficidin and macrolactin are conserved within this subspecies. To evaluate their role in plant pathogen biocontrol, genes involved in secondary metabolite biosynthesis were deleted in *B. amyloliquefaciens* (now *B. velezensis*) strain, revealing that difficidin expression is critical in reducing the severity of disease, caused by *Xanthomonas axonopodis* pv. vesicatoria in tomato plants. This Example defines genomic features of PGPR strains and links them with biocontrol activity and with host colonization.

Introduction

Bacteria associated with plant roots that exert beneficial effects on plant growth and development are referred to as plant growth-promoting rhizobacteria (PGPR) (Kloepper and Schroth, 1978; Kloepper et al., 2004). *Bacillus* and *Pseudomonas* spp. are predominant among the diverse bacterial genera that have been linked with PGPR activity (Podile and Kishore, 2006). Members of the *B. subtilis* group, including *B. subtilis*, *B. licheniformis*, *B. pumilus*, *B. amyloliquefaciens*, *B. atrophaeus*, *B. mojavensis*, *B. vallismortis*, *B. sonorensis*, and *B. tequilensis* have been identified as PGPR strains for their capacity to stimulate plant growth and suppress pathogens within rhizosphere and phyllosphere (Kloepper et al., 2004; Hao et al., 2012; Kim et al., 2012). Strains of *B. amyloliquefaciens* are widely used for their positive effects on plant growth (Idriss et al., 2002). Reva et al. (Reva et al., 2004) reported that seven *Bacillus* isolates from plants or soil are closely related yet distinct from *B. amyloliquefaciens* type strain DSM7$^T$. In addition, these strains are more proficient for rhizosphere colonization than other members of the *B. subtilis* group. GB03 (Nakkeeran et al., 2005), INR7 (Kokalis-Burelle et al., 2002) and FZB42 (Chen et al., 2007a) are PGPR strains within the *Bacillus subtilis* group that have been widely used in different commercial formulations to promote plant growth.

In addition to promoting plant growth, PGPR strains may exhibit biological control of plant diseases. Antibiosis, through the production of inhibitory bioactive compounds, and induced systemic resistance are widely reported biological control mechanisms of *Bacillus* spp. PGPR strains (Ryu et al., 2004). PGPR *Bacillus* spp. strains produce diverse antimicrobial compounds including antibiotics (Emmert et al., 2004), volatile organic compounds (VOCs) (Yuan et al., 2012), and lipopeptides (Ongena et al., 2007) that are associated with the observed biocontrol activity against plant pathogens. For example, *B. amyloliquefaciens* NJN-6 produces 11 VOCs that provide antifungal activity against *Fusarium oxysporum* f. sp. *cubense* (Yuan et al., 2012). Similarly, *B. subtilis* strains produce lipopeptides (e.g. surfactin and fengycin), that induce systemic resistance in bean plants (Ongena et al., 2007). PGPR strains usually need to colonize plant roots extensively to exert plant growth promoting effects using both direct and indirect mechanisms (Lugtenberg and Kamilova, 2009), extensive root colonization is not required for induced systemic resistance (ISR) (Kamilova et al., 2005). In some PGPR strains, root colonization is a prerequisite for biocontrol activity through antibiosis (Chin et al., 2000). For example, *B. amyloliquefaciens* (now *B. velezensis*) FZB42 exerts growth promoting activities through efficient colonization of plant roots (Fan et al., 2011). Previously, it has been demonstrated that over-expression of genes involved in phosphorylation of DegU, a two-component response regulator of *B. amyloliquefaciens* strain SQR9, positively influences root colonization as well as other growth-promoting activities by PGPR strains for controlling cucumber wilt disease (Xu et al., 2014). Moreover, the root colonization capacity of a poor root colonizer can be improved by cloning genes that are required for efficient root colonization (Dekkers et al., 2000). Competitive root colonization by PGPR are controlled by many genes and/or genetic cluster(s) (Dietel et al., 2013), so identification of these genetic loci involved in competitive root colonization are challenging if genome sequences are lacking for those PGPR strains (Lugtenberg and Kamilova, 2009). Analysis of additional PGPR strains will help elucidate the mechanisms of competitive root colonization, antibiosis and ISR of PGPR strains and form a foundation for genetic engineering and other strategies to increase the plant-growth promoting capacity of these bacteria.

In this Example, we sequenced the genomes of 12 *Bacillus subtilis* group isolates from diverse locales. Comparative genomic analyses of PGPR strains and control strains of the *B. subtilis* group without any reported biocontrol activity against plant pathogens provides insight into genomic features involved in PGPR activity. PGPR strain AP193, which inhibits growth of plant and animal bacterial pathogens (Ran et al., 2012), is an ideal candidate to evaluate the relative contribution of genes that are predicted to be involved in the biosynthesis of bioactive secondary metabolites that could contribute to biocontrol activity, specifically difficidin (dfnD mutant), surfactin (srfAA mutant), as well as all polyketides and lipopeptides produced by non-ribosomal peptide synthesis, including difficidin (sfp mutant). Mutants were then tested for their ability to inhibit plant pathogens in vitro and control bacterial spot disease in tomato.

Materials and Methods

Bacterial Strains, Plasmids and Growth Conditions.

Bacterial strains and plasmids used in this Example are listed in Table 1. *E. coli* and *Bacillus* strains were grown in Luria-Bertani (LB) medium; however, for electrocompetent cell preparation, *Bacillus amyloliquefaciens* subsp. *plantarum* (now *Bacillus velezensis*) AP193 was grown in NCM medium (17.4 g $K_2HPO_4$, 11.6 g NaCl, 5 g glucose, 5 g tryptone, 1 g yeast extract, 0.3 g trisodium citrate, 0.05 g $MgSO_4 \cdot 7H_2O$ and 91.1 g sorbitol in 1 L deionized water, pH 7.2). For production of secondary metabolites, *Bacillus* cultures were grown for 48 h at 30° C. in Tryptic Soy broth (TSB). In addition, ampicillin (100 μg/ml), chloramphenicol (12.5 μg/ml) or erythromycin (200 μg/ml for *E. coli* or 5 μg/ml for *Bacillus*) were used as selective agents in growth media as required.

Sequencing, Assembly and Annotation.

Next-generation sequencing of *Bacillus* spp. genomes was performed using Illumina and Roche 454 sequencing platforms. Indexed Illumina libraries were prepared for strains AP71, AP79, and AB01 using Nextera DNA Sample Prep Kit (Epicentre, Madison, Wis.) and sequences were generated using an Illumina MiSeq with a 2×250 paired end sequencing kit. Barcoded Illumina libraries for strains AP143, AP193, and AP254 were constructed using a NxSeq® DNA Sample Prep Kit (Lucigen, Middleton, Wis.) and sequenced at EnGenCore (Univ. of South Carolina) using the 454-pyrosequencing platform. Genomic DNA library construction and sequencing for *Bacillus subtilis* GB03, *Bacillus pumilus* INR7, *B. mojavensis* KCTC 3706T, *B. tequilensis* KCTC 13622T, *Bacillus siamensis* KCTC 13613T, and *B. sonorensis* KCTC 13918T were conducted at the National Instrument Center for Environmental Management (Seoul, Republic of Korea), using the Illumina HiSeq 2000 sequencing platform. Sequence reads were trimmed for quality then assembled de novo using the CLC Genomics Workbench (CLCBio, Cambridge, Mass.). Gene prediction and annotation were performed using GeneMark (Lukashin and Borodovsky, 1998) and the RAST annotation server (Aziz et al., 2008), respectively. The identity of individual open reading frames (ORFs) from secondary metabolite biosynthesis gene clusters was confirmed by BLASTx against the GenBank database. Genome sequence reads for strains AB01, AP71, AP79, AP143, AP193, AP254, GB03 (Choi et al., 2014), INR7 (Jeong et al., 2014), KCTC 3706T, KCTC 13613T (Jeong et al., 2012), KCTC 13918T, and KCTC 13622T were deposited into the Short Read Archive (SRA) at NCBI under the accession numbers SRR1176001, SRR1176002, SRR1176003, SRR1176004, SRR1176085, and SRR1176086, SRR1034787, SRR1141652, SRR1141654, SRR1144835, SRR1144836, and SRR1144837, respectively.

Determination of Average Nucleotide Identity.

Average nucleotide identities (ANI) between genomes were calculated using an ANI calculator that estimates ANI according to the methods described previously (Goris et al., 2007).

Phylogenetic Analysis of *Bacillus* Species.

For phylogenetic analysis, the gyrB gene sequence for each strain was retrieved from sequence data. (See Hossain et al., Frontiers Plant Science 2015, FIG. 1). Strains AS43.3, FZB42, YAU B9601-Y2, CAU B946, and 5B6 were used as representative strains of *B.s amyloliquefaciens* subsp. *plantarum* (now *B. velezensis*); strains DSM7, LL3 and TA208 were used as representative strains of *B. amyloliquefaciens* subsp. *amyloliquefaciens*. The gyrB phylogenetic tree was inferred with MEGA5.05 (Tamura et al., 2011) using Neighbor-Joining (Saitou and Nei, 1987) and Maximum Likelihood (ML) methods (Felsenstein, 1981). All positions that contained gaps or missing data were eliminated from the final dataset, resulting in 1911 bp positions of gyrB sequence. We used 729,383 bp of DNA to represent the conserved core genome found across 25 strains of the *B. subtilis* group, to generate a phylogenomic tree using RAxML (v 7.2.7) (Pfeiffer and Stamatakis, 2010). The phylogenomic tree was then visualized with iTOL (http://itol.embl.de)(Letunic and Bork, 2011).

Blast Matrix.

The BLAST matrix algorithm was used for pairwise comparison of *Bacillus* PGPR strain proteomes, using methods described previously (Friis et al., 2010). The BLAST matrix determines the average percent similarity between proteomes by measuring the ratio of conserved gene families shared between strains to the total number of gene families within each strain. The absolute number of shared and combined gene families for each strain was displayed in matrix output. This matrix shows the number of proteins shared between each proteome.

Core-Genome Analysis.

The core-genome of 13 *Bacillus* spp. strains was generated using coding and non-coding sequences. Whole genome sequences from these strains were aligned using progressive Mauve (Darling et al., 2004), which identifies and aligns locally collinear blocks (LCBs) in the XMFA format. LCBs from alignments were collected using strip-SubsetLCBs (http://gel.ahabs.wise.edu/mauve/snapshots/), using minimum lengths of 500 bp. All LCBs were concatenated and converted to multifasta format using a perl script. The same protocol was used to obtain all core sequences, with the exception that the minimum lengths of LCBs were 50 bp, instead of 500 bp. The *Bacillus* spp. core genome was obtained from the comparative alignment of all complete *Bacillus* spp. genomes available in the GenBank as of August 2014 (n=81 genomes). The core genome of the *B. subtilis* group was obtained from comparative analysis of 53 whole genomes of *B. subtilis* strains that included 41 genomes obtained from GenBank and 12 PGPR genomes sequenced in this Example. *B. amyloliquefaciens* species-level and *B. amyloliquefaciens* subsp. *plantarum* (now *Bacillus velezensis*)-level core genomes were generated from 32 *B. amyloliquefaciens* and 28 subsp. *plantarum* (now *B. velezensis*) genomes. Core genomes were exported to the CLC Genomics Workbench (v 4.9) for evaluation of alignments and annotation using the RAST server (Aziz et al., 2008). The list of *Bacillus* spp. strains used for core genome determination is provided in Table 2. Additionally, to identify GPR-specific core genes, raw sequence reads of PGPR strains sequenced in this Example were sequentially reference mapped against the genome sequence of non-PGPR strain *B. subtilis* subsp. *subtilis* str. 168 according to methods described previously (Hossain et al., 2013).

Identification of Core Genes Uniquely Present in *B. amyloliquefaciens* Subsp. *Plantarum* (Now *Bacillus Venezensis*) Strains.

The aligned genome sequences of 32 *B. amyloliquefaciens* strains and 28 *B. amyloliquefaciens* subsp. *plantarum* (now *Bacillus velezensis*) strains (which were included within the *B. amyloliquefaciens* strains) were analyzed using CLC Genomics Workbench to obtain the respective species- and subsp.-level core genomes. Trimmed sequence reads of subsp. *plantarum* (now *B. velezensis*) strain AP193 were reference mapped against the subsp. *plantarum* (now *B. velezensis*) core genome to obtain core genome-specific sequence reads. The parameters of reference mapping were as follows: mismatch cost=2, insertion cost=3, deletion cost=3, length fraction=0.5, and similarity=0.8. Sequence reads mapped to the subsp. *plantarum* (now *B. velezensis*) core genome were then mapped against the species *amyloliquefaciens* core genome to obtain unmapped sequence reads. These unmapped sequence reads, represent the subsp. *plantarum* (now *B. velezensis*) core genome that is absent in the *amyloliquefaciens* species-level core genome, were assembled de novo using CLC Genomics Workbench then the resulting contigs were uploaded to RAST for gene prediction and annotation. Each ORF, exclusively encoded by the *plantarum* (now *B. velezensis*) core genome, was further confirmed for uniqueness using BLASTn analysis against the genome sequences of 28 *B. amyloliquefaciens* subsp. *plantarum* (now *B. velezensis*) and four *B. amyloliquefaciens* subsp. *amyloliquefaciens* strains listed in Table 2.

Prediction of Secondary Metabolite Biosynthesis Gene Clusters in PGPR Strain AP193.

Secondary metabolite biosynthesis gene clusters for strain AP193 were predicted using the secondary metabolite identification tool antiSMASH (Blin et al., 2013). Primer-walking PCR was used to fill gaps between contigs containing gene clusters encoding secondary metabolite biosynthesis. Gene prediction and annotation were carried out by GeneMark (Lukashin and Borodovsky, 1998) and BLASTx (NCBI), respectively.

DNA Manipulation and Plasmid Construction for PGPR Strain AP193 Mutagenesis.

Chromosomal DNA was isolated with the E.Z.N.A. Bacterial DNA Isolation Kit (Omega Biotek, Atlanta, Ga.) and plasmids were isolated with the E.Z.N.A. Plasmids Mini Kit II (Omega Biotek). Gene deletion constructs were assembled using splicing through overlap extension PCR (Horton et al., 1989). The assembled products were gel purified with Gel/PCR DNA Fragments Extraction Kit (IBI), digested with appropriate restriction enzymes, and cloned into a pNZT1 vector to construct the delivery plasmids for gene replacement.

In Vitro Plasmid Methylation Using Cell Free Extract of *Bacillus amyloliquefaciens* Subsp. *Plantarum* (Now *B. velezensis*) AP193.

To methylate plasmids prior to transformation into *B. amyloliquefaciens* subsp. *plantarum* (now *B. velezensis*) AP193, the method developed for *Lactobacillus plantarum* was used with minor modifications (Alegre et al., 2004). Cells from a 100 ml overnight culture of strain AP193 ($OD_{600}$=1.3-1.5) were pelleted by centrifugation (8000×g), washed with 100 ml of chilled PENP buffer (10 mM potassium phosphate, 10 mM EDTA, 50 mM NaCl and 0.2 mM PMSF, pH 7.0), and then re-suspended to a final volume of 4 ml. Cells were disrupted by performing two bursts (amplitude 50, pulse 3 and watts 25-30) for 5 min each with a pause of 2 min, using a Vibra-Cell sonicator, and cooled with ice to prevent overheating. Cell debris was removed by centrifugation (8000×g) at 4° C. and the extract was collected through decanting. Three ml aliquots of extract were mixed with 3 ml of glycerol (100% v/v) and 0.6 ml of bovine serum albumin (1 mg/ml), then stored at −20° C.

The DNA modification assay was performed in a final volume of 100 µl of the following: 53 µl THE buffer [50 mM Tris (pH 7.5), 50 mM NaCl, 10 mM EDTA], 10 µl S-adenosylmethionine (0.8 mM), 2 µl BSA (5 mg/ml), 25 µl cell free extract derived from strain AP193 and 10 µl plasmid DNA extracted from *E. coli* K12 ER2925 (0.5-1 µg/µl). The mixture was incubated at 37° C. for 16 h. Methylated DNA was extracted with a DNA Clean & Concentrator Kit (Zymo Research, CA), then re-suspended in water and stored at −20° C.

Electrotransformation of *B. amyloliquefaciens* Subsp. *Plantarum* (Now *B. Velezensis*) AP193.

For preparation of electrocompetent cells, strain AP193 was grown overnight in TSB, then diluted 100-fold in NCM to inoculate a subculture. The culture was grown at 37° C. on a rotary shaker until the $OD_{600}$ reached 0.7. The cell culture was cooled on ice for 15 min and subjected to centrifugation at 8000×g for 5 min at 4° C. After washing four times with ice cold ETM buffer (0.5 M sorbitol, 0.5 M mannitol, and 10% glycerol), electrocompetent cells were re-suspended in 1/100 volume of the original culture (Zhang et al., 2011). For electroporation, 100 µl of cells were mixed with 100 ng of plasmid DNA in an ice-cold electroporation cuvette (1 mm electrode gap). Cells were exposed to a single 21 kV/cm pulse generated by Gene-Pulser (Bio-Rad Laboratories) with the resistance and capacitance set as 200Ω and 3 µF, respectively. The cells were immediately diluted into 1 ml of recovery medium (NCM plus 0.38M mannitol) (Zhang et al., 2011) and shaken gently at 30° C. or 37° C. for 3 h to allow expression of the antibiotic resistance genes. Aliquots of the recovery culture were then spread onto LB agar supplemented with appropriate antibiotics.

Two-Step Replacement Recombination Procedure for the Modification of the Strain AP193 Genome.

A two-step replacement recombination was performed as previously described, with minor modifications (Zakataeva et al., 2010). To integrate the plasmid into AP193's chromosome, a single crossover between the target gene and the homologous sequence on the plasmid must occur. To do this, AP193 that contained a delivery plasmid with the deletion construct was first grown in LB broth for 24 h at 37° C. (a non-permissive temperature for plasmid replication). Next, the culture was serially diluted, plated onto LB agar plates with erythromycin, and incubated at 37° C. Clones were screened by colony PCR using two sets of primers. Each set of primers anneals sequences specific to one of the homologous fragments and to the chromosomal region just outside of the other homologous fragment. If PCR products had a reduced size, relative to the wild-type genotype for either primer set, this indicated successful chromosomal integration of the plasmid. In the second step, clones of the integrant were cultured with aeration in LB at 30° C. for 24-48 h to initiate the second single-crossover event, resulting in excision of the plasmid, yielding erythromycin sensitive (EmS) clones with either a parental or a mutant allele on the chromosome. Colony PCR was used to examine the presence of desired mutations by primer sets that flank the deleted sequence.

Construction of Strain AP193 Mutants Defective in Secondary Metabolite Biosynthesis.

All mutant strains generated in this Example are indicated in Table 1. The disruption of the dfnD gene was achieved as follows: DNA fragments corresponding to positions −867 to +247 and +643 to +1570 with respect to the dfnD translation initiation site were PCR amplified using AP193 genomic DNA as a template. The two fragments were then assembled by fusion PCR. A frameshift mutation was introduced during fusion to ensure complete disruption of the gene. The deletion construct was digested with XhoI and SpeI, then cloned into pNZT1, yielding pNZ-dif. The plasmid was methylated in vitro as described above and introduced into strain AP193 by electroporation. Once introduced into strain AP193, plasmid pNZ-dif generated the isogenic mutant AP193ΔdfnD by two-step replacement recombination.

To generate the sfp deletion mutant, DNA fragments corresponding to positions −781 to +29, with respect to the sfp translation initiation site, and +95 to +935, with respect to the sfp translation termination site, were PCR amplified using AP193 genomic DNA as template, assembled by fusion PCR, digested with HindIII and PstI, and cloned into pNZT1 to construct pNZ-sfp. The plasmid pNZ-sfp was used to generate mutant AP193Δsfp using procedures described above.

The ΔsrfAA mutant was obtained as follows: DNA fragments corresponding to positions +5375 to +6091 and +6627 to +7366, with respect to the srfAA translation initiation site, were PCR-amplified, fused by fusion PCR, digested with HindIII and PstI and cloned into pNZT1 as pNZ-srf. Similarly, a frameshift mutation was introduced during the fusion of the upstream and downstream fragments of the target deletion sequence to ensure complete disruption of the gene. The plasmid pNZ-srf was used to generate mutant AP193ΔsrfAA using procedures described above.

In Vitro Antimicrobial Activities of PGPR Strain AP193 and its Mutants Against Plant Pathogens.

Plant pathogens *Pseudomonas* syringe pv. *tabaci*, *Rhizobium radiobacter*, *Xanthomonas axonopodis* pv. vesicatoria, and *Xanthomonas axonopodis* pv. *campestris* were grown in TSB until the $OD_{600}$ reached 1.0. The wild type strain AP193, as well as the three isogenic mutants ΔdfnD, Δsfp, and ΔsrfAA developed in this Example, were grown at 30° C. in TSB for 48 h at 220 rpm. Cultures were then centrifuged at 10,000×g for 2 min then supernatant was passed through a 0.2 µm nylon filter (VWR, PA). For antibiosis assays, 100 µl of an overnight culture for each plant pathogen was spread onto TSA plates (Thermo Scientific, NY) separately then sterile cork borers (10 mm diameter) were used to bore wells in agar plates. Filtered supernatant of AP193 and its three mutants were separately added to fill wells. Plates were allowed to dry and then incubated at 30° C. overnight. Zones of inhibition were measured and compared between mutants and wild-type strain AP193 to determine their antimicrobial activities against plant pathogens.

LC-MS Analysis of Bacterial Supernatants.

Bacterial cultures were grown in 2 ml TSB for 72 hours and then cells were removed by centrifugation at 10,000×g for 10 min, followed by 0.2 μm filtration of the culture supernatant. Samples were analyzed by direct injection from m/z 50-1200 on a ultra-high pressure liquid chromatography/QTof-mass spectrometer (Waters Acquity UPLC and Q-Tof Premier, Milford, Mass.) operated at a spray voltage of 3.03 kv and the source temperature of 100° C. The MS analysis was conducted in negative ion mode with a mobile phase of 95% acetonitrile, 5% water and 0.1% formic acid.

In Vivo Antibiosis of Strain AP193 and its Mutants Against a Plant Pathogen.

Rutgers tomato seeds (Park Seed, USA) were sown in Styrofoam trays. Three weeks after planting, seedlings were transplanted into a 4.5 inch square pot with commercial potting substrate (Sunshine mix, Sun Gro Horticulture, Agawam, Me.). Three days after transplanting, plants were sprayed with sterile water or PGPR cell suspensions ($10^6$ CFU/ml) that had been washed three times prior to being resuspended in sterile water and normalized at an $OD_{600}$=1.0 before being serially diluted. PGPR-inoculated plants were placed into a dew chamber at 100% humidity in the dark for two days at 24° C. then transferred to the greenhouse. One day later, plants were challenge-inoculated with *X. axonopodis* pv. vesicatoria by spraying approximately 10 ml of a $10^7$ CFU/ml pathogen suspension over each plant. Pathogen-inoculated plants were placed in the dew chamber for two days then placed in the greenhouse. Plants were watered once daily. Disease severity ratings and harvest were conducted after 14 days of challenge-inoculation. For disease severity rating, four compound leafs were selected from the bottom of each plant. The disease severity of each of the compound leaves was determined by rating the disease severity of each leaflet and calculating the average rating for the compound leaf. Leaflets were rated using a 0-4 rating scale, where 0=healthy leaflet, 1=<20% necrotic area of the leaflet, 2=20-50% necrotic area of the leaflet, 3=51-80% necrotic area of the leaflet, 4=80-100% necrotic area of the leaflet. In addition, dry shoot and root weights were determined. The experimental design was a randomized complete block with ten replications per treatment. The experiment was conducted twice.

Data Analysis.

All data were analyzed by an analysis of variance (ANOVA), and the treatment means were separated by using Fisher's protected least significant difference (LSD) test at P=0.05 using SAS 9.3 (SAS Institute, Gary, N.C., USA).

Results

Genome Statistics and Genetic Relatedness of *Bacillus* Species.

Genome sequences of 12 different PGPR *Bacillus* spp. strains were determined using next-generation sequencing. The summary statistics for each *Bacillus* spp. genome sequences and their assemblies are presented in Table 2. The approximate sizes of *Bacillus* spp. genomes ranged from 2.95-4.43 Mbp with an average genome size of 3.93 Mbp, which is similar to the 4.09 Mbp average genome size of complete *B. subtilis* genomes available in GenBank (April, 2015). The percent G+C content of the 12 PGPR *Bacillus* spp. strains ranged from 41.3-46.6%, averaging 45.15%, which is similar to the average percent G+C content of the *B. subtilis* genome sequences available in GenBank (43.72%) (March, 2015). Pairwise average nucleotide identities (ANI), a newly proposed standard for species definition in prokaryotes (Richter and Rosselló-Móra, 2009), were calculated for 13 *Bacillus* PGPR strains to determine their interspecies relatedness among *Bacillus* species. The ANI values for PGPR *Bacillus* spp. strains AB01, AP71, AP79, AP143, AP193, and GB03 against *B. amyloliquefaciens* (now *B. velezensis*) FZB42 (Chen et al., 2007a) were greater than 98% (data not shown), indicating that these PGPR strains are affiliated with the *B. amyloliquefaciens* species. The 98.88% ANI of PGPR strain AP254 to *B. subtilis* subsp. *subtilis* strain 168 suggests that AP254 is affiliated with *B. subtilis* (data not shown). The pairwise ANI comparison of PGPR strains INR7, KCTC 3706T, KCTC 13613T, KCTC 13918T, and KCTC 13622T against each other produce ANI values less than 95% (data not shown) suggests that they are distantly related to each other and represent diverse *Bacillus* species.

Phylogenetic Relationship of *Bacillus* Strains.

A phylogenetic analysis based on gyrB gene sequences showed sufficient resolution among *Bacillus* taxa and was consistent with ANI comparisons. Strains AP71, AP79, AP143, AP193, AB01, and GB03 were grouped together with reference strains of *B. amyloliquefaciens* subsp. *plantarum* (now *B. velezensis*) with high bootstrap support, indicating that they are affiliated with subsp. *plantarum* (now *B. velezensis*). The three strains of *B. amyloliquefaciens* subsp. *amyloliquefaciens* DSM7, TA208, and LL3 clustered as a single clade, separated from strains of subsp. *plantarum* (now *B. velezensis*), supporting the division of two subspecies in *B. amyloliquefaciens* (Borriss et al., 2011). The placement of strain AP254 with *B. subtilis* subsp. *subtilis* strain 168 as a single Glade with strong bootstrap support suggests its affiliation with members of the *B. subtilis* group. (See Hossain et al., Frontiers Plant Science 2015, FIG. 1A). A gyrB gene based phylogenetic tree constructed using Maximum Likelihood (ML) methods was also concordant with the phylogeny constructed using Neighbor-Joining methods (data not shown). In addition to the gyrB-based phylogeny, we constructed a phylogenomic tree using 729,383 bp of core genome sequences present within the genome of 25 *B. subtilis* group isolates to provide a more refined phylogenetic placement of PGPR strains. The topology and allocation of strains to clades in the gyrB phylogeny was similar to the phylogenomic tree (See Hossain et al., Frontiers Plant Science 2015, FIG. 1B). One notable difference is that the topology of the tree regarding the position of strain *B. siamensis* KCTC13613 differs significantly between the gyrB-based tree and the phylogenomic tree, with the gyrB based phylogeny placing KCTC13613 in a separate Glade whereas the phylogenomic tree included it within a monophyletic group that includes strains of *B. amyloliquefaciens* subsp. *plantarum* (now *B. velezensis*).

BLAST matrix. Genome wide proteome comparisons of 13 PGPR *Bacillus* strains using an all-against-all BLASTp approach demonstrated that PGPR *Bacillus* spp. strains are highly diverse, as indicated by gene family similarity between PGPR *Bacillus* spp. genomes ranging from 32-90% (data not shown). Consistent with the phylogenetic analysis, high similarity was found among strains AP71, AP79, AP193, AB01, GB03, and FZB42, with proteomic similarity ranging from 70-90%.

Core-genome analysis. Analysis of genome sequence alignment using progressive Mauve determined that the core genome of 13 PGPR *Bacillus* spp. strains contains 1,407,980 bp of genomic DNA which encode 1,454 ORFs (data not shown). Comparison of core genome sequences of the genus *Bacillus*, subgroup *B. subtilis*, species *B. amyloliquefaciens*, and subspecies *plantarum* (now *B. velezensis*) demonstrated that as the number of genomes increases, the number of different subsystems within each respective core genome decreases. (See Hossain et al., Frontiers Plant Science 2015, FIG. 2A-D). The highest numbers of subsystems in each of the core genome categories, except for the genus *Bacillus* core genome, was devoted to carbohydrate metabolism. These findings suggest that strains from the genus *Bacillus* use diverse carbon sources. In addition, the core genome for the genus *Bacillus* has more subsystems devoted to RNA, DNA, and protein metabolism compared to carbohydrate metabolism. (See Hossain et al., Frontiers Plant Science 2015, FIG. 2A-D).

The genome alignment from 28 different subsp. *plantarum* (now *B. velezensis*) strains, including six subsp. *plantarum* (now *B. velezensis*) strains sequenced in this Example, identified 2,550,854 bp of core genome sequence that is predicted to encode 2,839 ORFs. The genome alignment of 32 *B. amyloliquefaciens* strains, including 28 subsp. *plantarum* (now *B. velezensis*) strains, identified 2,418,042 bp of core genome sequence predicted to encode 2,773 ORFs.

The genome alignment of 53 strains of *B. subtilis* group, including the 12 strains sequenced in this Example, identified 578,872 bp of core genome sequence predicted to encode 674 ORFs. The number of protein coding genes present within the genome of *Bacillus* spp. (~4,000) and the low number of ORFs (674) encoded by their core genomes suggests a large amount of genomic plasticity among *Bacillus* genomes that experience frequent gene acquisitions and losses. It was observed that the *B. amyloliquefaciens* core genome was devoid of mobile genetic elements, such as prophages, transposable elements, and plasmids (data not shown). Furthermore, the *B. subtilis* core genome was also devoid of genes or genetic clusters linked with iron acquisition and metabolism, secondary metabolite biosynthesis, signal transduction and phosphorus metabolism. (See Hossain et al., Frontiers Plant Science 2015, FIG. 2A-D).

In this Example, the genus *Bacillus* core genome was also determined by analyzing all complete genome sequences from the genus *Bacillus* currently available in GenBank. We determined that the genus *Bacillus* contains 194,686 bp of core sequence predicted to encode 201 different ORFs. The predicted functions present in all *Bacillus* strains are limited to the following subsystem features: cofactor synthesis, vitamin synthesis, prosthetic groups and pigments biogenesis, cell wall and capsule biogenesis, membrane transport, RNA metabolism, nucleoside metabolism, protein metabolism, regulation and cell signaling, DNA metabolism, respiration, amino acids and derivatives, sulfur metabolism, and carbohydrate utilization Comparative Analysis of Core Genes Uniquely Present in *B. amyloliquefaciens* Subsp. *Plantarum* (Now *B. velezensis*).

Comparison of PGPR-specific genomes with that of non-PGPR *B. subtilis* subsp. *subtilis* str. 168 did not identify any genes other than essential housekeeping genes that were conserved within the genomes of PGPR strains (data not shown). Comparative analysis of core genomes from 28 *B. amyloliquefaciens* subsp. *plantarum* (now *B. velezensis*) and 32 *B. amyloliquefaciens* species identified 193,952 bp of sequences that are present within the subsp. *plantarum* (now *B. velezensis*) core genome but absent in the *B. amyloliquefaciens* core genome. Among these genetic loci there were 73 genes shared by all 28 *plantarum* (now *B. velezensis*) strains but were not present in any strains of subsp. *amyloliquefaciens*. The putative functions of these genes includes transportation (7 genes), regulation (7 genes), signaling (1 gene), carbon degradation (10 genes), synthesis of secondary metabolites (19 genes), and hypothetical proteins (12 genes). (See Hossain et al., Frontiers Plant Science 2015, FIG. 2D). Some of these gene products may be involved in interactions with plants and rhizosphere competence of subsp. *plantarum* (now *B. velezensis*) strains (e.g., pectin utilization). For instance, genes required for uptake and use of D-galacturonate and D-glucuronate are shared among genomes of *B. amyloliquefaciens* subsp. *plantarum* (now *B. velezensis*) strains. These include uxuA (mannonate dehydratase (EC 4.2.1.8)), kdgA (4-hydroxy-2-oxoglutarate aldolase (EC 4.1.3.16)), kdgK (2-dehydro-3-deoxygluconate kinase (EC 2.7.1.45)), exuT (hexuronate transporter), exuR (hexuronate utilization operon transcriptional repressor), and uxuB (D-mannonate oxidoreductase (EC 1.1.1.57)). In addition, genes required for biosynthesis of the polyketides difficidin and macrolactin were consistently found in PGPR subsp. *plantarum* (now *B. velezensis*) strains, suggesting their relevance in the biocontrol activities of these strains.

Gene Clusters Encoding Secondary Metabolite Biosynthesis and Natural Competency in Strain AP193.

Due to our observations of beneficial interactions between PGPR strain AP193 and both plant and animal hosts (Ran et al., 2012), we selected this strain for more intensive genome analysis. Assembly of strain AP193 genome sequences de novo resulted in 152 contigs larger than 1 kb, with a combined length of 4,121,826 bp. Analysis of AP193 contig sequences, using the antiSMASH secondary metabolite prediction program, suggests that gene clusters were present that are responsible for synthesis of three different polyketides: bacillaene, macrolactin and difficidin. In order to provide complete sequences for these biosynthesis pathways, the gaps between contigs 5 and 6, contigs 33 and 38, as well as contigs 27 and 28 were filled using PCR, followed by DNA sequencing. Each of the gene clusters in AP193 are collinear to their counterparts in *B. amyloliquefaciens* (now *B. velezensis*) FZB42; a naturally competent plant root-colonizing *B. amyloliquefaciens* (now *B. velezensis*) isolate with the ability to promote plant growth and suppress plant pathogens (Chen et al., 2007a). The percent amino acid identities of the proteins encoded by those clusters were within the range of 98-100% when compared with those of FZB42. Secondary metabolite biosynthesis gene clusters involved in non-ribosomal synthesis of cyclic lipopeptides surfactins, fengycin and bacillomycin D and of the antimicrobial dipeptide bacilysin present in FZB42 were also detected in the AP193 genome. The percent amino acid identities of the AP193 proteins encoded on those clusters to the FZB42 homologs ranged from 98% to 100%. The lack of natural competency of the PGPR strain AP193 prompted us to determine the presence of competence-related genes within this strain. We searched the AP193 genome sequences for the presence of competence related genes found within the genome of FZB42, and observed that all of the genes required for encoding the structural components of the competence system found in strain FZB42 are present within the genome of AP193 with 98 to 100% identity (data not shown); however, genes comQ, comX, and comP are involved in regulating quorum-sensing in *B. amyloliquefaciens* (now *B. velezensis*) FZB42 (Chen et al., 2007a) were absent within the genome of strain AP193 (data not shown). The absence of comQ, comX, and comP may be responsible for the lack of natural competency for strain AP193.

AP193 Secondary Metabolites Inhibit the Growth of Multiple Bacterial Plant Pathogens In Vitro.

Antimicrobial activities of strain AP193 and its mutants AP193ΔdfnD (deficient in the production of difficidin), AP193ΔsrfAA (deficient in surfactin production), and AP193Δsfp (unable to produce polyketide or lipopepetide due to a deletion of sfp gene encoding 4'-phosphopantetheinyl transferase) were tested against plant pathogens *Pseudomonas syringe* pv. *tabaci, Rhizobium radiobacter, Xanthomonas axonopodis* pv. *vesicatoria,* and *Xanthomonas axonopodis* pv. *campestris*. The AP193 wild type strain demonstrated strong antimicrobial activity, whereas the AP193Δsfp mutant was devoid of an inhibitory effect against those plant pathogens. (See Hossain et al., Frontiers Plant Science 2015, FIG. 3), underlining the contribution of lipopeptides and/or polyketides in the bioactivity of AP193. This also indicates that the dipeptide bacilysin, whose synthesis is independent of Sfp, was not involved in antagonistic activity expressed in vitro. The AP193ΔsrfAA mutant conferred antimicrobial activity similar to wild-type to P. syringe pv. *tabaci, R. radiobacter, X. axonopodis* pv. *vesicatoria,* and *X. axonopodis* pv. *Campestris* (see Hossain et al., Frontiers Plant Science 2015, FIG. 3), suggesting that surfactin has no putative role in the antibacterial activity of AP193 against those plant pathogens under the conditions tested in this Example. These findings also demonstrated that surfactin neither influences the antimicrobial compound biosynthesis in AP193 nor does it inhibit antibacterial activities of the antibacterial compounds produced by AP193. Difficidin acts as the major antibiotic in antagonism of AP193 against plant pathogens P. syringe pv. *tabaci, R. radiobacter, X. axonopodis* pv. *vesicatoria,* and *X. axonopodis* pv. *campestris* as indicated by the lack of the inhibitory effect of the AP193ΔdfnD mutant against those plant pathogens. (See Hossain et al., Frontiers Plant Science 2015, FIG. 4).

We further confirmed that the AP193ΔdfnD and Δsfp mutants lacked synthesis of difficidin by conducting LC-MS analysis of the cell-free TSB culture supernatants from wild-type AP193 and each of these mutants. As reported previously, only the deprotonated form of oxydifficidin was detectable in bacterial supernatants using MS in the negative mode ($[M-H]^-=559.3$) (Chen et al., 2006), with a molecular mass of 559.3 detected in supernatants of the wild-type AP193 culture but not observed from the culture of the ΔdfnD mutant. (See Hossain et al., Frontiers Plant Science 2015, FIG. 4) or from the Δsfp mutant (data not shown). The ΔsrfAA mutant exhibited difficidin synthesis as in the wild-type AP193 culture (data not shown). These findings demonstrate the importance of difficidin in the biocontrol activity of subsp. *plantarum* (now *B. velezensis*) strains against plant pathogens.

Strain AP193 Secondary Metabolites Control Bacterial Spot Caused by *X. axonopodis* pv. Vesicatoria in Tomato Plants.

To determine the role of bioactive compounds produced by strain AP193 in providing protection against plant diseases, the AP193 wild-type strain and its AP193ΔdfnD, AP193Δsfp and AP193ΔsrfAA mutants were applied to tomato plants several days before those plants were subsequently inoculated with plant pathogen *X. axonopodis* pv. vesicatoria. Both AP193 wild-type and AP193ΔsrfAA significantly ($P<0.05$) reduced disease severity of bacterial spot on tomato plants compared to the disease control (Table 3). Additionally, the application of strain AP193 significantly increased the root dry weight of the plants (Table 3). Unlike AP193 wild-type and its AP193ΔsrfAA mutant, strains AP193Δsfp and AP193ΔdfnD neither protected tomato plants from severe bacterial spot caused by *X. axonopodis* pv. vesicatoria nor improved plant growth (Table 3), further supporting the importance of difficidin for plant disease protection. These findings are in agreement with the in vitro antibiosis pattern of AP193 wild-type strain and its AP193ΔdfnD, AP193Δsfp and AP193ΔsrfAA mutants demonstrated against plant pathogen *X. axonopodis* pv. vesicatoria.

Discussion

PGPR *Bacillus* spp. strains are used worldwide to improve crop yields and to protect against plant diseases. In this Example, 12 PGPR genomes were sequenced, including *B. subtilis, B. pumilus, B. amyloliquefaciens* (now *B. velezensis*), *B. mojavensis, B. siamensis, B. sonorensis,* and *B. tequilensis*. These data were analyzed using ANI, gyrB-based phylogenies and core genome-based phylogenies to resolve taxonomic affiliation of *Bacillus* spp. strains. Our findings demonstrate that half of the strains sequenced in this Example are affiliated with *B. amyloliquefaciens* subsp. *plantarum* (now *B. velezensis*), including strain GB03 that was formerly designated as *B. subtilis*. Previously, *B. siamensis* type strain KCTC 13613T was proposed as a novel species (Sumpavapol et al., 2010), but a *Bacillus* core genome-based phylogenomic analysis. (See Hossain et al., Frontiers Plant Science 2015, FIG. 1) revealed that *B. siamensis* KCTC 13613T is instead affiliated with *B. amyloliquefaciens* subsp. *plantarum* (now *B. velezensis*). This finding supports the results of Jeong et al (Jeong et al., 2012) that determined the close affiliation of *B. siamensis* type strain KCTC 13613T to *B. amyloliquefaciens* subsp. *plantarum* (now *B. velezensis*) based on ANI. These findings also support the continued use of core genome-based phylogenomic approaches to provide better phylogenetic resolution than analyses that use a single housekeeping gene (e.g., gyrB). Phylogenies based on gyrB and core genome sequences demonstrate that *B. amyloliquefaciens* subsp. *plantarum* (now *B. velezensis*) are highly similar, but comparison of their proteomes demonstrates that they are closely related, yet distinct, and may exert plant growth-promoting activities through different mechanisms.

*B. amyloliquefaciens* subsp. *plantarum* (now *B. velezensis*) strain AB01 was isolated from the intestine of channel catfish (Ran et al., 2012), but its affiliation with plant-associated strains may suggest transient presence within a fish gastrointestinal tract; however, given that the fish feed is soy-based it is likely that the plant-based diet was also a factor in the growth of this strain within a fish intestine. Similarly, *B. siamensis* type strain KCTC 13613T was found to be closely affiliated with *B. amyloliquefaciens* subsp. *plantarum* (now *B. velezensis*) and was isolated from salted crab, rather than a plant-associated source. The efficacy of strains AB01, AP193, and other plant-associated strains as probiotics in fish shows the capacity for biocontrol of animal and plant pathogens as well as an overlap in host colonization (Ran et al., 2012).

With rapid advances in sequencing technologies it is now possible to extend genomic analysis beyond individual genomes to analyze core genomes (Medini et al., 2008). In this Example, core genomic analyses were conducted on PGPR strains from species affiliated with the *B. subtilis* group. This analysis identified 73 genes exclusively present among all subsp. *plantarum* (now *B. velezensis*) that are absent in subsp. *amyloliquefaciens* strains. This small number of subsp. *plantarum* (now *B. velezensis*)-specific genes agrees with a previous report that identified 130 subsp. *plantarum* (now *B. velezensis*)-specific genes using a limited number of genome sequences from subsp. *plantarum* (now *B. velezensis*) strains (He et al., 2012). Of these 73 *plantarum* (now *B. velezensis*)-specific genes identified in this Example, many are predicted to be important for plant-associated and soil-associated functions. For example, genes that are required for the use of D-galacturonate and D-glucuronate were found in the pool of *B. amyloliquefaciens* subsp. *plantarum* (now *B. velezensis*)-specific core genes. This observation is consistent with the absence of these genes in the genome of *B. amyloliquefaciens* subsp. *amyloliquefaciens* (now *B. velezensis*) DSM7 (Ruckert et al., 2011), a strain without any reported PGPR activity. Pectin, a complex polymer found in plant tissues, is broken down to D-glucuronate and D-galacturonate which then serves as a carbon source for bacterial growth (Nemoz et al., 1976). This pectin could potentially serve as a nutrient source for efficient root colonization of PGPR through competitive nutrient uptake. Therefore, the presence of genes that enable D-galacturonate and D-glucuronate utilization could be advantageous for *B. amyloliquefaciens* subsp. *plantarum* (now *B. velezensis*) for plant growth-promoting activity through efficient root colonization.

Since many of the PGPR strains are from the *B. subtilis* group, the core genome estimation was expanded to include a larger number of *B. subtilis* strains. Increasing the number of *Bacillus subtilis* genomes analyzed to 53 resulted in a 579,166 bp core genome that is predicted to encode 674 ORFs. This smaller number of predicted genes reflects genomic diversity among the *B. subtilis* group. This finding demonstrates that the number of ORFs found in the *B. subtilis* group core genome is close to the number of *B. subtilis* ORFs that are considered as indispensable for growth in complex media (610 ORFs) (http://www.minibacillus.org/project#genes).

To validate a gene's involvement in plant-related processes, it is essential to construct isogenic mutants that are devoid of those genes. Therefore, we deleted genes from PGPR strain AP193 to evaluate the role of secondary metabolite biosynthesis gene clusters in the biological control of plant pathogens. To do this, a methylated shuttle vector pNZT1 (Zakataeva et al., 2010) with gene deletion constructs delivered targeted genetic modifications to AP193, demonstrating the efficacy of in vitro methylation of plasmids by cell-free extract in circumventing a restriction system that was presumed to have prevented transformation through electroporation.

Difficidin is a highly unsaturated 22-membered macrocylic polyene lactone phosphate ester with broad-spectrum antibacterial activity (Zimmerman et al., 1987). Difficidin expressed by strain FZB42, together with the dipeptide bacilysin, are antagonistic against *Erwinia amylovora*—the causative agent of fire blight disease in orchard trees (Chen et al., 2009). This Example using an isogenic mutant API 93ΔdfnD demonstrated for the first time that difficidin solely, not in conjunction with any other polyketides or dipeptides, exerts in vitro antibacterial activity against plant pathogens, such as *Pseudomonas syringe* pv. *tabaci*, *Rhizobium radiobacter*, *Xanthomonas axonopodis* pv. *vesicatoria* and *Xanthomonas axonopodis* pv. *campestris*. We also demonstrated, by using isogenic mutant AP193ΔdfnD, that difficidin expression is responsible for control of bacterial spot disease in tomato plants caused by *X. axonopodis* pv. *vesicatoria*. Taken together, these findings demonstrate that difficidin is the most important strain AP193 secondary metabolite for biological control of plant diseases due to bacterial pathogens. In addition, the construction of the sfp gene deletion allowed investigation of multiple secondary metabolites produced by AP193 and their individual contributions to biocontrol activity. The sfp deletion mutant lost antagonistic activity against each pathogen that was susceptible to the AP193 wild-type strain. Mutants with the sfp deletion are expected to lose the ability to synthesize difficidin in addition to other metabolites. Because the lack of antimicrobial activity of AP193Asfp is consistent with that of the AP193ΔdfnD mutant, this therefore suggests that difficidin is the primary metabolite responsible for in vitro inhibition of bacterial pathogens. In contrast, the surfactin mutant retained antimicrobial activity against all plant pathogens tested, demonstrating that surfactin is neither critical for in vitro antibiotic activity nor influences the synthesis or secretion of other secondary metabolite biosynthesis in this *Bacillus* spp. strain; however, surfactin may influence plant growth promoting activity since it has been observed that surfactin of *B. subtilis* elicits ISR in plants (Ongena et al., 2007) and is expressed in the plant cells colonized by FZB42 (Fan et al., 2011).

By studying the contributions of genetic loci that are conserved among top-performing PGPR strains we continue to uncover the relative contributions of genes in plant colonization, growth promotion, and/or pathogen biocontrol. In particular, future investigation of genes related to the uptake and use of pectin-derived sugars will help determine the relative importance of these genes for colonization of plants and persistence within this microbiome. Comparative genomic analysis of *Bacillus* spp. PGPR strains has led to a better understanding of gene products and provides a foundation to develop application strategies that result in greater plant growth promotion and biocontrol activity.

Tables

TABLE 1

Bacterial strains and plasmids used in this Example.

| Strains or plasmids | Relevant characteristics | Source or reference |
|---|---|---|
| *E. coli* K12 ER2925 | dcm-6 dam13::Tn9 | New England Biolabs |
| *B. amyloliquefaciens* subsp. *plantarum* strain AP193 | Wild type | Dr. Joseph Kloepper (Department of Entomology and Plant Pathology, Auburn University) |
| AP193Δsfp | deficient in lipopeptides and polyketides | This study |
| AP193ΔsrfAA | deficient in surfactin production | This study |
| AP193ΔdfnD | deficient in difficidin production | This study |
| *Bacillus amyloliquefaciens* FZB42 | Wild type | (Chen et al., 2007b) |
| pMK4 | *E. coli*-*Bacillus* shuttle plasmid, rolling circle replicative, Cm$^R$ | BGSC |
| pNZT1 | Replication thermosensitive derivative of the rolling-circle plasmid pWV01 (pG$^+$ replicon, Em$^R$) | Xiaozhou Zhang, Virginia Tech |
| pNZ-sfp | pNZT1 with upstream and downstream sequences of gene sfp | This study |
| pNZ-srf | pNZT1 with knock-out construct of srfAA | This study |
| pNZ-dif | pNZT1 with knock-out construct of dfnD | This study |

TABLE 2

Summary of draft genomes of Bacillus species sequenced used in this Example

| Isolates | Number of Contigs (>1 kb) | Size (total bp in assembly) | % G + C | NCBI BioProject Number | NCBI Short Read Archive Accession No. | Approx. sequence coverage (x) | Number of predicted ORFs |
|---|---|---|---|---|---|---|---|
| AB01 | 20 | 3,903,296 | 46.4 | PRJNA239317 | SRX475739 | 44 | 3944 |
| AP71 | 198 | 4,278,192 | 45.7 | PRJNA239317 | SRX475740 | 15 | 4531 |
| AP79 | 47 | 4,236,770 | 45.8 | PRJNA239317 | SRX475741 | 31 | 4368 |
| AP143 | 146 | 2,956,670 | 46.6 | PRJNA239317 | SRX475742 | 24 | 3324 |
| AP193 | 152 | 4,121,826 | 46.3 | PRJNA239317 | SRX475807 | 37 | 4159 |
| AP254 | 59 | 4,048,419 | 43.8 | PRJNA239317 | SRX475808 | 29 | 4717 |
| GB03 | 26 | 3,849,547 | 46.5 | PRJNA227787 | SRX380920 | 560 | 3928 |
| INR7 | 44 | 3,681,709 | 41.3 | PRJNA227786 | SRX447924 | 750 | 3857 |
| KCTC 3706T | 17 | 3,935,582 | 43.7 | PRJNA227789 | SRX447926 | 895 | 4140 |
| KCTC 13613T | 23 | 3,779,696 | 46.3 | PRJNA161489 | SRX450083 | 500 | 3915 |
| KCTC 13918T | 32 | 4,428,962 | 45.5 | PRJNA227788 | SRX450084 | 1000 | 4704 |
| KCTC 13622T | 33 | 3,981,302 | 43.9 | PRJNA227791 | SRX450086 | 1000 | 4299 |

TABLE 3

Effects of plant growth-promoting rhizobacteria (PGPR) strains on severity of bacterial spot disease and plant growth

| Strain [ab] | Disease severity [c] | Shoot Dry Weight (g) | Root Dry Weight (g) |
|---|---|---|---|
| Disease Control | 2.11 [a] | 2.07 [bc] | 0.378 [c] |
| AP193 | 1.30 [b] | 2.18 [b] | 0.453 [a] |
| AP193ΔsrfAA | 1.48 [b] | 2.16 [b] | 0.423 [abc] |
| AP193Δsfp | 2.31 [a] | 2.18 [b] | 0.405 [abc] |
| AP193Δdif | 2.06 [a] | 2.00 [c] | 0.389 [bc] |
| Healthy Control | 0.00 [c] | 2.38 [a] | 0.435 [ab] |
| LSD | 0.35 | 0.15 | 0.050 |

Note:
[a] The experimental design was a randomized complete block with ten replications per treatment. The experiment was conducted twice. Values followed by the same letter were not significantly different (P = 0.05) according to Fischer's protected LSD.
[b] One plant was in each replication. Plants were sprayed with PGPR suspension ($10^6$ CFU/ml) one week after transplanting, and were challenge-inoculated with pathogen solutions ($10^7$ CFU/ml) three days after inoculating PGPR.
[c] Disease severity ratings and harvest were done 14 days later. For disease severity rating, four compound leafs were selected from the bottom of each plant. The disease severity of each of the compound leaves was determined by rating the disease severity of each leaflet and calculating the average rating for the compound leaf. The leaflet was rated using a 0-4 rating scale, where 0 = healthy leaflet, 1 = <20% necrotic area of the leaflet, 2 = 20-50% necrotic area of the leaflet, 3 = 51-80% necrotic area of the leaflet, 4 = 80-100% necrotic area of the leaflet, or fully dead leaflet.

REFERENCES

Alegre, M. T., Rodriguez, M. C., and Mesas, J. M. (2004). Transformation of Lactobacillus plantarum by electroporation with in vitro modified plasmid DNA. FEMS Microbial Lett 241, 73-77. doi: 10.1016/j.femsle.2004.10.006.

Aziz, R. K., Bartels, D., Best, A. A., Dejongh, M., Disz, T., Edwards, R. A., Formsma, K., Gerdes, S., Glass, E. M., Kubal, M., Meyer, F., Olsen, G. J., Olson, R., Osterman, A. L., Overbeek, R. A., Mcneil, L. K., Paarmann, D., Paczian, T., Parrello, B., Pusch, G. D., Reich, C., Stevens, R., Vassieva, O., Vonstein, V., Wilke, A., and Zagnitko, O. (2008). The RAST server: Rapid annotations using subsystems technology. BMC Genomics 9:75. doi: Artn 75 Doi 10.1186/1471-2164-9-75.

Blin, K., Medema, M. H., Kazempour, D., Fischbach, M. A., Breitling, R., Takano, E., and Weber, T. (2013). antiSMASH 2.0—a versatile platform for genome mining of secondary metabolite producers. Nucleic Acids Res 41, W204-W212. doi: 10.1093/nar/gkt449.

Borriss, R., Chen, X. H., Rueckert, C., Blom, J., Becker, A., Baumgarth, B., Fan, B., Pukall, R., Schumann, P., Sproer, C., Junge, H., Vater, J., Puhler, A., and Klenk, H. P. (2011). Relationship of Bacillus amyloliquefaciens clades associated with strains DSM 7T and FZB42T: a proposal for Bacillus amyloliquefaciens subsp. amyloliquefaciens subsp. nov. and Bacillus amyloliquefaciens subsp. plantarum subsp. nov. based on complete genome sequence comparisons. Int J Syst Evol Microbiol 61, 1786-1801. doi: 10.1099/ijs.0.023267-0.

Chen, X. H., Koumoutsi, A., Scholz, R., Eisenreich, A., Schneider, K., Heinemeyer, I., Morgenstern, B., Voss, B., Hess, W. R., Reva, O., Junge, H., Voigt, B., Jungblut, P. R., Vater, J., Sussmuth, R., Liesegang, H., Strittmatter, A., Gottschalk, G., and Borriss, R. (2007a). Comparative analysis of the complete genome sequence of the plant growth-promoting bacterium Bacillus amyloliquefaciens FZB42. Nat Biotechnol 25, 1007-1014. doi: 10.1038/nbt1325.

Chen, X. H., Koumoutsi, A., Scholz, R., Eisenreich, A., Schneider, K., Heinemeyer, I., Morgenstern, B., Voss, B., Hess, W. R., Reva, O., Junge, H., Voigt, B., Jungblut, P. R., Vater, J., Sussmuth, R., Liesegang, H., Strittmatter, A., Gottschalk, G., and Borriss, R. (2007b). Comparative analysis of the complete genome sequence of the plant growth-promoting bacterium Bacillus amyloliquefaciens FZB42. Nat. Biotechnol. 25, 1007-1014. doi: 10.1038/nbt1325.

Chen, X. H., Scholz, R., Borriss, M., Junge, H., Mogel, G., Kunz, S., and Borriss, R. (2009). Difficidin and bacilysin produced by plant-associated Bacillus amyloliquefaciens are efficient in controlling fire blight disease. J Biotechnol 140, 38-44. doi: 10.1016/j/jbiotec.2008.10.015.

Chen, X. H., Vater, J., Piel, J., Franke, P., Scholz, R., Schneider, K., Koumoutsi, A., Hitzeroth, G., Grammel, N., Strittmatter, A. W., Gottschalk, G., Sussmuth, R. D., and Borriss, R. (2006). Structural and functional characterization of three polyketide synthase gene clusters in Bacillus amyloliquefaciens FZB 42. J Bacteriol 188, 4024-4036. doi: 10.1128/JB.00052-06.

Chin, A., F., W. T., Bloemberg, G. V., Mulders, I. H., Dekkers, L. C., and Lugtenberg, B. J. (2000). Root colonization by phenazine-1-carboxamide-producing bacterium Pseudomonas chlororaphis PCL1391 is essential for biocontrol of tomato foot and root rot. Mol Plant Microbe Interact 13, 1340-1345.

Choi, S. K., Jeong, H., Kloepper, J. W., and Ryu, C. M. (2014). Genome Sequence of *Bacillus amyloliquefaciens* GB03, an Active Ingredient of the First Commercial Biological Control Product. *Genome Announc* 2, 01092-01014.

Darling, A. C., Mau, B., Blattner, F. R., and Perna, N. T. (2004). Mauve: multiple alignment of conserved genomic sequence with rearrangements. *Genome Res* 14, 1394-1403. doi: 10.1101/gr.2289704.

Dekkers, L. C., Mulders, I. H., Phoelich, C. C., Chin, A. W. T. F., Wijfjes, A. H., and Lugtenberg, B. J. (2000). The sss colonization gene of the tomato-*Fusarium oxysporum* f. sp. *radicis-lycopersici* biocontrol strain *Pseudomonas fluorescens* WCS365 can improve root colonization of other wild-type *pseudomonas* spp. bacteria. *Mol Plant Microbe Interact* 13, 1177-1183. doi: 10.1094/MPMI.2000.13.11.1177.

Dietel, K., Beator, B., Budiharjo, A., Fan, B., and Borriss, R. (2013). Bacterial Traits Involved in Colonization of *Arabidopsis thaliana* Roots by *Bacillus amyloliquefaciens* FZB42. *Plant Pathol J* 29, 59-66.

Emmert, E. a. B., Klimowicz, A. K., Thomas, M. G., and Handelsman, J. (2004). Genetics of Zwittermicin A Production by *Bacillus cereus*. *Appl Environ Microbiol* 70, 104-113. doi: 10.1128/aem.70.1.104-113.2004.

Fan, B., Chen, X. H., Budiharjo, A., Bleiss, W., Vater, J., and Borriss, R. (2011). Efficient colonization of plant roots by the plant growth promoting bacterium *Bacillus amyloliquefaciens* FZB42, engineered to express green fluorescent protein. *J Biotechnol* 151, 303-311. doi: 10.1016/j.jbiotec.2010.12.022.

Felsenstein, J. (1981). Evolutionary trees from DNA sequences: a maximum likelihood approach. *J Mol Evol* 17, 368-376.

Friis, C., Wassenaar, T. M., Javed, M. A., Snipen, L., Lagesen, K., Hallin, P. F., Newell, D. G., Toszeghy, M., Ridley, A., Manning, G., and Ussery, D. W. (2010). Genomic characterization of *Campylobacter jejuni* strain M1. *PLoS One* 5, e12253. doi: 10.1371/journal.pone.0012253.

Goris, J., Konstantinidis, K. T., Klappenbach, J. A., Coenye, T., Vandamme, P., and Tiedje, J. M. (2007). DNA-DNA hybridization values and their relationship to whole-genome sequence similarities. *Int J Syst Evol Microbiol* 57, 81-91.

Hao, K., He, P., Blom, J., Rueckert, C., Mao, Z., Wu, Y., He, Y., and Borriss, R. (2012). The genome of plant growth-promoting *Bacillus amyloliquefaciens* subsp. *plantarum* strain YAU B9601-Y2 contains a gene cluster for mersacidin synthesis. *J Bacteriol* 194, 3264-3265. doi: 10.1128/JB.00545-12.

He, P., Hao, K., Blom, J., Ruckert, C., Vater, J., Mao, Z., Wu, Y., Hou, M., He, P., He, Y., and Borriss, R. (2012). Genome sequence of the plant growth promoting strain *Bacillus amyloliquefaciens* subsp. *plantarum* B9601-Y2 and expression of mersacidin and other secondary metabolites. *J Biotechnol* 164, 281-291.

Horton, R. M., Hunt, H. D., Ho, S. N., Pullen, J. K., and Pease, L. R. (1989). Engineering hybrid genes without the use of restriction enzymes: gene splicing by overlap extension. *Gene* 77, 61-68.

Hossain, M. J., Waldbieser, G. C., Sun, D., Capps, N. K., Hemstreet, W. B., Carlisle, K., Griffin, M. J., Khoo, L., Goodwin, A. E., Sonstegard, T. S., Schroeder, S., Hayden, K., Newton, J. C., Terhune, J. S., and Liles, M. R. (2013). Implication of lateral genetic transfer in the emergence of *Aeromonas hydrophila* isolates of epidemic outbreaks in channel catfish. *PLoS One* 8, e80943. doi: 10.1371/journal.pone.0080943.

Idriss, E. E., Makarewicz, O., Farouk, A., Rosner, K., Greiner, R., Bochow, H., Richter, T., and Borriss, R. (2002). Extracellular phytase activity of *Bacillus amyloliquefaciens* FZB45 contributes to its plant-growth-promoting effect. *Microbiology* 148, 2097-2109.

Jeong, H., Choi, S. K., Kloepper, J. W., and Ryu, C. M. (2014). Genome Sequence of the Plant Endophyte *Bacillus pumilus* INR7, Triggering Induced Systemic Resistance in Field Crops. *Genome Announc* 2, 01093-01014.

Jeong, H., Jeong, D.-E., Kim, S. H., Song, G. C., Park, S.-Y., Ryu, C.-M., Park, S.-H., and Choi, S.-K. (2012). Draft Genome Sequence of the Plant Growth-Promoting Bacterium *Bacillus siamensis* KCTC 13613T. *J Bacteriol* 194, 4148-4149. doi: 10.1128/jb.00805-12.

Kamilova, F., Validov, S., Azarova, T., Mulders, I., and Lugtenberg, B. (2005). Enrichment for enhanced competitive plant root tip colonizers selects for a new class of biocontrol bacteria. *Environ Microbiol* 7, 1809-1817.

Kim, B. K., Chung, J. H., Kim, S. Y., Jeong, H., Kang, S. G., Kwon, S. K., Lee, C. H., Song, J. Y., Yu, D. S., Ryu, C. M., and Kim, J. F. (2012). Genome sequence of the leaf-colonizing Bacterium *Bacillus* sp. strain 5B6, isolated from a cherry tree. *J Bacteriol* 194, 3758-3759. doi: 10.1128/JB.00682-12.

Kloepper, J. W., Ryu, C. M., and Zhang, S. (2004). Induced Systemic Resistance and Promotion of Plant Growth by *Bacillus* spp. *Phytopathology* 94, 1259-1266. doi: 10.1094/PHYTO.2004.94.11.1259.

Kloepper, J. W., and Schroth, M. N. (1978). Plant growth-promoting rhizobacteria on radishes. *Proceedings of the 4th International Conference on Plant Pathogenic Bacteria. Station de Pathologic Végétale et Phytobactériologie, INRA, Angers, France* 2, 879-882.

Kokalis-Burelle, N., Vavrina, C. S., Rosskopf, E. N., and Shelby, R. A. (2002). Field evaluation of plant growth-promoting Rhizobacteria amended transplant mixes and soil solarization for tomato and pepper production in Florida. *Plant and Soil* 238, 257-266.

Letunic, I., and Bork, P. (2011). Interactive Tree Of Life v2: online annotation and display of phylogenetic trees made easy. *Nucleic Acids Res* 39, W475-W478. doi: 10.1093/nar/gkr201.

Lugtenberg, B., and Kamilova, F. (2009). Plant-Growth-Promoting Rhizobacteria. *Annu Rev Microbiol* 63, 541-556. doi: doi:10.1146/annurev.micro.62.081307.162918.

Lukashin, A. V., and Borodovsky, M. (1998). GeneMark.hmm: new solutions for gene finding. *Nucleic Acids Res* 26, 1107-1115.

Medini, D., Serruto, D., Parkhill, J., Relman, D. A., Donati, C., Moxon, R., Falkow, S., and Rappuoli, R. (2008). Microbiology in the post-genomic era. *Nat Rev Microbiol* 6, 419-430. doi: 10.1038/nrmicro1901.

Nakkeeran, S., Fernando, W. G. D., and Siddiqui, Z. A. (2005). "Plant growth promoting rhizobacteria formulations and its scope in commercialization for the management of pests and diseases," in *PGPR: Biocontrol and Biofertilization*, ed. Z. A. Siddiqui. (Dordrecht, The Netherlands: Springer), 257-296.

Nemoz, G., Robert-Baudouy, J., and Stoeber, F. (1976). Physiological and genetic regulation of the aldohexuronate transport system in *Escherichia coli*. *J Bacteriol* 127, 706-718.

Ongena, M., Jourdan, E., Adam, A., Paquot, M., Brans, A., Joris, B., Arpigny, J. L., and Thonart, P. (2007). Surfactin and fengycin lipopeptides of *Bacillus subtilis* as elicitors of induced systemic resistance in plants. Environ Microbiol 9, 1084-1090. doi: 10.1111/j.1462-2920.2006.01202.x.

Pfeiffer, W., and Stamatakis, A. (2010). "Hybrid MPI/Pthreads Parallelization of the RAxML Phylogenetics Code. In: Ninth IEEE International Workshop on High Performance Computational Biology (HiCOMB 2010).". (Atlanta, USA).

Podile, A. R., and Kishore, G. K. (2006). "Plant growth-promoting rhizobacteria," in *Plant-Associated Bacteria*, ed. S. S. Gnanamanickam. (Netherlands: Springer), pp. 195-230.

Ran, C., Carrias, A., Williams, M. A., Capps, N., Dan, B. C., Newton, J. C., Kloepper, J. W., Ooi, E. L., Browdy, C. L., Terhune, J. S., and Liles, M. R. (2012). Identification of *Bacillus* strains for biological control of catfish pathogens. *PLoS One* 7, e45793. doi: 10.1371/journal.pone.0045793.

Reva, O. N., Dixelius, C., Meijer, J., and Priest, F. G. (2004). Taxonomic characterization and plant colonizing abilities of some bacteria related to *Bacillus amyloliquefaciens* and *Bacillus subtilis*. *FEMS Microbiol Ecol* 48, 249-259. doi: 10.1016/j.femsec.2004.02.003.

Richter, M., and Rosselló-Móra, R. (2009). Shifting the genomic gold standard for the prokaryotic species definition. *Proc Natl Acad Sci USA* 106, 19126-19131. doi: 10.1073/pnas.0906412106.

Ruckert, C., Blom, J., Chen, X., Reva, O., and Borriss, R. (2011). Genome sequence of *B. amyloliquefaciens* type strain DSM7(T) reveals differences to plant-associated *B. amyloliquefaciens* FZB42. *J Biotechnol* 155, 78-85. doi: 10.1016/j.jbiotec.2011.01.006.

Ryu, C.-M., Farag, M. A., Hu, C.-H., Reddy, M. S., Kloepper, J. W., and Paré, P. W. (2004). Bacterial Volatiles Induce Systemic Resistance in *Arabidopsis*. *Plant Physiol* 134, 1017-1026. doi: 10.1104/pp. 103.026583.

Saitou, N., and Nei, M. (1987). The neighbor-joining method: a new method for reconstructing phylogenetic trees. *Mol Biol Evo* 4, 406-425.

Sumpavapol, P., Tongyonk, L., Tanasupawat, S., Chokesajjawatee, N., Luxananil, P., and Visessanguan, W. (2010). *Bacillus siamensis* sp. nov., isolated from salted crab (poo-khem) in Thailand. *Int J Syst Evol Microbiol* 60, 2364-2370. doi: 10.1099/ijs.0.018879-0.

Tamura, K., Peterson, D., Peterson, N., Stecher, G., Nei, M., and Kumar, S. (2011). MEGA5: molecular evolutionary genetics analysis using maximum likelihood, evolutionary distance, and maximum parsimony methods. *Mol Biol Evo* 28, 2731-2739.

Xu, Z., Zhang, R., Wang, D., Qiu, M., Feng, H., Zhang, N., and Shen, Q. (2014). Enhanced control of cucumber wilt disease by *Bacillus amyloliquefaciens* SQR9 by altering the regulation of Its DegU phosphorylation. *Appl Environ Microbiol* 80, 2941-2950. doi: 10.1128/AEM.03943-13.

Yuan, J., Raza, W., Shen, Q., and Huang, Q. (2012). Antifungal Activity of *Bacillus amyloliquefaciens* NJN-6 Volatile Compounds against *Fusarium oxysporum* f. sp. *cubense*. *Appl Environ Microbiol* 78, 5942-5944. doi: 10.1128/aem.01357-12.

Zakataeva, N. P., Nikitina, O. V., Gronskiy, S. V., Romanenkov, D. V., and Livshits, V. A. (2010). A simple method to introduce marker-free genetic modifications into the chromosome of naturally nontransformable *Bacillus amyloliquefaciens* strains. *Appl Microbiol Biotechnol* 85, 1201-1209. doi: 10.1007/s00253-009-2276-1.

Zhang, G.-Q., Bao, P., Zhang, Y., Deng, A.-H., Chen, N., and Wen, T.-Y. (2011). Enhancing electro-transformation competency of recalcitrant *Bacillus amyloliquefaciens* by combining cell-wall weakening and cell-membrane fluidity disturbing. *Anal Biochem* 409, 130-137. doi: http://dx.doi.org/10.1016/j.ab.2010.10.013.

Zimmerman, S. B., Schwartz, C. D., Monaghan, R. L., Pelak, B. A., Weissberger, B., Gilfillan, E. C., Mochales, S., Hernandez, S., Currie, S. A., Tejera, E., and Et Al. (1987). Difficidin and oxydifficidin: novel broad spectrum antibacterial antibiotics produced by *Bacillus subtilis*. I. Production, taxonomy and antibacterial activity. *J Antibiot (Tokyo)* 40, 1677-1681.

Example 2—Efficiency of Pectin Supplement in Root Colonization and Plant Growth-Promotion of Soybean Plants by *Bacillus amyloliquefaciens* Subsp. *Plantarum* (Bap) (Now *B. velezensis* (bv))

Abstract

A second greenhouse experiment was conducted to determine the effects of pectin on root colonization, nodulation by indigenous soil *rhizobia*, and plant growth-promotion activity of *Bacillus amyloliquefaciens* subsp. *plantarum* (Bap) (now *Bacillus velezensis* (By)) rifR strains AP193 and AP143 on soybean. The overall hypothesis tested is that the complex carbohydrate pectin will enhance Bap (now Bv)-mediated plant growth promotion. The experimental design included soybean seeds planted in soil that contained Bap (now Bv) strains with or without 0.1% pectin supplement, along with a water control, and after 28 days the plants were harvested and analyzed for statistical significance. The data indicate that Bap (now Bv) rifR strains with pectin supplement enhanced soybean shoot and root length in greenhouse conditions. Dry shoot and root weights of Bap (now Bv) rifR strains with pectin supplement also increased, but were not significantly different compared to Bap (now Bv) rifR strains without pectin supplement. Bap (now Bv) rifR strains with pectin supplement increased significantly root nodulation of soybean. However, rhizobacterial populations recovered from the rhizosphere of soybean plant roots were not significantly different.

Materials and Methods

Preparation of Rhizobacterial Cells.

Plant growth-promoting rhizobacteria (PGPR) *Bacillus amyloliquefaciens* subsp. *plantarum* (Bap) now *Bacillus velezensis* (By)) strains AP193 and AP143 were selected based on their capacity for utilization of pectin as a C and energy source. *Bacillus thuringiensis* subsp. *kurstaki* (Btk) strain HD73 was collected from the USDA-ARS culture collection (Ames, Iowa) that was selected for inability to degrade and use pectin.

Three bacterial strains were cultured on TSA (BD Difco™ Agar, USA) with 50 µg/ml Rifampicin (Sigma, USA) from the cryo stocks (−80° C.) at 28° C. for 24 hours. A single colony of each strain was inoculated in 50 ml tubes containing 35 ml TSB with rifampicin (50 µg/ml) in tubes wrapped with aluminum foil to avoid light. Bacterial cultures were incubated for 48 hours with shaking at 220 rpm at 30° C. The bacterial cells were then spun down using Sorvall Legend RT centrifuge (The Thermo Scientific, USA) at 10,000×g for 10 minutes and the supernatant was discarded, and the pellet was washed with sterile water to remove the media. After the final wash, the supernatant was discarded and re-suspended in sterile Milli-Q water. The mid log phase bacterial suspension optical density was calculated at on optical density of 600 nm (OD600) using a GENE- SYS™ 10S UV-Vis Spectrophotometer (Thermo Scientific, USA). The OD600 of each rhizobacterial strain was serially diluted for calculated of colony-forming units (CFU) per milliliter. Suspensions were diluted to obtain 1×106 CFU/ml for inoculation of soybean seeds.

Soil Preparation and Pectin Mixture.

Field soil sieved to remove root debris was used for the greenhouse experiment. Soil (450 g) was placed in each cone-tainer tube (lightweight large Deepots D40L, Stuewe & Sons, Danville, Ill., USA) that contained three cotton balls in the bottom to retain soil. Pectin power (EC No. 232-553-0, Tokyo chemical industry co., Toshima, Kita-Ku, Tokyo, Japan) from citrus source was mixed thoroughly with field soil using soil mixing machine at a rate of 1 g per 1,000 g field soil.

Soybean Seed Inoculation and Plant Growth Measurement.

Soybean seed ('Asgrow 6702 RR') not treated with chemicals was used as in the previous experiment. One seed was placed in each cone-tainer, and 1 ml of 106 CFU was pipetted over each seed. Then, 5 g of soil was placed over each seed. Each cone-tainer rack was covered by plastic sheet to prevent soil desiccation for 48 hours. Afterwards, cone-tainer racks were transferred to the greenhouse chamber and tubes were watered twice daily.

After 28 days, all the plants were harvested for plant morphometric measurement. Shoot length was measured from the growing apical region to the basal region connected to the root. Root nodules were visually counted from all plants. The soil (approximately 448 g) was removed gently from the roots of each plant and placed in a 15 ml falcon tubes. Nine ml sterile water were added to each conical tube, and tubes were vortexed thoroughly. Then serial dilutions were made from 1:10 to 1:1000 in sterile Milli-Q water in microcentrifuge tubes and plated on TSA plates with rifampicin (50 µg/ml) for each dilution and incubated at 28° C. for 24 to 48 hours. Colonies that grew on the rif TSA plates were counted and expressed in log 10 CFU/ml. For root dry mass measurement, roots were washed to remove soil and dried in oven 45° C. After washing roots to remove all soil, roots and shoots were dried in an oven at 45° C. for dry weights. Root length was measured from the root apex to root-stem junction.

Experimental Design and Statistical Data Analysis.

Cone-tainers were arranged in a completely randomized design (RCD) with 8 treatments and with 12 replications, with each replication being a single plant in a single cone-tainer. The data of shoot height, root height, dry shoot weight, dry root weight, root nodules, and rhizobacterial growth were analyzed with SAS 9.4 software (SAS Institute, Cary, N.C.) using the proc GLIMMIX. Each treatment means was compared using LSMEANS at P=0.05 level of significance.

Results

The effects of Bap (now Bv) strains AP193 and AP143 on shoot length, root length, dry shoot weight, dry root weight, and root nodulation of soybean varied with pectin amendment are shown in Table 4. Each experimental control and treatment had 12 replicates, except for AP143 treatment which had 11 replicates due to lack of germination.

TABLE 4

Effect of pectin amendment on soybean growth, nodulation by indigenous rhizobia, and root colonization by Bap (now Bv) strains and Btk.

| Treatment | Plant growth metrics | | | | Mean no. of modulation by | |
|---|---|---|---|---|---|---|
| | Shoot length (cm) | Root length (cm) | Dry Shoot weight (g) | Dry Root weight (g) | indigenous soil rhizobia | Root colonization (Log CFU/g) |
| Water control | 28.71c | 18.58b | 0.33d | 0.07cd | 0 | 0 |
| Pectin control | 38.04b | 24.25a | 0.39bc | 0.07cd | 5.41ab | 2.4c |
| AP193W | 33.91b | 25.29a | 0.42bc | 0.10bc | 1.50bcd | 4.48a |
| AP193P | 46.37a | 26.41a | 0.64a | 0.15ab | 7.33a | 4.94a |
| AP143W | 36.80b | 22.89a | 0.45b | 0.16a | 2.16bc | 3.76b |
| AP143P | 43.12ab | 22.79ab | 0.59ab | 0.15ab | 9.33a | 4.10ab |
| HD73W | 30.37bc | 18.08b | 0.35cd | 0.06cd | 0.66cd | 2.03c |
| HD73P | 36.70b | 23.95a | 0.35cd | 0.06d | 0.91cd | 1.43c |

Bap$^x$ stain = AP193 & AP143; Btk$^y$ strain = HD73
Mean values from the greenhouse experiment with eight treatments and 12 replications. Mean value in the column followed by the same letter are not significantly different at P ≤ 0.05 using Tukey's multiple comparison tests.

The shoot length was significantly enhanced by pectin supplement and inoculation with Bap (now Bv) strain AP193 but not by Bap (now Bv) strain AP143 with pectin supplement. The mean shoot length of Bap (now Bv) strains AP193 and AP143 with pectin supplement were 46.40 cm and 43.10 cm. Shoot of Bap (now Bv) strain AP193 with pectin supplement was higher than Bap (now Bv) strain AP193 without pectin supplement. However, with Bap (now Bv) strain AP143 and pectin supplement, mean shoot length was slightly higher than treatment without pectin supplement. Mean root lengths of Bap (now Bv) strains AP193 and AP143 with pectin supplement were slightly higher but not significantly different compared to Bap (now Bv) strains AP193 and AP143 without pectin supplement.

Pectin amendment did not result in significantly higher shoot weights for treatment with either of the Bap (now Bv) strains. Dry shoot weight of Bap (now Bv) strain AP143 with pectin supplement were 0.59 g and not significantly different than Bap (now Bv) strain AP143 without pectin supplement. Soybean dry root weight of Bap (now Bv) stain AP193 with pectin supplement were 0.15 g and it was slightly higher than Bap (now Bv) strain AP193 without pectin supplement. There was no significant difference found between Bap (now Bv) strain AP193 with pectin supplement and Bap (now Bv) strain AP193 without pectin supplement.

Nodulation of soybean roots by native soil *rhizobia* (Table 4) were present with application of pectin put not in the control with no pectin and no PGPR strains. Root nodulation by indigenous *rhizobia* of Bap (now Bv) strains AP193 and AP143 with pectin supplement were significantly different than Bap (now Bv) strains AP193 and AP143 without pectin supplement. Mean root nodulation by native *rhizobia* of Bap (now Bv) strains AP193 and AP143 with pectin supplement were 7.33 and 9.33. Root nodulation were not observed in the water control treatment.

The effects of pectin supplement on root colonization by the inoculated Bap (now Bv) strains are shown in Table 4. The rhizosphere bacterial populations of Bap (now By) strain AP143 with pectin supplement were recovered within 24 hours after incubation at 28° C. Bap (now Bv) strain AP193 with pectin supplement was recovered within 36 hours after incubation at 28° C. The colony morphology of recovered Bap (now Bv) and Btk strains were alike to the applied Bap (now Bv) and Btk strains. Bap (now Bv) and Btk strains were observed in the pectin control but not the water control. With all three bacteria, supplementation with pectin did not significantly increased root colonization.

Discussion

The overall results of the greenhouse experiment support the hypothesis that pectin supplement enhances plant growth-promotion caused by Bap (now Bv) PGPR strains. In this study, greenhouse results showed that Bap (now Bv) strains with pectin supplement have the ability to enhance soybean plant growth by root colonization without causing damage on the roots, leaves, and shoots. The results (Table 4) showed that plant responses to pectin amendment with and without two Bap (now Bv) strains depended on the strain. For example, comparing effect on plants of Bap (now Bv) strain AP143 with and without pectin, there was no significant effect on shoot or root length and weights. Bap (now Bv) strain AP193, shoot length and root weight were significantly enhanced with pectin amendment, Comparing the effects of pectin amendments with and without Bap (now Bv) strains on nodulation by native soil *rhizobia*, Bap (now Bv) strain AP143 and pectin had enhanced nodulation compared to pectin alone, but with Bap (now Bv) strain AP193, there was no significant difference in nodulation with and without pectin.

Bap (now Bv) strains AP193 and AP143 soil amended with pectin enhanced soybean shoot and root growth in greenhouse conditions will be important to understanding how the concentration, source, and structure of pectin impacts the degradation and utilization by rhizobacteria to promote plant growth. Pectin composition in monocots (2-10%) and dicots (35%) vary widely due to plant primary cell wall structure (Ridley et al., 2001). Recent studies have found that 0.5% pectin increased biofilm formation on *Arabidopsis thaliana* by *Bacillus subtilis*, but little is known about its effect on plant growth (Beauregard et al., 2013).

Figure 3:
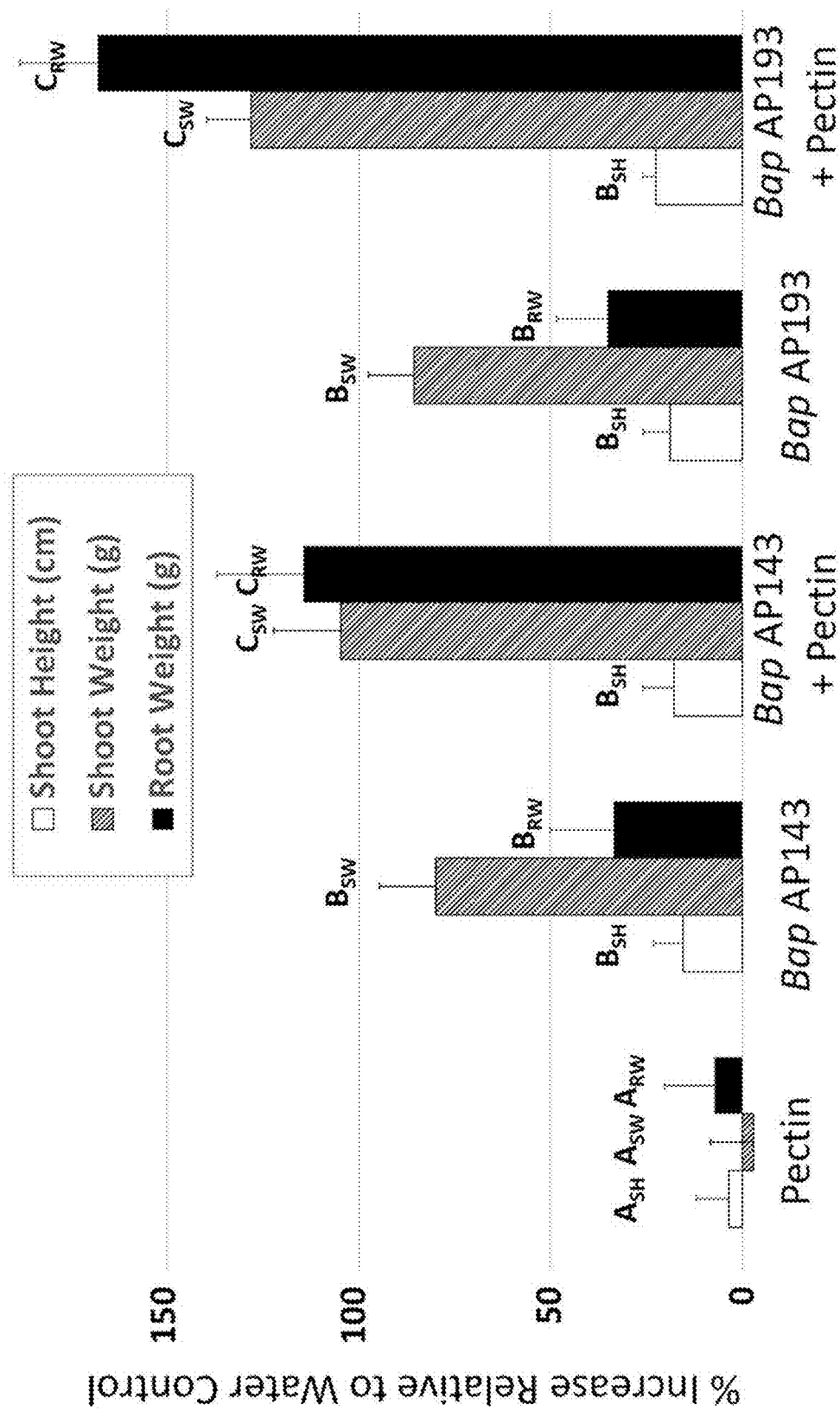
FIG. 3. Effect of PGPR and/or 0.1% (w/w) pectin soil amendment on soybean root and growth after 4 weeks. By strains AP143 and AP193 were applied as seed inoculants with $10^6$ CFU/seed and plants (n=11/treatment) were grown in a greenhouse. Treatment groups assigned different letters are significantly different (P<0.5).
Figure 4:
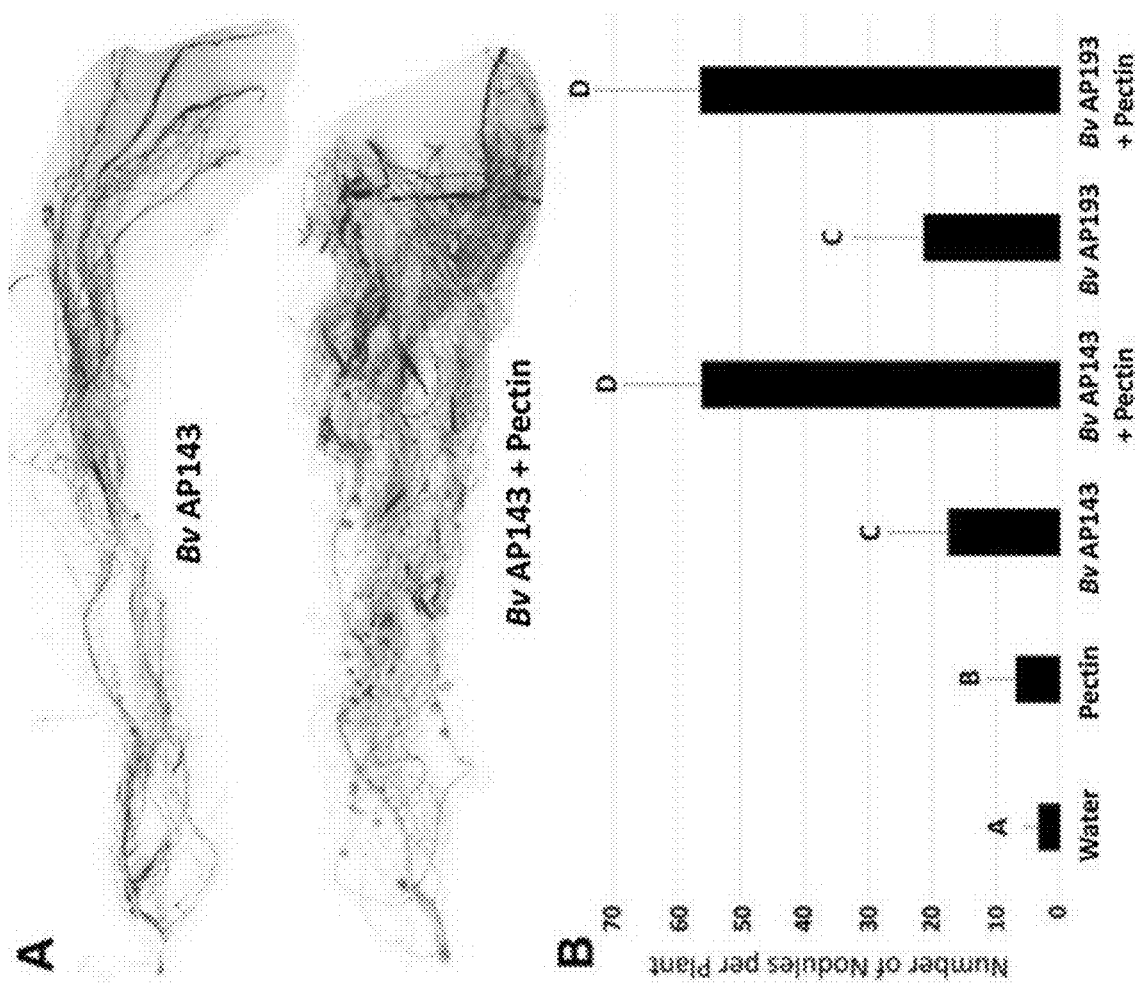
FIG. 4. A. Representative soybean roots grown in the presence of absence of 0.1% pectin amended to soil and seed inoculated with $10^6$ CFU By strain AP142. B. Effect of treatment groups that include $10^6$ CFU/seed By strains, with and without 0.1% pectin, on soybean nodulation (n=11). Treatment groups assigned different letters are significantly different (P<0.5).

There have been consistent observations that Bap (now Bv) strains with combined with pectin amendment increased the frequency of soybean root nodulation. Soybean root nodulation in Bap (now Bv) strains AP193 and AP143 with pectin supplement were fivefold and fourfold greater compared to Bap (now Bv) strains AP193 and AP143 without pectin supplement. This results indicate that pectin mixed field soil with Bap (now By) strain might induce soybean nodulation substantially than Bap (now Bv) strain without pectin supplement. There is a report that mixed inoculation of *Bradyrhizobium japonicum* with *Bacillus amyloliquefaciens* strain LL2012 enhanced soybean nodulation (Masciarelli et al., 2014). Another study also indicated that *Bacillus cereus* UW85 increased soybean nodulation in a growth chamber and the field conditions without inoculation of *Bradyrhizobia* spp. (Halverson and Handelsman, 1991). *Bradyrhizobia* spp. in the field soils may have enhanced root nodulation in the presence of Bap (now Bv) strains with pectin supplement. Co-inoculation of *Bacillus polymyxa* or *B. subtilis* with *Azospirillum* sp. was shown to allowed pectin degradation and nitrogen fixation by using pectin as a sole carbon and energy sources (Khammas, 1992).

Although, Bap (now Bv) strains with pectin supplement populations were not significantly different that Bap (now Bv) strains without pectin supplement populations, these re-isolations of Bap (now Bv) strains were only conducted using rhizosphere bacterial population counts. The two Bap (now Bv) strains, that colonization, while not significantly different, was about 0.5 log greater with pectin supplement, so a separate study on the effect of colonization at several time point, will be conducted. Therefore, future studies need to address whether PGPR bacteria are colonizing on the root rhizosphere, rhizoplane, or as an endophytic population. It may be possible that the Bap (now Bv) strains are not increasing in the CFU counts within the rhizosphere, rhizoplane or endophytically, but are utilizing the pectin and increasing the production of bioactive metabolites that are stimulating plant growth. By determining the production of Bap (now Bv)-derived metabolites in these different treatment groups we will be able to test the hypothesis.

REFERENCES

Beauregard, P. B., Chai, Y., Vlamakis, H., Losick, R., Kolter, R., 2013. *Bacillus subtilis* biofilm induction by plant polysaccharides. Proceedings of the National Academy of Sciences 110, E1621-E1630.

Halverson, L., Handelsman, J., 1991. Enhancement of soybean nodulation by *Bacillus cereus* UW85 in the field and in a growth chamber. Appl Environ Microbiol 57, 2767-2770.

Khammas, K. K., P, 1992. Pectin decomposition and associated nitrogen fixation by mixed cultures of *Azospirillum* and *Bacillus* species. Canadian journal of microbiology 38, 794-797.

Masciarelli, O., Llanes, A., Luna, V., 2014. A new PGPR co-inoculated with *Bradyrhizobium japonicum* enhances soybean nodulation. Microbiological research 169, 609-615.

Ridley, B. L., O'Neill, M. A., Mohnen, D., 2001. Pectins: structure, biosynthesis, and oligogalacturonide-related signaling. Phytochemistry 57, 929-967.

Example 3—Enhanced Soybean Growth Root Nodulation from PGPR and Pectin Application In recent years, PGPR have been developed as biofertilizers to promote plant growth (Calvo, 2014; Yan, 2002; Kloepper, 1994) and provide biological control of plant diseases (Liu et al., 2016a & b). co-PI Prof. Kloepper has a collection of PGPR strains that have shown plant growth-promoting activity in field soils on corn, soybean, wheat, canola, and several vegetable crops including tomato, pepper, and cabbage. Many of these PGPR strains have been identified as *Bacillus velezensis* (Note: their phylogenetic affiliation was previously described as *B. amyloliquefaciens* subsp. *plantarum* (now *B. velezensis*); Hossain et al., 2015; Bashan et al., 2014). *Bacillus* spp. strains can induce plant growth by diverse mechanisms including solubilizing phosphate and production of plant hormones such as indole acetic acid (Niazi et al., 2014). Many PGPR strains also produce many metabolites that protect plants against bacterial and fungal pathogens, or can induce systemic resistance (Adesemoye et al., 2009; Avdeeva et al., 2014, Liu et al., 2016a & b).

Our labs conducted a comparative genomic study on our 28 best-performing *B. velezensis* (By) strains, and found 73 genes consistently present in these genomes, but not present in other *Bacillus* species that lacked PGPR activity. These PGPR-specific gene products include the uptake and utilization of pectin-derived sugars (Hossain et al., 2015). We subsequently found that all 59 of the *B. velezensis* strains in our PGPR collection could use pectin as a carbon and energy source (data not shown). This led to our central hypothesis that pectin amendment to soil will increase root colonization by Bv PGPR strains leading to improved efficacy of plant growth promotion. There are no previous publications on the use of pectin to enhance rhizobacteria-mediated plant growth promotion or to induce legume nodulation. Our greenhouse trials to test our central hypothesis showed a significant 2-fold increase in soybean root weight when both By and pectin were amended to an agricultural soil compared to the water control (FIG. 3). Interestingly, we also observed an over 10-fold increase in soybean nodulation (FIG. 4). In addition, the size of the nodules produced in plants that had a PGPR inoculum and pectin supplementation greatly increased compared to a By strain alone (FIG. 4A). We hypothesize that increased pectinolytic activity or other By metabolites stimulated by pectin amendment enhances nodulation of soybean roots by native *Bradyrhizobium japonicum* present in soils previously cropped with soybean. We predict that the larger and more numerous nodules present on the more extensive soybean root systems will result in significant soybean yield increases. The greenhouse experiments represented in the above figures have been replicated and showed the same significant increases in root mass and nodulation size and frequency when pectin and PGPR were amended to soil (data not shown). These studies provide strong support for extending this research into field studies to evaluate soybean yield. We further anticipate that the use of pectin and PGPR inoculants will be a cost-effective and sustainable method to promote plant growth and reduce the variability inherent in the use of beneficial PGPR strains in field soils.

REFERENCES

Adesemoye A O, Torbert H A, & Kloepper J W. 2009. Plant Growth-Promoting Rhizobacteria Allow Reduced Application Rates of Chemical Fertilizers. Microbial Ecology 58:921-929.

Avdeeva L V, Dragovoz I V, Korzh Iu V, Leonova N O, Iutinskaia G A, Berezhnaia A V, Kuptsov V N, Mandrik M N, & Kolomiets E I. 2014. Antagonistic activity of *Bacillus amyloliquefaciens* subsp. *plantarum* IMV B-7404 and BIM B-439D strains towards pathogenic bacteria and micromycetes]. *Mikrobiol Z*. 76:27-33.

Bashan Y, de-Bashan L E, Prabhu S R, & Hernandez J P. 2014. Advances in plant growth-promoting bacterial inoculant technology: formulations and practical perspectives (1998-2013). Plant Soil. 378:1-33.

Calvo P, Nelson L, & Kloepper J W 2014. Agricultural uses of plant biostimulants. Plant Soil. 383:3-41.

Corbin, E J., Brockwell, j., and Gault, R. R. 1977. Nodulation studies on chickpea (*Cicer arietinum*). Australian Journal of Experimental Agriculture and Animal Husbandry, 17: 126-134.

Hassan, M K. 2016. The Role of Pectin Utilization in Root Colonization and Plant Growth-Promotion by *Bacillus amyloliquefaciens* subsp. *plantarum*. Thesis submitted to University of Auburn.

Hossain M J, Ran C, Liu K, Ryu C M, Rasmussen-Ivey C R, Williams M A, Hassan M K, Choi S K, Jeong H, Newman M, Kloepper J W, & Liles M R. 2015. Deciphering the conserved genetic loci implicated in plant disease control through comparative genomics of *B. amyloliquefaciens* subsp *plantarum*. Frontiers in Plant Science 6.

ISTA. 1993. Proceedings of the International Seed Testing Association, International Rules for Seed Testing. Seed Sci. Technol. 21:25-30.

Liu, K., Garrett, C., Fadamiro, H., Kloepper, J W. 2016a. Antagonism of black rot in cabbage by mixtures of plant growth-promoting rhizobacteria (PGPR) BioControl. 61: 605-613.

Liu, K., Garrett, C., Fadamiro, H., Kloepper, J W. 2016b. Induction of systemic resistance in Chinese cabbage against black rot by plant growth-promoting rhizobacteria. Biological Control. 99: 8-13.

Kjeldahl, J. 1883. Neue Methode zur Bestimmung des Stickstoffs in organischen Korpern. *Zeitschrift für analytische Chemie*, 22: 366-383.

Kloepper J W. 1994. Plant-growth-promoting rhizobacteria (other systems). *Azospirillum*/plant associations, ed Okon Y (CRC Press, Boca Raton), pp 139-154.

Kloepper J W, Ryu C M, & Zhang S A. 2004. Induced systemic resistance and promotion of plant growth by *Bacillus* spp. Phytopathology 94:1259-1266.

Kloepper, J W and Schroth, M N. 1981. Development of a powder formulation of rhizobacteria for inoculation of potato seed pieces. Phytopathology 71:590-592.

Niazi, A., Manzoor, S., Asari, S., Bejai, S., Meijer, J., Bongcam-Rudloff, E. 2014. Genome Analysis of *Bacillus amyloliquefaciens* Subsp. *plantarum* UCMB5113: A Rhizobacterium that improves plant growth and stress management. PLOS ONE. 9: e104651.

Yan Z N, Reddy M S, Ryu C M, McInroy J A, Wilson M, & Kloepper J W. 2002. Induced systemic protection against tomato late blight elicited by plant growth-promoting rhizobacteria. Phytopathology. 92:1329-1333.

Example 4—Grant Proposal for "Use of Pectin to Enhance Efficacy of Plant Growth-Promoting Rhizobacteria (PGPR) Strains to Improve Agricultural Productivity"

Introduction

Plant growth-promoting rhizobacteria (PGPR) have been identified that control plant diseases and promote overall plant growth. "Rhizobacteria" means root-colonizing bacteria, and hence, root colonization is essential for plant growth promotion by PGPR strains. Plant roots exude various organic compounds, including sugars, and successful bacterial colonization hinges on nutrient uptake from the host plants through extracellular enzymatic activity. Strains of *Bacillus amyloliquefaciens* subsp. *plantarum* (Bap) (now *Bacillus velezensis* (Bv)) colonize plant roots, and have been used as biofertilizers or biocontrol agents during the past decades. Some of the best-performing PGPR Bap (now Bv) strains at Auburn have been subjected to a comparative genomic analysis, which indicates that the use of pectin is a conserved trait among these sequenced strains. As a structural component of the plant cell wall, much is known regarding pectin biochemistry and plant synthesis; however, little is known about the possible role of pectin in root colonization. In fact, the current scientific paradigm regards pectin utilization as a function expressed by plant pathogens, and not as a potentially useful characteristic expressed by plant-associated PGPR strains. We now have experimental evidence that our best-performing PGPR Bap (now Bv) strains can obtain carbon and energy via 1) production of an extracellular pectinolytic enzyme(s) that degrades plant pectin into hexuronate sugars, 2) transport of pectin-derived sugars, and 3) utilization of these pectin-derived sugars for bacterial respiration. While these PGPR Bap (now Bv) strains consistently perform well under lab or greenhouse conditions, field trials are more variable in PGPR efficacy. We hypothesize that supplementing pectin levels on seeds or in the plant rhizosphere will improve the efficacy of PGPR strains in stimulating plant growth and disease control.

Introduction

There is a growing need for environmentally sustainable methods to promote plant growth in agriculture that has prompted the search for methods, like the probiotic strategies described in this proposal, to cost-effectively enhance plant growth. Plant growth-promoting rhizobacteria (PGPR) have been developed as biofertilizers to promote plant growth (8-11). While many species of bacteria are classified as PGPR strains, *Bacillus* species have been closely studied due to their spore-forming activity that confers a longer shelf life and greater viability in commercial formulations. Within this genus, strains of *Bacillus amyloliquefaciens* subsp. *plantarum* (Bap) (now *Bacillusl velezensis* (Bv)) have emerged as especially effective PGPR strains that lack any potential for pathogenesis (12, 13). At Auburn University, co-PI Kloepper has collected over 1,000 rhizobacteria isolates, of which over 300 have shown plant growth promoting activity in field soils on corn, soybean and wheat plants and 59 of these PGPR strains have been identified as Bap (now Bv) strains.

Some PGPR strains, including many Bap (now Bv) strains, can be used as biostimulants to promote plant growth (14). For example, microbial inoculants can solubilize phosphorus and/or fix nitrogen that can then be absorbed by plant roots, directly stimulating plant growth. There is a large body of literature on the use of bacterial inoculants for nitrogen fixation (15), and many *Bacillus* spp. strains have been identified as phosphate-solubilizing bacteria with commercial potential as biofertilizers (16). In addition, PGPR strains have been found to produce many secondary metabolites that have antibiotic activity against bacterial and/or fungal pathogens (17-19), including our discovery of the novel and potent antibiotic Bacillusin A produced by a Bap (now Bv) strain (20). PGPR strains can also induce the control of plant disease through production of compounds that induce plant systemic acquired resistance (SAR; mediated by salicylic acid) and induced systemic resistance (ISR; jasmonic acid-dependent) (8, 21, 22).

The earliest reported studies of seed bacterization for agricultural purposes dates to the use of *Rhizobium* inoculants on legumes in 1895 (23). Yield increases for cereal crops after bacterial inoculants were applied were observed in a variety of Soviet and Indian studies throughout the 1960s and early 1970s (23). However, field studies have consistently produced lower yields than greenhouse studies, suggesting that the introduced microbial population declines rapidly after soil inoculation (23, 24). This decline was likely due to an inability of the PGPR strains to compete and thrive within the rhizosphere. As described by Hawes et al. (26), "Efforts to improve plant health by adding exogenous populations of beneficial microorganisms (biological control) are notoriously unreliable" (25). Despite the inherent difficulties of using bacterial inoculants, the North American market for biostimulants, which includes PGPR, is estimated to grow to $490 million by 2018 (26). There is therefore strong interest in strategies that can enhance the efficacy of PGPR strains to improve agricultural productivity.

Our labs have conducted a comparative genomic study on our best-performing PGPR Bap (now Bv) strains, and we were able to identify 73 genes that were consistently present within all 28 genomes surveyed, but not present in other strains of *B. amyloliquefaciens* (now *B. velezensis*) that were known not to have PGPR activity (7). Importantly, we found that genes related to the uptake and utilization of pectin-derived sugars were always observed within these 28 PGPR Bap (now Bv) strains (7). This led to the hypothesis that root-derived pectin is important for beneficial rhizobacteria to colonize roots, produce bioactive metabolites and provide nutrients to plants, resulting in improved efficacy of plant growth promotion.

There is a significant knowledge base for pectin biochemistry that can benefit this project. Henri Braconnot discovered pectin in 1825 (27), and pectic substances are now known to be highly complex heteropolysaccharides that comprise a major component of plant primary cell walls in addition to cellulose and hemicellulose (28). For example, the primary cell wall of Sycamore is composed of 34% pectin, 24% hemicellulose, 23% cellulose, and 19% hydroxyproline-rich glycoprotein (29). The highest levels of pectin occur in the fruits, leaves, and roots of plants, so this is consistent with the potential for pectin to provide a needed root-derived nutrient source for beneficial microorganisms. Pectin is found in the middle lamella between cells, where it helps to bind cells together, and the availability and structure of pectins (polygalacturonans) varies among plant species (30). The demethylesterification of pectins, which is mediated through the action of pectin methylesterases, is an important process in seed germination (31) and in release of root border cells (32) which are living cells programmed to separate from roots into the external soil environment (26). Importantly, the mucilage produced by root border cells is rich in pectin and there is a "dramatic increase in the levels of soluble, de-esterified pectin in the root tip during border cell development" (32). The pectin-rich mucilage associated with root border cell release has been shown to be important for root penetration into soil, as well as binding metal cations such as aluminum to prevent toxicity (33, 34). However, to our knowledge no studies have investigated the contribution of root-derived pectin for beneficial plant-microbial interactions.

Pectin degradation occurs through the action of many different pectinolytic enzymes that are found in bacteria, fungi and higher plants. Protopectinases hydrolyze protopectin that exists in an insoluble form within plant tissues, resulting in soluble pectin, and have been observed in a wide range of *Bacillus* sp. (35). Many bacteria are known to secrete pectin lyases to degrade plant pectin. This pathway was first reported in *Escherichia coli* (36) and pectinolytic activity has been shown in the following bacterial genera: *Achromobacter, Arthrobacter, Agrobacterium, Bacillus, Clostridium, Erwinia, Pseudomonas*, and *Xanthomonas* (35). Many of these bacteria are recognized as plant pathogens, and the degradation of pectin is a characteristic of soft rot disease as caused by *Erwinia* species. Among soft rot pathogens there is evidence that pectinolytic activity is inducible and highly expressed compared to low-level constitutive expression of pectinolytic activities by non-soft rot bacteria (37); therefore, the competition for pectin as a nutrient source within rhizospheres could be a mechanism by which beneficial PGPR strains (e.g., Bap (now Bv)) antagonize plant pathogens without themselves causing plant damage. We have experimental evidence that our sequenced Bap (now Bv) strains encode and express a pectin lyase activity (FIG. 1).

By producing and secreting pectinolytic enzymes, bacteria can degrade pectin and uptake the pectin-derived sugars D-glucuronate, D-galacturonate and D-mannose (38), which can be taken up by bacteria via a hexuronate transporter (exuT). We found that the exuT gene is conserved among all sequenced PGPR Bap (now Bv) strains (7), and using an exuT-specific primer set we also found that this hexuronate transporter gene was present in all of the Bap (now Bv) strains in the Auburn collection (data not shown). A similar approach confirmed the universal presence within these Bap (now Bv) strains of the uxuB gene, which encodes D-fructuronate oxidoreductase that is one of the enzymes responsible for utilizing pectin-derived sugars (39). Furthermore, we have experimental evidence that our sequenced PGPR strains encode and express pectinolytic activity, and can use the resulting monosaccharides as a sole carbon source (data not shown).

Since the acquisition of carbon is essential for bacterial physiology we hypothesized that increased availability of pectin could promote the survival, persistence and metabolic activity of PGPR strains within plant rhizospheres, leading to improved plant growth and disease control. There have been two previous reports on the use of exogenously supplied pectin to stimulate plant-associated bacteria. In the case of nitrogen-fixing *Azospirillum* isolates, soils supplemented with pectin showed an increase in *Azospirillum* growth (40). There is also evidence that plant polysaccharides can induce biofilm formation in *B. subtilis* strains (5). However, in previous studies there was no attempt to evaluate any benefit for plant growth. In our preliminary studies, we have observed that there is a synergy between PGPR strains and soil amendment with pectin, resulting in statistically significant increases in root and shoot weight (FIG. 3). The soybean root and shoot growth enhancement with both Bap (now Bv) and pectin amendment was observed with both PGPR strains, with greater than a 2-fold increase in root weight (dry or wet) compared to the water control.

Interestingly, we also observed an over 10-fold increase in nodulation (FIG. 4B), with the size of the nodules produced in plants that had a PGPR inoculum and pectin supplementation greatly increased compared to a Bap (now Bv) strain alone (FIG. 4A). Whereas we had predicted the increased rate of root and shoot growth, the finding that nodulation was enhanced was a serendipitous discovery. We hypothesize that increased pectinolytic activity from the Bap (now Bv) plus pectin combination may result in enhanced *Bradyrhizobium* infection of soybean roots, since it has been shown before in the model legume *Lotus japonicus* that a mutant lacking pectate lyase activity was also deficient in nodulation (41). Based on the increased nodule frequency and size (FIG. 4A), we predict that the *rhizobia* metabolic activity within the nodules is increased relative to the no pectin controls, and that this results in greater nitrogen fixation rates. We further anticipate that the use of a pectin-rich soil amendment together with PGPR inoculants will be a cost-effective and sustainable method to promote plant growth and reduce the variability inherent in the use of beneficial PGPR strains in field soils.

Research Plan (Objective 1) Identify & Characterize Novel Plant Root Carbohydrate-Utilizing and Pecting-Utilizing Microorganisms.

Figure 2:
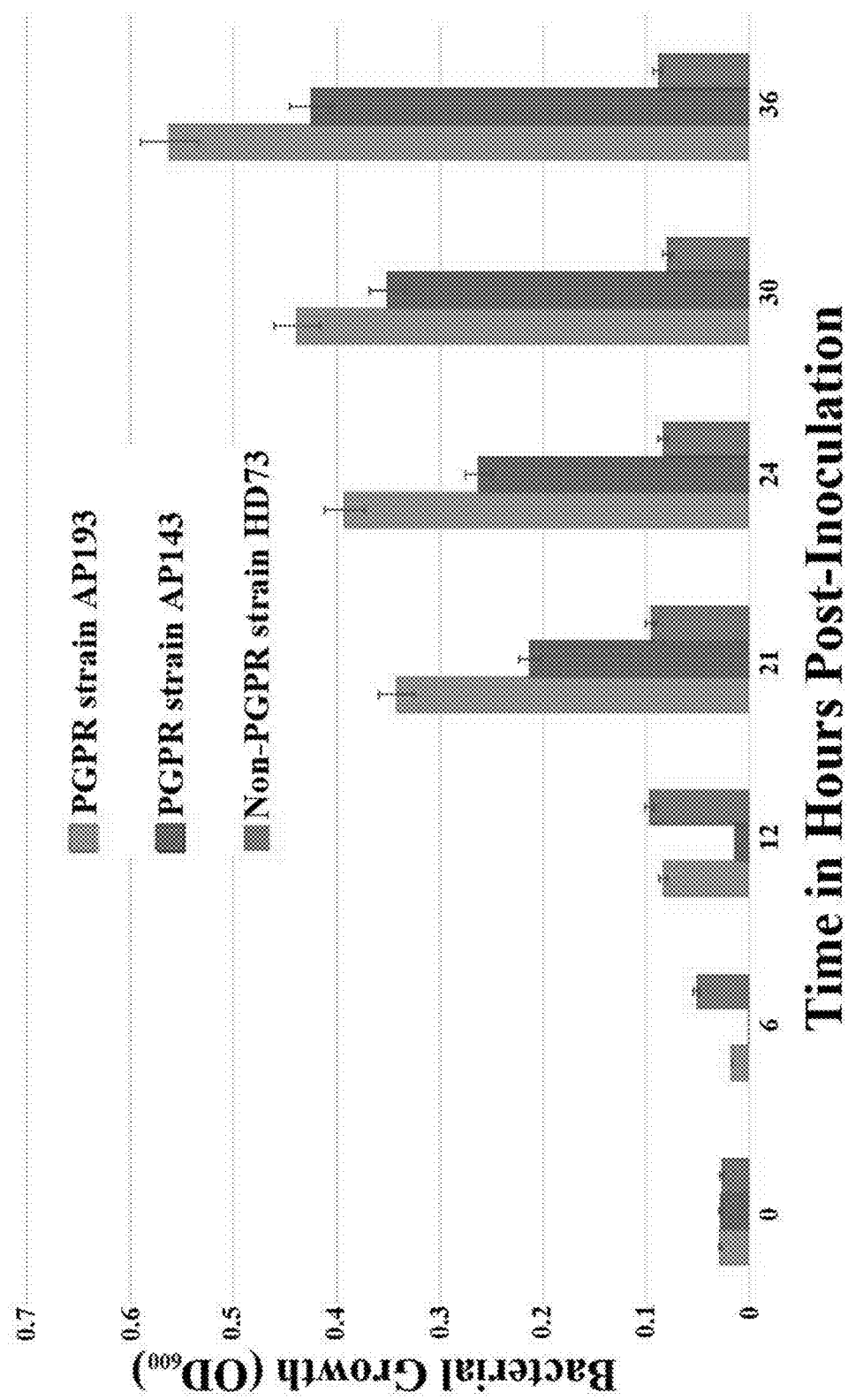
FIG. 2. Use of 1% pectin as a sole C source by PGPR strains AP143 and AP193 in TSS medium. The small increase in $OD_{600}$ by the non-PGPR strain HD73 was due to residual nutrients present from the previous TSB culture.

Surprisingly, a search of the literature for a microbial growth medium containing a "root extract" only yields a single publication in which soluble root exudates were used to enrich for root-associated Archaea (42). While citrus pectin-degrading microbes have been previously identified from soils (43, 44), to our knowledge no previous research effort has used plant root-derived complex carbohydrates incorporated into a growth medium to culture plant root-associated microorganisms. We will use a minimal medium containing either root extract or purified root pectin as a sole carbon and energy source, and will use long-term incubation conditions as have been done previously by our research group and others to culture soil bacteria that have not been previously cultivated under laboratory conditions (45, 46). In a preliminary study using soybean root incorporated into a minimal medium and inoculating agar plates with serially diluted soybean rhizosphere samples, we have isolated 184 bacterial isolates that formed colonies after 3 months of incubation. Among these, we have completed sequencing the 16S rRNA gene from 144 isolates, of which 39% have a 16S rRNA gene with a % identity <97% to their top hit in the GenBank database! These bacterial isolates include representatives from multiple bacterial phyla (i.e., alpha-Proteobacteria, beta-Proteobacteria, gamma-Proteobacteria, Bacteroidetes, and other phyla) and genera (e.g., *Inquilinus, Chitinophaga, Herbaspirillum, Flavobacterium, Delftia, Ralstonia, Burkholderia,* and *Dyella*). Interestingly, of the 22 unique isolates that have <97% identity to the top BLAST hit, 10 (45%) had top BLAST hits to previously uncultured soil bacteria. In this proposed study we will culture from multiple soil types and use root homogenates and root pectin to greatly expand our culture collection to identify microbial isolates with potential as PGPR strains. In a preliminary experiment, we have observed that two of our previously sequenced PGPR Bap (now Bv) strains, AP143 and AP193, could utilize pectin as a C source for growth (FIG. 2). As a negative control, a non-PGPR *Bacillus thuringiensis* subsp. kurstaki strain HD73 was obtained from the USDA ARS culture collection (Ames, Iowa) that was identified as a non-pectin utilizing strain based on its genome sequence. This strain was not observed to grow using pectin as a sole C source (FIG. 2).

(1A) Culture Rhizosphere Microorganisms Using a Root Extract Medium. Hypothesis: The Use of Plant Root-Derived Complex Carbohydrates as a C Source Will Enable Cultivation of Diverse Endophytic and Rhizosphere Microorganisms.

Experimental Methods:

The bacterial and fungal assemblages associated with plant roots will be cultured using long-term incubation on a minimal medium containing either a plant root extract or purified pectin.

Root Extract Preparation:

Root extract will be prepared using 10 corn (*Zea mays*) or soybean (*Glycine max*) roots grown in sand in pots in a greenhouse for 21 days. The washed roots will be homogenized with a mortar and pestle after freezing under liquid nitrogen, and then the homogenized roots will be suspended in sterile water in a 50 ml centrifuge tube. After centrifugation, the supernatant containing soluble root exudates (simple sugars and amino acids) will be removed. This washing will be repeated twice, and the root homogenate will be dried in a clean hood. The dry weight of the root homogenate will be used to prepare a suspension of 1 g root tissue per 10 ml sterile water. The root suspension will then be thoroughly homogenized using a T10 Basic Ultra-Turrax dispersion unit (IKA Works, Inc., Wilmington, Del.) which is capable of generating sub-micron sized particulates suitable as a microbial growth substrate.

Pectin Purification:

Commercially available pectin is derived from citrus or apple sources, and is chemically different from root pectin (47). Therefore, we will extract pectin from corn or soybean roots, using approximately 50 corn or soybean plants grown at the same time as the plants above. The washed roots will be shipped to the Complex Carbohydrate Research Center (CCRC) where the root pectin will be extracted by using a 0.5% ammonium oxalate buffer containing 0.1% $NaBH_4$ (pH 4) in a boiling water bath for 1 h each and pooling the supernatants as described previously (48).

Root Extract Medium (REM) Preparation:

The root or pectin extract will be added to a M9 salts minimal defined medium at a final concentration of 4 mg per ml based on preliminary experiments with a range of root extract concentrations (data not shown). After the addition of 1.5% agar and autoclaving the suspension, trace elements ($FeCl_3$, $ZnCl_2$, $CuCl_2$, $CoCl_2$, $H_3BO_3$, and $MnCl_2$) will be added to the REM according to the recommended concentrations (49) and plates will be thickly poured (30 ml per plate) after magnetic stirring. There will be a total of 4 different media prepared (corn root, corn pectin, soybean root, soybean pectin) for cultivation efforts.

Cultivation of Microorganisms:

Soils will be sampled from actively growing corn or soybean plants in distinct soil types (clay, sandy and loam soils) within proximity to Auburn University. The sandy soil will be collected from the Cullars Rotation in plots that have not received K or P inputs for over 100 years, but yet have diverse microbial communities (50). Intact roots with associated rhizosphere will be sampled from five plants per site and then pooled together. In order to access both endophytic and rhizosphere microorganisms, sub-samples will be suspended in sterile water (10% w/v) and homogenized to produce a fine suspension of microbial cells. This microbial suspension will be serially diluted, and the $10^{-4}$, $10^{-5}$ and $10^{-6}$ dilutions will be plated onto the four REM medium types with 10× replication (a total of 30 plates per media type per soil site; 120 total plates per soil site). From previous experience, the $10^{-5}$ and $10^{-6}$ dilutions provide isolated colonies on a soybean REM whereas the $10^{-4}$ dilution tends to be overgrown with microbial colonies. The inoculated plates will be wrapped in parafilm and maintained in containers in which humidity is kept elevated to avoid plate desiccation. The plates will be incubated for 2-3 months with regular monitoring for the appearance of microbial colonies. After incubation, colonies will be passaged onto the same REM type as their original isolation to obtain isolated colonies from pure cultures. Pure cultures will be documented for their colony type by taking digital photos using a digital microscope and will then be cryopreserved in REM broth with 20% glycerol, prior to storing replicate tubes at −80° C. The primary isolation of plant root carbohydrate-utilizing microorganisms will be repeated as necessary to achieve several thousand pure microbial cultures in our collection.

Expected Results:

A large culture collection of plant-associated microorganisms that can utilize plant root-derived carbohydrates will be obtained that include many novel microbial taxa.

Anticipated Problems and their Solutions:

Based on our previous efforts to cultivate previously uncultured bacterial taxa from soils (46), a principle challenge is maintaining the viability of laboratory cultures. Sequential passaging may lead to loss of some cultures due to insufficient nutrient availability or other unknown factors. Therefore, each culture will be cryopreserved at passage one when a pure culture has been obtained so that if a culture losses viability that it may be resuscitated on a different growth medium, especially if there is promising data generated regarding phylogenetic affiliation or beneficial plant interactions. It is also anticipated to be difficult to continually prepare root extract medium agar plates because this requires growing corn and soybean plants for medium preparation. We will therefore explore the use of commercially available root extracts that are known to be pectin-rich (e.g., beet pulp) to prepare REM agar and broth in order to maintain laboratory cultures for subsequent experiments.

(1B) Conduct a Phylogenetic Analysis of Cultured Microbial Isolates. Hypothesis: The Bacterial and Fungal Isolates Obtained from Obj. 1A Will Include Recognized Plant Pathogens, Beneficial Microbes as Well as Novel Cultured Isolates that have not been Previously been Characterized for their Plant Interactions.

Experimental Methods:

Each of the pure microbial cultures obtained in Obj. 1A will be subjected to a molecular phylogenetic analysis based on a comparison with 16S rRNA sequences for Bacteria (or Archaea, should these be isolated) and internal transcribed spacer (ITS) analysis for fungal isolates. A portion of the pure culture from passage one will be swabbed from the REM agar plate into 1 ml of sterile water within a microcentrifuge tube, and after centrifugation at 10,000×g the microbial pellet will be used to isolate genomic DNA using an E.Z.N.A. genomic DNA isolation kit (Omega Biotek, Atlanta, Ga.). The genomic DNA will be used as a template for a PCR in which 'universal' bacterial 16S-specific (27F and 1492R (51)) or fungal ITS-specific (ITS86F and ITS4 (52, 53)) primer sets are used in order to generate an amplicon from each isolate. The PCR product will be purified over a column and used for Sanger sequencing with a forward or reverse primer (e.g., 27F and 907R) sufficient to provide a consensus sequence over a large portion of the amplicon. The consensus 16S rRNA gene or ITS sequence will be generated using the CLC Genomics Workbench (Qiagen, Cambridge, Mass.) and these will be subjected to a multiple sequence alignment and maximum likelihood analysis (1000 iterations using RAxML (54)). Each of the unique isolate sequences will be compared against the databases at GenBank (nr/nt) and Ribosomal Database Project (RDP) in order to identify the nearest neighbor for each of the microbial taxa. A record of the % identity, nearest neighbor, and its phylogenetic affiliation will be recorded for each isolate within a lab PlantMicrobiomeNet database (see Data Management Plan), and if the isolate corresponds to a known pathogen (e.g., *Erwinia* sp.) or beneficial microbe (*B. subtilis*) this will also be indicated within the database. Of particular interest will be isolates that do not fall into either of the latter categories and have a relatively low % identity (<97%) to known cultured microorganisms within GenBank or RDP. Based on these results we will assemble 96-well plates containing a glycerol stock of each of the unique isolates, in triplicate, that is not affiliated with a known pathogen. We will group the isolates based on their relative rate of growth so that each 96-well plate contains isolates that will take approximately the same amount of time to reach the stationary phase of growth.

Expected Results:

The phylogenetic affiliation for each of the pure cultures obtained in Obj. 1A. Other outputs from this objective will be a collection of genomic DNAs from each isolate, an indication of whether each culture represents a taxon that has not been previously cultured in vitro or been associated with plants, and a 96-well plate formatted culture collection.

Anticipated Problems and their Solutions:

This objective has a high probability of success. If an isolate does not provide a PCR amplicon, which could be due to the primer set not amplifying from unique microbial taxa, alternative primer sets will be used; if necessary, genomic DNA will be further purified using a method developed by the PI (55).

(1C) Screen Cultures for Plant Hormone Synthesis and the Ability to Promote Plant Growth. Hypothesis: Many of the Microbial Isolates Will have the Ability to Induce Plant Hormone Expression and Will be Able to Stimulate Plant Growth.

Experimental Methods:

Each of the pure cultures that have been identified as non-pathogenic in Obj. 1B will be used to inoculate *A. thaliana* that express green fluorescent protein (GFP) in response to plant hormones, and to test for soybean growth promotion.

Broth Culture of Microorganisms:

Each 96-well cryopreserved plate containing the unique, non-pathogenic microbial cultures (bacterial and fungal) in triplicate will be used to inoculate a 96-well, deep-well plate with each well containing 1 ml of REM broth. Each plate will also contain controls inoculated in triplicate wells, the positive control will be *B. amyloliquefaciens* (now *B. velezensis*) FZB42 which has been previously shown to produce auxin (56), and the negative control will be *Bacillus thuringiensis* HD73 that does not produce any plant hormone. A breathable, sterile film will be placed over each 96-well plate which will be shaken at 200 rpm for approximately 1 week. The exact length of time will depend on preliminary experiments to establish the rate of growth for representative isolates in this REM broth medium. Each plate will be monitored for the growth of the cultures and used when the cultures have attained sufficient turbidity ($OD_{600}>0.5$) to inoculate wells containing the *A. thaliana* bioassay.

Bioassay for Plant Auxin or Cytokinin Response:

Auxin and cytokinin are essential plant hormones involved in root growth and are likely to be involved in the promotion of plant growth by PGPR strains. Since direct measurements of these plant hormones is both difficult and time consuming, indirect fluorescent reporter lines have been generated and are standardly used to analyze auxin (DR5) and cytokinin (pTCSn) (57, 58). We have bred each reporter line linked to a different fluorescence protein together to generate a single plant wherein both auxin and cytokinin response can be examined simultaneously. This hormone responsive line contains both DR5-YFP and pTCSn-GFP reporters. Seeds of this hormone-responsive line will be added to 96-well plates in which 0.5 ml of molten (42° C.) 1.4% agar in water has been added to each well, and then a multichannel pipettor will be used to transfer 0.5 ml of the respective microbial culture to each well and will be mixed by pipetting. The seedlings will be grown for five days under standard growth conditions and then roots will be analyzed for changes in response to auxin and cytokinin levels based on altered fluorescence using an epifluorescence microscope. Both positive (hormone treated) and negative (blank) controls will be examined in parallel and replicated to determine the results for this objective. Positive results of hormone response will be confirmed using qPCR expression analysis of routinely examine auxin and cytokinin responsive genes (e.g. IAAs and type-ARRs) as described previously (59).

Greenhouse Bioassay for Plant Growth Promotion:

The microbial isolates will also be tested for their respective ability to promote soybean plant growth in an Alabama field soil in a greenhouse. The experiments will be designed in a randomized complete block design in triplicate. Conetainers that are 2.5 inches in diameter and 8.25 inches deep will be filled with the same weight of thoroughly mixed field soil. Prior to planting, the soil water content in conetainers will be adjusted to 60% field capacity. At planting, one soybean seed will be placed into the center of each conetainer at a depth of 1 inch, followed by pipetting 0.5 ml of the respective microbial suspension over the top of each seed, then covering the soybean seed with soil. Watering conetainers will begin 24 hr after planting. PGPR Bap strain AP193 used as a positive control; *B. thuringiensis* strain HD73 and water only will be used as negative controls. Plants will be transferred to the greenhouse and watered daily for 21 days, after which the dry shoot and root weights will be determined. For each isolate's impact on plant root and shoot growth the variation will be compared to controls and analyzed using ANOVA at 5% level of significance.

Expected Results:

Identification of specific microbial cultures that produce plant hormones and/or induce plant growth that could be used as PGPR strains.

Anticipated Problems and their Solutions:

There is inherent variability in bioassays that may result in false negative or positive results. By conducting both laboratory (*A. thaliana*) and greenhouse assays in this objective we will increase the likelihood of observing biologically meaningful plant growth stimulation. The isolates that promote plant growth and/or produce plant hormones will be further tested in a potato slice assay (60) to eliminate any isolates with the potential for inducing soft rot. We will select specific strains based on their positive effects on plant growth to advance to field studies to assess their potential for plant growth promotion and/or disease biocontrol, and these studies will be conducted using other funding sources.

(Objective 2) Evaluate the Ability of Exogenous Pectin Supplementation to Enhance PGPR-Mediate: Plant Growth.

In preliminary experiments we have observed that amending soil with citrus-derived pectin can significantly enhance PGPR-mediated plant growth (FIG. 3) and nodulation frequency and size (FIG. 4). In this objective we will investigate the effect of pectin concentration on PGPR strain growth in soils; furthermore, we will assess the effects of soil type and pectin source on PGPR-mediated growth enhancement of corn and soybean plants. Lastly, we will determine the impact of *A. thaliana* mutants that modulate root pectin levels on PGPR-mediated growth promotion. These studies will advance the agricultural applications of this science and foster our understanding of the role of pectin in mediating plant-microbial interactions.

(2A) Determine Pectin Dose-Dependent Enhancement of PGPR Strain Growth, Hypothesis: There Will be a Pectin Dose-Dependent Increase in Bap (Now Bv) Growth within the Rhizosphere.

It is important to first determine the concentration of pectin to use in subsequent plant growth experiments. Our initial experiments evaluated different pectin (citrus source) concentrations from 0.001% to 5% on soybean seed germination, and observed slightly inhibited germination rates at concentrations >1%, and our initial greenhouse trials have therefore been conducted using 0.1% pectin amended as a dry ingredient to soils.

Experimental Methods:

In order to track strain colonization in soils we have identified rifampicin (Rif)-resistant mutants using 50 µg/ml Rif for Bap (now Bv) strains AP143 and AP193, and these Rif$^R$ mutants have similar growth and PGPR activity compared to the wild-type strains (data not shown). A negative control strain, *B. thuringiensis* strain HD73, which does not use pectin as a carbon source (61) and does not have PGPR activity (data not shown), was also used to select a Rif$^R$ mutant. The experimental system for assessing root colonization by the Rif$^R$ mutants will be the same greenhouse tests as described above in Obj. 1C using soybean seeds grown in field soil. Seeds will be inoculated at the time of planting with 1.0 ml of AP143, AP193 or HD73 Rif$^R$ spores ($10^6$ colony forming units (CFU)/seedling) applied in soils that receive 1) no amendment, 2) 0.01% (w/w) pectin 3) 0.025% pectin, 4) 0.05% pectin, or 5) 0.1% pectin, with 8 replications for each treatment group. At 21 days post-inoculation, 10 g of rhizosphere soil will be sampled from each of the pots, and the dry shoot and root weights will be determined. The numbers of nodules formed per soybean plant will also be determined along with the average nodule mass. The soil will be homogenized in 90 ml of sterile water ($10^{-1}$ dilution) and then serially diluted to $10^{-6}$ dilution and each of the dilutions from $10^{-1}$ to $10^{-6}$ will be plated onto TSA plates containing 50 µg/ml Rif in order to determine the number of Rif$^R$ CFU/g of soil for each of the PGPR strains and the negative control strain.

Expected Results:

Determination of the pectin dose-dependent increase in growth of the PGPR Bap (now Bv) strains when amended into soil. The results of this experiment are expected to show a significant pectin dose-dependent increase in the CFU/g of Bap (now Bv) strains AP143 and AP193, with no significant increase observed for pectin-incompetent strain HD73. These results will enable the selection of a pectin concentration to use in Obj. 2B. We will also evaluate the degree of nodulation enhancement and future studies will investigate the molecular basis for the increase in nodulation frequency and metabolic activity associated with pectin and PGPR inoculation.

Anticipated Problems and their Solutions:

To confirm that the CFU counts of the Rif$^R$ are due to the inoculated PGPR Bap (now Bv) strains, representative colonies will be selected to conduct PCR using an AP143 or AP193 strain-specific PCR primer set that has been developed in the Liles lab (data not shown). Our preliminary experiments have not shown any Rif$^R$ colonies identified from plants that have not been inoculated with a *Bacillus* Rif$^R$ strain.

(2B) Evaluate Pectin Enhancement Op PGPR-Mediated Plant Growth Promotion Using Multiple Pectin Sources, Plants and Soils. Hypotheses: There Will be a Significant Increase in Plant Growth in Response to PGPR and Pectin Amendment Compared to PGPR Inoculation Alone. Soil Amendment with Beet Pulp Will Provide Similar Results in Enhancing PGPR-Mediated Plant Growth as with Citrus-Derived Pectin.

Experimental Methods:

We will conduct this greenhouse experiment in separate trials using soybean and corn plants. In each separate trial, plants will be will be sown in trays that contain a sandy loam soil (Cullars Rotation soil) or a field soil used routinely in greenhouse studies, and 3 weeks later transplanted into 8 inch pots that contain the respective soil. As with previous experiments we will incorporate pectin into soil as a dry ingredient, and we will use a concentration depending upon the results of Obj. 2A. The PGPR strain will be applied as a 1 ml drench to each seedling three days after transplantation. In addition to the commercial source of citrus pectin, we will also evaluate the use of powdered beet pulp as an alternative and cost-effective, pectin-rich amendment (62). The treatment groups will include 1) no PGPR in loamy soil, 2) no PGPR in clay soil, 3) $10^6$ CFU/seedling PGPR Bap (now Bv) strain AP193 in loamy soil and 4) $10^6$ CFU/seedling PGPR Bap (now By) strain AP193 in clay soil. These four treatment groups will each be incubated with soil without pectin, with citrus pectin or beet pulp (n=12 treatment groups with 8 replicates=96 pots per each experiment). A completely randomized blocked design will be used. Fresh and dry weight of root and shoot will be measured at the completion of the greenhouse experiment after 4 weeks. Root morphology will be analyzed by a WinRHIZO root scanner (Regent Instruments, Quebec City, Canada). The numbers of nodules formed per soybean plant will also be determined along with the average nodule mass. For each parameter the variation of each treatment will be compared and analyzed using ANOVA at 5% level of significance (SAS 9.1 software). These experiments will be repeated with soybean and corn, and if additional low-cost sources of pectin are identified we will evaluate the use of these alternative soil amendments to enhance PGPR-mediated plant growth promotion.

Expected Results:

The addition of citrus pectin or beet pulp to Bap (now Bv)-treated soybean seeds will result in an increase in soybean root and shoot growth relative to non-pectin-treated plants. No pectin-mediated increase will be observed in the plants without a PGPR strain inoculum.

Anticipated Problems and their Solutions:

There can be unforeseen issues, such as a disease outbreak, in experimental plants. We will take ample precautions to limit disease incidence, and plan to repeat this experiment at least once and more if necessary. The timing of the experiment may need to be extended to achieve significant differences among treatment groups.

(2C) Evaluate PGPR Colonization and Persistence in Wild Type *Arabidopsis* vs Pectin Biosynthesis Mutants. Hypothesis: A Reduced PGPR-Mediated Increase in Plant Growth Performance Will be Identified in *Arabidopsis* that have a Defect in Pectin Biosynthesis Relative to Wild-Type.

Because *A. thaliana* does not exhibit a distinct root border cell separation as with other plant species (63), it will be of interest to evaluate PGPR-dependent growth responses for wild-type and mutant *A. thaliana*.

Experimental Methods:

As discussed above pectin is a complex polysaccharide for which there are many biosynthesis and catabolism pathway steps. Because of this there are numerous genes involved in these processes, and subsequently in *Arabidopsis* there are numerous potential mutants to be examined that could have altered pectin levels. However, even in the well-studied *Arabidopsis* system only a handful of gene mutants have been shown to have altered pectin levels in root tissues. We will examine the two best characterized mutants with defects in pectin biosynthesis that are root expressed, quasimodo1 and 2 (qua1, qua2). The QUA1 gene encodes a glycosyltransferase (also known as GUAT8) and its mutant qua1 has been shown to have 25% less homogalacturonan (HG) and have a reduction in pectin esterification (64). QUA2 is a pectin methyltransferase and its mutant qua2 has 50% less HG with normal esterification levels (65). Importantly, both mutants in these genes show alterations in root border cell separation (reduced cell adhesion) resulting in distinct border cell separation typically observed in the other crop species (soybean and corn) examined in this proposal (63). To our knowledge these are the only cell adhesion mutants that have pectin defects in roots. The selected qua1 and qua2 mutants have a dwarfed stature resulting from their reduction in pectin biosynthesis, although these mutants are still viable (8, 65, 66). While there are a few other *Arabidopsis* mutants in pectin-related biosynthesis genes that are expressed in root tissues, these either show no change in growth phenotype possibly due to the large degree of redundancy in this pathway or have little information regarding changes in pectin levels (67). The Bap (now Bv) strain AP193 will be inoculated onto wild-type, QUA1, or QUA2 mutant *A. thaliana* seeds at an inoculum of $10^6$ CFU per seed such that the impact of mutant phenotype on PGPR-mediated growth response can be assessed and compared to negative controls (water or *B. thuringiensis* strain HD73). Inoculated seeds will be germinated and grown under several standard conditions (96-well plate as noted above, standard agar plates and soil growth chamber conditions). Plants will have basic growth (leaf size and number, silique and seed production) and health (Fv/Fm chlorophyll fluorescence) measured at distinct stages across development to determine PGPR-mediated effects. Measurements at all stages will be performed with a minimum of 10 plants per treatment group and measurements will be analyzed as noted above.

Expected Results:

Reduced PGPR-mediated growth will be observed in the *A. thaliana* pectin synthesis mutants compared to the wild-type control.

Anticipated Problems and their Solutions:

Some alleles of the qua1 and qua2 selected mutants have extreme dwarf growth phenotypes that would make the proposed examinations difficult to conduct. As such we will select more robust alleles that still have pectin defects, readily available from the *Arabidopsis* stock center to conduct these assessments.

(Objective 3) Determine the Identity and Functions Associated with Root Pectin-Metabolizing Soil Microorganisms Using Culture Independent Approaches.

The experiments described above rely upon culture-dependent studies of novel rhizosphere microorganisms and known PGPR strains. While the use of cultured PGPR strains has great utility for application in agriculture, we also know that the vast majority of soil microorganisms are not readily cultured under laboratory conditions (68). In this objective we will therefore use stable isotope probing (SIP) with $^{13}$C-root pectin in order to study the phylogenetic diversity and functional contributions of soil microorganisms that utilize root pectin as a C source. We will complement this culture-independent approach by studying microbial genomes recovered from a soil metagenomic library that are predicted to encode pectin-degrading or -utilizing functions.

(3A) Determine the Phylogeny and Functions of Soil Microbial Taxa that Utilize $^{13}$C-Pectin, Hypothesis$_1$: The Pectin-Utilizing Microorganisms Identified Will Include Those Identified in Objective 1 and Will Also Include Other Microbes that have not been Previously Associated within Pectin Utilization or Characterized as Plant-Associated. Hypothesis$_2$: The Pectin-Utilizing Microbes Will Express Gene Products that are Predicted to be Important for Plant Growth.

Experimental Methods: $^{13}$C-Stable Isotope Probing.

We will evaluate the soil microbial use of $^{13}$C-root pectin with and without the presence of the PGPR Bap (now Bv) strain AP193. The Cullars Rotation soil (described above) will be added to trays in which corn seeds will be sown. After three weeks the seedlings will be transplanted into 4.5 inch pots containing soil with and without 0.1% root pectin (w/w) extracted from corn roots by the CCRC (see above). Additional pots will be planted to guard against loss of plants from disease and to serve as controls and for method refinement. For the appropriate treatment groups, three days after transplantation a 10 ml PGPR inoculum will be applied as a 10 ml root drench ($10^6$ CFU/seedling) and then all plants will be grown for 3 weeks in a greenhouse prior to addition of the $^{13}$C-pectin inoculation. This is comparable to a study in which $^{12}$C-carbohydrate amendments (but not pectin) were added to soils for 3 weeks prior to addition of the $^{13}$C label (69). As in this study, we will assess $CO_2$ production from replicate pots receiving unlabeled root pectin at different concentrations using headspace-collected $CO_2$ and will measure $CO_2$ at the Auburn University Mass Spec facility using a Shimadzu GC-2014 gas chromatograph, using multiple time points post-pectin addition in order to establish the appropriate concentration of $^{13}$C-pectin to add and the time frame for sampling. Our ability to identify the soil microorganisms that are responsible for actively degrading and incorporating $^{13}$C-pectin will be enabled by isolating RNA from soils which is more labile and representative of metabolically active microorganisms. Unlike readily metabolized substrates such as $^{13}$C-glucose in which RNA-SIP is conducted within 12 hours (reference), a more complex polysaccharide such as pectin should require a multiple day time frame for this study. There will be two treatment groups (control, PGPR)×4 replicates×4 time points for a total of 32 pots. The $^{13}$C-labeled root pectin will be prepared by purchase of 20 g uniformly $^{13}$C-labeled [97 atom % $^{13}$C] corn root (IsoLife, Wageningen, The Netherlands), and pectin will be extracted from root tissue by the CCRC as described above at the scale needed to have sufficient root-derived pectin for soil amendment (estimated yield ~4 g $^{13}$C pectin). Each pot will contain ~100 g of soil, therefore our total needed yield of $^{13}$C-pectin will be 0.1 g per pot×32 pots=3.2 g. Four time points will be sampled, at time zero just prior to a $^{13}$C-root pectin inoculum equivalent to the concentration used in previous experiments (0.1% (w/w)) in a 10 ml volume and then at three post-inoculation time points (~24, 48 and 72 hours, depending on the results of $CO_2$ production). At each time point we will sample the rhizosphere soil from each plant, adding approximately 2 g of rhizosphere soil to 5 ml of LifeGuard™ Soil Preservation Solution (MoBio, Carlsbad, Calif.) in a 15 ml collection tube, and a replicate tube will be frozen at −20° C. which will remain viable for RNA/DNA isolation for >30 days. Total DNA and RNA will be isolated from 2 g of soil sample using the PowerSoil Total RNA Isolation kit (MoBio) in a dedicated RNA processing area of the PI's lab. DNA will be separately eluted using a DNA Elution Accessory kit (MoBio) and RNA and DNA samples will be quantified using a Qubit fluorometer. The RNA samples will be separated on a cesium trifluoroacetate isopycnic gradient subjected to ultracentrifugation at 128,000×g for 50 hr using a Beckman ultracentrifuge. Control gradients using a pure bacterial (Bap (now Bv) AP193) culture grown on $^{12}$C-pectin or $^{13}$C-pectin will be conducted in advance to establish conditions that result in good separation of light from heavy RNA (70), and a syringe pump will be used in order to provide a low flow rate (~200 μl/min) for fraction collection in sterile RNAse-free microcentrifuge tubes. We will quantify the amount of RNA in each 100 μl fraction using a rapid qPCR method targeting bacterial rRNA (71) using SYBR Green fluorescence in a Bio-Rad CFX real-time PCR system (Hercules, Calif.) in order to establish migration of light and heavy RNA. Fractions with abundant extracted RNA will be pooled for the fractions exhibiting clear separation of heavy from light RNA, treated with DNase I, and then reverse transcribed using M-MLV Reverse Transcriptase (Invitrogen, Carlsbad, Calif.). The resulting cDNA will be used for shotgun metagenomic sequencing.

Microbiome Analysis:

The $^{13}$C-labeled cDNA and total DNA recovered from each sample (32 samples, with cDNA and DNA, for a total of 64 samples) will be used as a template for 16S rRNA and gyrB gene PCR amplification. While the 16S rRNA gene is the most common molecular target in microbiome studies, it produces a distorted representation of microbial relative abundance due to differing copy numbers of the rRNA operon within microbial genomes. We will use a two stage polymerase-exonuclease (PEX) PCR method in development with our collaborator Dr. Stefan Green (Univ of Illinois-Chicago) that results in improved evenness of amplification across mixed templates and allows for greater primer degeneracy (72). Using the cDNA or DNA templates, an analysis based on the standard Illumina protocol for 16S rRNA gene sequence amplicons with the 2-stage PEX-PCR protocol will be conducted for both 16S rRNA and gyrB sequences. Since gyrB is a housekeeping gene that is single-copy, we expect that this will result in a less biased representation of the microbiome, and we have already generated a novel set of 'universal bacteria' gyrB primers that will be used in this study (data not shown). Using the QIIME pipeline and custom scripts, the 16S and gyrB sequences will be trimmed, binned into operational taxonomic units (OTUs) based on >97% identity, and compared to existing phylogenetic databases to determine the relative abundance as compared to the known colony forming units. By conducting principal coordinate analysis from the 16S and gyrB sequence data we will reveal trends in the comparison of treatment groups at the different phylogenetic resolutions afforded through 16S and gyrB, respectively. The known 16S rRNA and gyrB sequences for Bap (now Bv) strain AP193 will be used for comparison.

Next-Generation Sequencing (NGS) and Bioinformatics Analyses:

In order to reduce the number of samples used for NGS analysis, we will evaluate the concentration of heavy cDNA to identify samples in which there was less recovered $^{13}$C labeled cDNA. Of the 32 total samples processed, we expect to be able to eliminate one of the time points resulting in ~24 $^{13}$C-cDNA samples. For comparison purposes we will also include the total DNA sample recovered from each sample and each of the samples will be bar-coded for Illumina sequencing using the Nextera kit (Illumina, San Diego, Calif.) using a unique index. We will include 8 samples per Illumina HiSeq lane in order to provide sufficient coverage per sample in order to better access lower abundant transcripts. The raw sequence reads will be trimmed for sequence quality equivalent to a Q score >30 and the trimmed reads will then be used for de novo assembly using the SPAdes assembler running on the Auburn University supercomputer. We will compare the transcriptome from each sample and treatment group using the CLC Genomics Workbench in order to identify differentially expressed transcripts in each treatment group and to determine the highly expressed transcripts present within the $^{13}$C-enriched sample. We will submit the transcripts to the MG-RAST automated pipeline for microbial metagenomic analysis and will in particular be seeking information on plant-related functions. Our specific molecular targets will include transcripts related to nutrient (NPK) acquisition, plant hormone production, and secondary metabolite synthesis, among other potential functions. The contigs from each transcriptome will also be submitted to the antiSMASH pipeline for biosynthetic cluster identification to provide enhanced detection of biosynthetic clusters, with comparisons of the % identity and synteny of each discovered pathway with known pathways from the GenBank database. These analyses will lead to testable hypotheses regarding pectin-utilizing microorganisms and their contributions to plant growth.

Expected Results:

A culture-independent analysis of the pectin-utilizing microorganisms within the corn rhizosphere. This will indicate the phylogenetic affiliation and the expressed functions of the pectin-utilizing microorganisms, with a particular emphasis on plant-related phenotypes.

Anticipated Problems and their Solutions:

One potential problem will be that using a living corn plant will result in dilution of the $^{13}$C enrichment for pectin-utilizing microorganisms. It will therefore be necessary to carefully monitor the degree to which providing exogenous pectin stimulates microbial respiration by the series of control pots using non-labeled pectin prior to the $^{13}$C-pectin experiments. In this way we can maximize the degree to which the RNA of the pectin-utilizing microbes has incorporate the $^{13}$C label and can be separated from non-labeled RNA.

(3B): Mine a Soil Metagenomic Library for Pectinoyltic Enzymes and Associated Functions.

We have previously constructed a large-insert soil metagenomic library from the same plot of the Cullars Rotation soil that will be used for the SIP study. High molecular weight DNA isolated from the soil microbiota (73) was randomly sheared and ligated into a bacterial artificial chromosome (BAC) vector, resulting in a metagenomic clone library containing 110 kb average insert sizes with 19,200 clones. The library consists of 50 384-well plates, and based on the average insert size the total amount of cloned metagenomic DNA is estimated to exceed 2 Gbp, or over 500 *Escherichia coli* genome equivalents (data not shown). A next generation sequencing strategy was used in which clones were pooled from each of the 50 plates, 24 columns and 16 rows separately and each pool was uniquely bar-coded and sequenced using multiple Illumina HiSeq runs to achieve greater than 100× average coverage per each of the 19,200 clones. In other words, each of these metagenomic clones is theoretically represented within 3 different pools (column, plate and row) and by bioinformatically comparing these different sequenced library pools we can identify the gene content and exact library well location for each clone (manuscript in preparation). The pooled sequences were processed to achieve high quality sequence reads and generate assembled, contiguous genomic fragments (contigs). In a preliminary search for microbial genomic regions involved in pectin-related functions, we searched for gene sequences related to the degradation, uptake or utilization of pectin and pectin (or pectate)-derived sugars. Interestingly, we discovered 75 unique metagenomic contigs that had significant ($E<10^{-5}$) homology with a *Bacteroides* pectate lyase gene, and when each of these gene homologs were queried against the GenBank database these gave a mean % amino acid identity of 62%, and only one metagenome-derived gene had a % identity greater than 90%. Several hundred unique contigs were also identified that have homology with pectin-derived sugar uptake or utilization genes (data not shown). Collectively, this indicates that there is a wealth of previously undiscovered diversity of pectin-associated functions among soil microorganisms.

Sequencing of the BAC Clones Containing Pectin-Related Functions:

Each of the BAC clones identified by querying using known pectin-related gene sequences (including each gene known to be required for pectin degradation, uptake and utilization) will be identified for its exact location within the soil metagenomic library from a local BLAST search against each of the respective pool of clones (plate, column and row). To validate that the correct clone has been identified, the respective *E. coli* BAC clone will be grown for isolated colonies onto LB medium containing 12.5 µg per ml chloramphenicol and then a clone-specific primer set will be designed and used to PCR amplify a small genetic region unique to each clone (<500 bp). Each validated BAC clone will then be bar-coded using a Nextera kit and included within a HiSeq run in order to generate a complete insert sequence for each clone. The clone insert will be generated by trimming the sequence reads and de novo assembled using the CLC Genomics Workbench, and then the clone contigs will be submitted to the RAST automated pipeline for annotation. We will also manually annotate clones to examine the predicted functions and related genes present on each genomic region. We will conduct comparative genomic analyses to examine pathways related to pectin degradation, uptake and utilization from diverse soil microorganisms, deposit these sequences in GenBank for public access, and compare these sequences to those obtained from the SIP results (from the same soil) in order to link transcriptome data within a larger genomic context. Because the sequences obtained from the transcriptome analysis are expected to be short contigs all less than ~5 kb, the availability of genomic contigs >100 kb from the same soil will enable linking encoded functions from abundant and metabolically active soil microorganisms that metabolize pectin.

Expected Results:

A culture-independent metagenomic analysis of the pectin-utilizing genes recovered from soil microorganisms. This will result in a unique dataset of large genomic regions recovered from microorganisms from the same soil used for transcriptome analysis.

Anticipated Problems and their Solutions:

Much of the research has already been completed in order to construct the soil metagenomic library and to generate an exhaustive sequence database from column, plate and row pools. This objective is therefore very low risk because we already know that there are diverse pectinolytic functions encoded within the library that can be accessed, sequenced, and compared to the transcriptome data generated in Objective 3A.

Broader Inroads

We expect that this research will provide: 1) New beneficial microbial cultures that can be used to promote plant growth in many agricultural crops. These cultures may have novel plant interactions and produce metabolites that promote plant growth and/or control plant pathogens. 2) The cost-effective application of pectin as a soil amendment in order to enhance microbial plant growth promotion. Field application of PGPR strains is often ineffective, and we expect that the use of pectin will promote better efficacy and result in improvement in PGPR-mediated biological effects. Our study will evaluate cost-effective pectin-rich soil amendments that could be used for agricultural application of this technology. 3) New insights into root pectin-utilizing microbes and their plant-related functions. Through the use of culture-independent approaches we will provide information on the diversity of pectin-utilizing microbes, the plant-related functions they express and provide a database of their genomic regions associated with pectin use. 4) We will provide educational opportunities as a component of this research.

REFERENCES

1. Walakira J K, Carrias A A, Hossain M J, Jones E, Terhune J S, & Liles M R (2008) Identification and characterization of bacteriophages specific to the catfish pathogen, Edwardsiella ictaluri. Journal of Applied Microbiology 105(6):2133-2142.
2. Carrias A, Welch T J, Waldbieser G C, Mead D A, Terhune J S, & Liles M R (2011) Comparative genomic analysis of bacteriophages specific to the channel catfish pathogen Edwardsiella ictaluri. Virology Journal 8.
3. Ran C, Carrias A, Williams M A, Capps N, Dan B C T, Newton J C, Kloepper J W, Ooi E L, Browdy C L, Terhune J S, & Liles M R (2012) Identification of *Bacillus* Strains for Biological Control of Catfish Pathogens. PloS One 7(9).
4. Chander Y, Koelbl J, Puckett J, Moser M J, Klingele A J, Liles M R, Carrias A, Mead D A, & Schoenfeld T W (2014) A novel thermostable polymerase for RNA and DNA loop-mediated isothermal amplification (LAMP). Frontiers in Microbiology 5:395.
5. Pascale B. Beauregard Y C, Hera Vlamakis, Richard Losick, and Roberto Kolter (2013) *Bacillus subtilis* biofilm induction by plant polysaccharides PNAS 110(17): E1621-E1630.
6. Hossain M J, Sun D W, McGarey D J, Wrenn S, Alexander L M, Martino M E, Xing Y, Terhune J S, & Liles M R (2014) An Asian Origin of Virulent *Aeromonas hydrophila* Responsible for Disease Epidemics in United States-Farmed Catfish. mBio 5(3).
7. Hossain M J, Ran C, Liu K, Ryu C M, Rasmussen-Ivey C R, Williams M A, Hassan M K, Choi S K, Jeong H, Newman M, Kloepper J W, & Liles M R (2015) Deciphering the conserved genetic loci implicated in plant disease control through comparative genomics of *Bacillus amyloliquefaciens* subsp *plantarum*. Frontiers in Plant Science 6.
8. Raupach G S & Kloepper J W (1998) Mixtures of plant growth-promoting rhizobacteria enhance biological control of multiple cucumber pathogens. Phytopathology 88(11):1158-1164.
9. Adesemoye A O, Torbert H A, & Kloepper J W (2009) Plant Growth-Promoting Rhizobacteria Allow Reduced Application Rates of Chemical Fertilizers. Microbial Ecology 58(4):921-929.
10. Yan Z N, Reddy M S, Ryu C M, McInroy J A, Wilson M, & Kloepper J W (2002) Induced systemic protection against tomato late blight elicited by plant growth-promoting rhizobacteria. Phytopathology 92(12):1329-1333.
11. Ryu C M, Murphy J F, Mysore K S, & Kloepper J W (2004) Plant growth-promoting rhizobacteria systemically protect *Arabidopsis thaliana* against Cucumber mosaic virus by a salicylic acid and NPR1-independent and jasmonic acid-dependent signaling pathway. Plant Journal 39(3):381-392.
12. Compaore C S, Nielsen D S, Sawadogo-Lingani H, Berner T S, Nielsen K F, Adimpong D B, Diawara B, Ouedraogo G A, Jakobsen M, & Thorsen L (2013) *Bacillus amyloliquefaciens* ssp *plantarum* strains as potential protective starter cultures for the production of Bikalga, an alkaline fermented food. Journal of Applied Microbiology 115(1):133-146.

13. Avdeeva L V, Dragovoz I V, Korzh Iu V, Leonova N O, Iutinskaia G A, Berezhnaia A V, Kuptsov V N, Mandrik M N, & Kolomiets E I (2014) [Antagonistic activity of *Bacillus amyloliquefaciens* subsp. *plantarum* IMV B-7404 and BIM B-439D strains towards pathogenic bacteria and micromycetes]. Mikrobiol Z 76(6):27-33.
14. Calvo P, Nelson L, & Kloepper J W (2014) Agricultural uses of plant biostimulants. Plant Soil 383(1-2):3-41.
15. Bashan Y, de-Bashan L E, Prabhu S R, & Hernandez J P (2014) Advances in plant growth-promoting bacterial inoculant technology: formulations and practical perspectives (1998-2013). Plant Soil 378(1-2):1-33.
16. Zaidi S, Usmani S, Singh B R, & Musarrat J (2006) Significance of *Bacillus subtilis* strain SJ-101 as a bioinoculant for concurrent plant growth promotion and nickel accumulation in *Brassica juncea*. Chemosphere 64(6):991-997.
17. He P F, Hao K, Blom J, Rueckert C, Vater J, Mao Z C, Wu Y X, Hou M S, He P B, He Y Q, & Borriss R (2013) Genome sequence of the plant growth promoting strain *Bacillus amyloliquefaciens* subsp *plantarum* B9601-Y2 and expression of mersacidin and other secondary metabolites. Journal of Biotechnology 164(2):281-291.
18. Mariappan A, Makarewicz O, Chen X H, & Borriss R (2012) Two-Component Response Regulator DegU Controls the Expression of Bacilysin in Plant-Growth-Promoting Bacterium *Bacillus amyloliquefaciens* FZB42. Journal of molecular microbiology and biotechnology 22(2):114-125.
19. Blom J, Rueckert C, Niu B, Wang Q, & Borriss R (2012) The Complete Genome of *Bacillus amyloliquefaciens* subsp *plantarum* CAU B946 Contains a Gene Cluster for Nonribosomal Synthesis of Iturin A. Journal of Bacteriology 194(7):1845-1846.
20. Ravu R R, Jacob M R, Chen X L, Wang M, Nasrin S, Kloepper J W, Liles M R, Mead D A, Khan I A, & Li X C (2015) Bacillusin A, an Antibacterial Macrodiolide from *Bacillus amyloliquefaciens* AP183. Journal of natural products 78(4):924-928.
21. Altinok H H, Dikilitas M, & Yildiz H N (2013) Potential of *Pseudomonas* and *Bacillus* Isolates as Biocontrol Agents against *Fusarium* Wilt of Eggplant. Biotechnol Biotec Eq 27(4):3952-3958.
22. Kloepper J W, Ryu C M, & Zhang S A (2004) Induced systemic resistance and promotion of plant growth by *Bacillus* spp. Phytopathology 94(11):1259-1266.
23. Kloepper J W (1994) Plant-growth-promoting rhizobacteria (other systems). *Azospirillum*/plant associations, ed Okon Y (CRC Press, Boca Raton), pp 139-154.
24. Handelsman J & Stabb E V (1996) Biocontrol of soilborne plant pathogens. The Plant Cell 8(10):1855-1869.
25. Hawes M C, Brigham L A, Wen F, Woo H H, & Zhu Z (1998) Function of root border cells in plant health: Pioneers in the rhizosphere. Annual Review of Phytopathology 36:311-327.
26. Anonymous (2013) Biostimulants market—By Active Ingredients, Applications, Crop Types & Geography—Global Trends & Forecasts to 2018.
27. H. B (1825) Recherches sur un Nouvel Acide Universellement Répandu Dans Tous les Végétaux. Annales de Chimie et de Physique (French) 28:173-178.
28. Anonymous. Plant Cell walls. (University of Georgia, USA), Complex Carbohydrate Research Center.
29. Darvill A, McNeil M, Albersheim P, & Delmer D (1980) The primary cell walls of flowering plants. The Biochemistry of Plants 1:91-162.
30. Srivastava P & Malviya R (2011) Sources of pectin, extraction and its applications in pharmaceutical industry—An overview. Indian Journal of Natural Products and Resources 2(1):10-18.
31. Muller K, Levesque-Tremblay G, Bartels S, Weitbrecht K, Wormit A, Usadel B, Haughn G, & Kermode A R (2013) Demethylesterification of Cell Wall Pectins in *Arabidopsis* Plays a Role in Seed Germination. Plant physiology 161(1):305-316.
32. Stephenson M B & Hawes M C (1994) Correlation of Pectin Methylesterase Activity in Root Caps of Pea with Root Border Cell-Separation. Plant Physiology 106(2): 739-745.
33. Cai M Z, Wang N, Xing C H, Wang F M, Wu K, & Du X (2013) Immobilization of aluminum with mucilage secreted by root cap and root border cells is related to aluminum resistance in *Glycine max* L. Environ Sci Pollut R 20(12):8924-8933.
34. Miyasaka S C & Hawes M C (2001) Possible role of root border cells in detection and avoidance of aluminum toxicity. Plant Physiology 125(4):1978-1987.
35. Jayani R S, Saxena S, & Gupta R (2005) Microbial pectinolytic enzymes: A review. Process Biochem 40(9): 2931-2944.
36. Ashwell G, Wahba A J, & Hickman J (1960) Uronic acid metabolism in bacteria. I. Purification and properties of uronic acid isomerase in *Escherichia coli*. The Journal of Biological Chemistry 235:1559-1565.
37. Zucker M, Sands D, & Hankin L (1972) Factors Governing Pectate Lyase Synthesis in Soft Rot and Non-Soft Rot Bacteria. Physiol Plant Pathol 2(1):59-&.
38. Mekjian K R, Bryan E M, Beall B W, & Moran C P (1999) Regulation of hexuronate utilization in *Bacillus subtilis*. Journal of Bacteriology 181(2):426-433.
39. Hugouvieux-Cotte-Pattat N, Nasser W, & Robert-Baudouy J (1994) Molecular characterization of the *Erwinia chrysanthemi* kdgK gene involved in pectin degradation. Journal of Bacteriology 176(8):2386-2392.
40. Mehanni M M a cM, H. A. (2012) Effect of raw pectin amendment on the survival and proliferation of *Azospirillum* in non-sterile soil. Egypt Journal of Botany 2nd International Conference, pp 99-111.
41. Xie F, Murray J D, Kim J, Heckmann A B, Edwards A, Oldroyd G E D, & Downie A (2012) Legume pectate lyase required for root infection by *rhizobia*. Proceedings of the National Academy of Sciences of the United States of America 109(2):633-638.
42. Simon H M, Jahn C E, Bergerud L T, Sliwinski M K, Weimer P J, Willis D K, & Goodman R M (2005) Cultivation of mesophilic soil crenarchaeotes in enrichment cultures from plant roots. Applied and Environmental Microbiology 71(8):4751-4760.
43. Sunnotel O & Nigam P (2002) Pectinolytic activity of bacteria isolated from soil and two fungal strains during submerged fermentation. World Journal of Microbiology & Biotechnology 18(9):835-839.
44. Soriano M, Diaz P, & Pastor F I (2005) Pectinolytic systems of two aerobic sporogenous bacterial strains with high activity on pectin. Current Microbiology 50(2):114-118.
45. Nichols D, Cahoon N, Trakhtenberg E M, Pham L, Mehta A, Belanger A, Kanigan T, Lewis K, & Epstein S S (2010) Use of Ichip for High-Throughput In Situ Cultivation of "Uncultivable" Microbial Species. Applied and Environmental Microbiology 76(8):2445-2450.
46. George I F, Hartmann M, Liles M R, & Agathos S N (2011) Recovery of As-Yet-Uncultured Soil Acidobacte- 46. ria on Dilute Solid Media. Applied and Environmental Microbiology 77(22):8184-8188.
47. Sakai T, Sakamoto T, Hallaert J, & Vandamme E J (1993) Pectin, Pectinase, and Protopectinase—Production, Properties, and Applications. Advances in Applied Microbiology, Vol 39 39:213-294.
48. Yang J L, Li Y Y, Zhang Y J, Zhang S S, Wu Y R, Wu P, & Zheng S J (2008) Cell wall polysaccharides are specifically involved in the exclusion of aluminum from the rice root apex. Plant Physiology 146(2):602-611.
49. Neidhard. Fc, Bloch P L, & Smith D F (1974) Culture Medium for Enterobacteria. Journal of Bacteriology 119 (3):736-747.
50. Charles C. Mitchell D D, and Kipling S. Balkcom (2005) Cullars Rotation: The South's Oldest Continuous Soil Fertility Experiment. Better Crops 89(4):5-9.
51. Stackebrandt E & Goodfellow M (1991) Nucleic acid techniques in bacterial systematics (Wiley, Chichester; New York) pp xxix, 329 p.
52. De Beeck M O, Lievens B, Busschaert P, Declerck S, Vangronsveld J, & Colpaert J V (2014) Comparison and Validation of Some ITS Primer Pairs Useful for Fungal Metabarcoding Studies. PloS One 9(6).
53. Vancov T & Keen B (2009) Amplification of soil fungal community DNA using the ITS86F and ITS4 primers. FEMS Microbiology Letters 296(1):91-96.
54. Stamatakis A (2014) RAxML version 8: a tool for phylogenetic analysis and post-analysis of large phylogenies. Bioinformatics 30(9):1312-1313.
55. Newman M M, Feminella, J. W., and Liles, M. R. (2010) Purification of genomic DNA from environmental sources for use in a polymerase chain reaction. Cold Spring Harbor Protocols.
56. Talboys P J, Owen D W, Healey J R, Withers P J A, & Jones D L (2014) Auxin secretion by *Bacillus amyloliquefaciens* FZB42 both stimulates root exudation and limits phosphorus uptake in *Triticum aestivum*. BMC Plant Biology 14.
57. Heisler M G, Ohno C, Das P, Sieber P, Reddy G V, Long J A, & Meyerowitz E M (2005) Patterns of auxin transport and gene expression during primordium development revealed by live imaging of the *Arabidopsis* inflorescence meristem. Current Biology 15(21):1899-1911.
58. Zurcher E, Tavor-Deslex D, Lituiev D, Enkerli K, Tan P T, & Muller B (2013) A Robust and Sensitive Synthetic Sensor to Monitor the Transcriptional Output of the Cytokinin Signaling Network in Planta. Plant Physiology 161(3):1066-1075.
59. Rashotte A M, Mason M G, Hutchison C E, Ferreira F J, Schaller G E, & Kieber J J (2006) A subset of *Arabidopsis* AP2 transcription factors mediates cytokinin responses in concert with a two-component pathway. Proceedings of the National Academy of Sciences of the United States of America 103(29):11081-11085.
60. Gonzalez A J, Rodicio M R, & Mendoza M C (2003) Identification of an emergent and atypical *Pseudomonas viridiflava* lineage causing bacteriosis in plants of agronomic importance in a Spanish region. Applied and Environmental Microbiology 69(5):2936-2941.
61. Liu G, Song L, Shu C, Wang P, Deng C, Peng Q, Lereclus D, Wang X, Huang D, Zhang J, & Song F (2013) Complete genome sequence of *Bacillus thuringiensis* subsp. kurstaki strain HD73. Genome announcements 1(2):e0008013.
62. Codling A J & Woodman H E (1929) Sugar-beet pulp as a source of pectin. J Agr Sci 19:701-714.
63. Durand C, Vicre-Gibouin M, Follet-Gueye M L, Duponchel L, Moreau M, Lerouge P, & Driouich A (2009) The Organization Pattern of Root Border-Like Cells of *Arabidopsis* Is Dependent on Cell Wall Homogalacturonan. Plant Physiology 150(3):1411-1421.
64. Bouton S, Leboeuf E, Mouille G, Leydecker M T, Talbotec J, Granier F, Lahaye M, Hofte H, & Truong H N (2002) Quasimodo1 encodes a putative membrane-bound glycosyltransferase required for normal pectin synthesis and cell adhesion in *Arabidopsis*. The Plant Cell 14(10): 2577-2590.
65. Mouille G, Ralet M C, Cavelier C, Eland C, Effroy D, Hematy K, McCartney L, Truong H N, Gaudon V, Thibault J F, Marchant A, & Hofte H (2007) Homogalacturonan synthesis in *Arabidopsis thaliana* requires a Golgi-localized protein with a putative methyltransferase domain. Plant Journal 50(4):605-614.
66. Krupkova E, Immerzeel P, Pauly M, & Schmulling T (2007) The TUMOROUS SHOOT DEVELOPMENT2 gene of *Arabidopsis* encoding a putative methyltransferase is required for cell adhesion and co-ordinated plant development. Plant Journal 50(4):735-750.
67. Daher F B & Braybrook S A (2015) How to let go: pectin and plant cell adhesion. Frontiers in Plant Science 6.
68. Fierer N, Breitbart M, Nulton J, Salamon P, Lozupone C, Jones R, Robeson M, Edwards R A, Felts B, Rayhawk S, Knight R, Rohwer F, & Jackson R B (2007) Metagenomic and small-subunit rRNA analyses reveal the genetic diversity of bacteria, archaea, fungi, and viruses in soil. Applied and Environmental Microbiology 73(21):7059-7066.
69. Verastegui Y, Cheng J, Engel K, Kolczynski D, Mortimer S, Lavigne J, Montalibet J, Romantsov T, Hall M, McConkey B J, Rose D R, Tomashek J J, Scott B R, Charles T C, & Neufeld J D (2014) Multisubstrate Isotope Labeling and Metagenomic Analysis of Active Soil Bacterial Communities. mBio 5(4).
70. Whiteley A S, Thomson B, Lueders T, & Manefield M (2007) RNA stable-isotope probing. Nature Protocols 2(4):838-844.
71. Lueders T, Manefield M, & Friedrich M W (2004) Enhanced sensitivity of DNA- and rRNA-based stable isotope probing by fractionation and quantitative analysis of isopycnic centrifugation gradients. Environmental Microbiology 6(1):73-78.
72. Green S J, Venkatramanan R, & Naqib A (2015) Deconstructing the Polymerase Chain Reaction: Understanding and Correcting Bias Associated with Primer Degeneracies and Primer-Template Mismatches. PloS One 10(5).
73. Liles M R, Williamson L L, Rodbumrer J, Torsvik V, Goodman R M, & Handelsman J (2008) Recovery, purification, and cloning of high-molecular-weight DNA from soil microorganisms. Appl Environ Microbiol 74(10): 3302-3305.

Example 5—Proposal: Enhancing Fish Nutrition, Growth Performance and Disease Resistance in Fish Using a Probiotic *Bacillus* and Prebiotic Pectin Project Summary Aquaculture sustainability is threatened by disease pressure and the eutrophic conditions resulted from intensive fish farming. Previous research conducted separately at Auburn University and at Ocean University-Qingdao has resulted in the identification of *Bacillus amyloliquefaciens* (now *B. velezensis*) strains that have the ability to reduce mortality due to multiple aquaculture pathogens. Studies in aquaria and ponds have determined that feeding fish with *B. amyloliquefaciens* (now *B. velezensis*) probiotic-amended feed can enhance catfish growth performance resulting in a 8-14% increase in final weight as compared to control fish. Interestingly, in the pond study there was also an observed improvement in water quality in ponds in which fish were fed with the probiotic-amended feed, as significant reductions were found in pond water total phosphorus (19%), total nitrogen (43%), and nitrate (75%), along with reduced levels of chlorophyll and 2-methylisoborneol. Recent insights into the genetics and physiology of the *B. amyloliquefaciens* (now *B. velezensis*) probiotic strains indicates that these bacteria can use plant-derived pectin as a carbon and energy source. Because aquaculture feeds are plant-based, and these probiotic bacteria were derived from plant rhizospheres, the use of plant carbohydrates like pectin by the probiotic bacteria is expected to enhance probiotic-mediated effects such as feed conversion efficiency and the production of secondary metabolites that antagonize aquaculture pathogens. This proposal will evaluate the hypothesis that this synbiotic approach, the addition of a probiotic *Bacillus* together with the prebiotic pectin to fish feed, will result in improved fish growth performance and reduced mortality due to infection with an aquaculture pathogen compared to fish fed with a control diet or with the probiotic or prebiotic alone.

Project Narrative and Justification

Due to their rapid growth rate, low cost, and proficient reproduction capabilities, catfish species including the channel catfish (*Ictalurus punctatus*) in the United States and the Southern catfish (*Silurus meridionalis* Chen) in the People's Republic of China has become one of the more popular and economically important aquaculture species, particularly in the southeastern United States (USDA, 2003a; USDA 2003b). For maximized productivity of the aquaculture system, fish feeding efficiency is extremely important. Traditionally, forage fisheries have been exploited for generation of fish meal, but the rapid depletion of wild fisheries (Naylor et al, 2009) has led to the use of soy meal as an alternative (Tacon, 1987; NRC, 2011). However, feed conversion ratios (FCR) are much lower in fish with the use of plant protein resulting in up to a 15% deterioration of fish growth performance (Sales, 2008). Due to the presence of 1-2% phytate content in soy-based feed, over two-thirds of the phosphorous found in plant protein sources are unusable by fish, and phytate can serve as an anti-nutrient in binding iron resulting in anemia (Zhu, 2014). Unused phytate will ultimately be released as fish waste, contributing to the eutrophication of the aquaculture pond ecosystem (Lazzari, 2008).

Eutrophication due to indigestible components of the feed and excreted nutrients can result in blooms of algae and cyanobacteria (Shaw et al, 2003). Due to the ability of Cyanobacteria taxa to synthesize and release toxins into the water column, they can be devastating to fish production (Rodgers, 2008). In addition to hepatotoxins and neurotoxins, some Cyanobacteria and other bacterial taxa produce the metabolites 2-methylisoborneol (MIB) and geosmin that result in off-flavors in catfish (Tucker and Ploeg, 1999).

Phytase is a phosphohydrolase that catalyses the hydrolysis of phytate, allowing for phosphorous availability for absorption (Kumar et al., 2012). This enzyme is found in many microorganisms, which are being exploited for supplementation in feed. To supplement high feed demands, production facilities have been created to exponentially ferment phytase from microorganisms, many of which are already regarded as probiotics (Askelson et al, 2014). For this reason, providing the fish probiotics in their diet can potentially reduce eutrophication, induce weight gain, and be a viable option for preventing economic loss. Probiotic bacteria may promote the growth of fish by improving feed nutrient quality and by removing anti-nutrients such as phytate. Some microorganisms express phytase activity, catalyzing phytate hydrolysis and allowing for phosphorous absorption (Kumar et al., 2011). Purified microbial phytases have been used as a feed additive in fish feeds to promote growth and reduce eutrophication (Kumar et al 2012)). For this reason, feeding fish with a phytase-expressing probiotic could be a sustainable management practice to reduce eutrophication, induce weight gain, and result in an altered aquaculture pond ecosystem with reduced incidence of disease and off-flavor.

Another factor responsible for significant economic losses in aquaculture is due to loss from disease (FDA, 2012). One traditional treatment for disease is the use of antibiotics, and there are currently three approved by the FDA for use in aquaculture production facilities (FDA, 2011). However, with growing concern over the use of antibiotics due to the development of resistance in pathogens, it is important to seek alternative means of treatment. Probiotics can reduce mortality due to pathogens by direct antagonism via synthesis of secondary metabolites, by competitive exclusion, and by activation of the innate immune system (Balcazar, 2006; Macfarlane, 1999 Wang, 2008). *Bacillus* spp. have good potential for aquaculture application due to their ability to form endospores, allowing for a long shelf life and survival of gastric acid (Casula, 2002; Hong, 2005; Hyronimus, 2000). Furthermore, strains within the *B. subtilis* group, which includes *B. amyloliquefaciens*, have not been associated with disease.

Previous research at Auburn University by the PIs evaluated a collection of 160 *Bacillus* spp. strains for their antimicrobial activity against bacterial and fungal fish pathogens (Ran et al., 2012). The 21 *Bacillus* spp. strains that showed production of secondary metabolites that inhibited the growth of Edwardsiella ictaluri, Aeromonas hydrophila and other pathogens were then tested for their survival and persistence in the catfish intestine and protection against E. ictaluri infection (Ran et al., 2012). When *Platydoras armatulus* (striped catfish) were fed with spore-amended feed significant reductions in mortality relative to the control group was observed after challenge with E. ictaluri (Ran et al., 2012).

The four best-performing *Bacillus* spp. (now *B. velezensis*) strains (AB01, AP79, AP143 and AP193) were selected for further study for their potential for disease control and fish growth promotion. All four strains were found to be affiliated with *B. amyloliquefaciens* (now *B. velezensis*) based on phylogenetic analyses (Hossain et al., 2015), without any virulence-related genetic determinants (data not shown). Each of these *B. amyloliquefaciens* (now *B. velezensis*) strains was evaluated separately for their relative degree of channel catfish growth promotion and biocontrol activity. Feed amended with *B. amyloliquefaciens* (now *B. velezensis*) AP193 provided the greatest degree of fish growth promotion in both replicated aquaria and pond studies, with a 8.5% ($P<0.05$) or 21.8% ($P<0.1$) increase in the average weight gain per fish compared to fish fed with control feed in aquaria and pond studies, respectively. Furthermore, the fish fed with strain AP193 had a mortality due to E. ictaluri infection of 47.8% compared to the 62.1% mortality rate for fish fed with control feed (($P<0.05$). It was previously observed that strain AP193 expresses the antibiotic difficidin and that the production of this polyketide is critical for AP193 biocontrol activity in plants (Hossain et al., 2015). We have observed that strain AP193 mutants deficient in difficidin synthesis (☐sfp or ☐dfnD) were also completely lacking in the ability to inhibit the in vitro growth of bacterial fish pathogens such as E. ictaluri and A. hydrophila (data now shown), further supporting the hypothesis that difficidin production is important for fish disease control while leaving open the possibility that other mechanisms (e.g. competitive exclusion, stimulation of immune competence) are also involved.

Together with the increase in catfish growth performance and reduction in fish mortality, significant reductions in total phosphorus, total nitrogen, and nitrate nitrogen levels were observed in ponds containing channel catfish fed with AP193-indicating beneficial, pond-wide effects on water quality (Table 5).

TABLE 5

Mean concentrations mg/L of water quality parameters in control ponds and ponds fed with AP193 amended feed.

| Water Quality Parameter | P-value | Control (Mean ± SD) | AP 193 Treatment (Mean ± SD) |
|---|---|---|---|
| Total Phosphorus | 0.014 | 0.136 ± 0.049a | 0.110 ± 0.066b |
| Total Nitrogen | 0.025 | 0.344 ± 0.248a | 0.195 ± 0.120b |
| Total Ammonia Nitrogen | 0.829 | 0.142 ± 0.065a | 0.137 ± 0.059a |
| Nitrite Nitrogen | 0.945 | 0.004 ± 0.004a | 0.004 ± 0.004a |
| Nitrate Nitrogen | 0.044 | 0.051 ± 0.095a | 0.013 ± 0.026b |

Excessive concentrations of N and P in ponds can contribute to dense cyanobacterial or algal blooms that induce toxic eutrophication and fish "off-flavor" (Boyd, 2015). Soy-based fish feed contains high levels of phytate, which is inositol-hexaphosphate (Cao, 2007; Storebakken, 1998). B. amyloliquefaciens (now B. velezensis) AP193 is known to encode a phytase (Hossain et al., 2015) and has been observed to express phytase activity (data not shown). Thus, AP193 has the capacity to degrade the phytate present within feed, resulting in more iron availability to support fish growth as well as decreasing phosphate excreted from fish, thereby preventing the release of phosphorus into the water that can result in eutrophication. Furthermore, previous research has determined that A. hydrophila has the ability to use myo-inositol as a sole C source and suggests that the presence of high levels of inositol in the diet could contribute to A. hydrophila pathogenesis (Hossain et al., 2013). By expressing a phytase activity, strain AP193 may be improving not only fish growth and water quality, but also removing a key nutrient (inositol) that may contribute to A. hydrophila pathogenesis. This study will therefore investigate the benefit of feeding fish with feed amended with AP193 in reducing mortality associated with virulent A. hydrophila that is known to cause severe losses to the aquaculture industries in China and the United States (Rasmussen-Ivey et al., 2016).

The probiotic effects observed to date support the potential benefit of this strategy for improving the sustainability of fish farming in China and the United States. While promising, there is inherent variability in the water quality and microbiology associated with aquaculture practices in both countries, and there is a need to increase the efficacy of probiotics so that they can perform under various conditions. Our previous genomic study that investigated the predicted functions associated with these probiotic strains found that one trait that the B. amyloliquefaciens (now B. velezensis) strains have in common is the ability to use the plant carbohydrate pectin as a carbon and energy source (Hossain et al., 2015). We subsequently found that the ability to use pectin-derived sugars was a universal characteristic of the 59 B. amyloliquefaciens (now B. velezensis) strains that had been used to promote the growth of plants (Adesemoye et al., 2009) and/or fish (Ran et al., 2012) in the Auburn collection. This led to the hypothesis that adding pectin to the fish diet could enhance the growth of the probiotic bacteria and thereby improve fish growth performance, water quality, and disease resistance. We have now tested this hypothesis in soybean model together with Prof. Joseph Kloepper (Auburn University), and have observed a strong synergy between B. amyloliquefaciens strains and pectin, resulting in statistically significant increases in soybean root and shoot weight (data not shown). The soybean root enhancement using bacterial and pectin amendment was observed with multiple B. amyloliquefaciens (now B. velezensis) strains, including strain AP193, with significant root growth and nodulation enhancement observed when both bacterial spores and pectin were added together compared to the bacterial treatment alone (FIGS. 3 and 4), and no effect on root growth was observed when pectin was applied alone (data not shown).

Objective

This proposal will test the ability of pectin as a prebiotic to enhance the probiotic effects we have previously established in catfish, which is referred to as a "synbiotic" approach. Specifically, different dosage rates of pectin incorporated into the diet will be evaluated as to how probiotics respond to this addition in the diet and by promoting fish survival after bacterial challenge with virulent Aeromonas hydrophila. This could directly benefit the sustainability and productivity of aquaculture as practiced in both China and the United States.

Experimental Design:

Parallel studies will be carried out in the US and China using Channel Catfish and the Southern catfish in conjunction with specific strains of B. amyloliquefaciens (now B. velezensis). All trials will be designed to determine the efficacy of select prebiotic and probiotic combinations on growth, nutrient retention and disease resistance under controlled conditions.

Aquaria Trials:

At both institutes a commercial type basal plant-based diet will be formulated and produced in house using typical feed manufacturing methods. The basal diet will then be modified by adding graded level of pectin and suitable levels of the probiotic. The test diets will then be offered to five replicate groups (15-20 fish/tank) of juvenile fish over a 10-week culture period. The fish will be offered feed twice daily at a level approximating satiation. The fish will be maintained in a re-circulating culture system designed to maintain suitable water quality parameters. Each system will consist of culture tank, UV sterilization of water, solids filtration, biological filtration, circulation pump and supplemental aeration. At the conclusion of the growth trial survival, final weight, thermal growth coefficient, percent weight gain and feed conversion efficiency will be determined. Additionally, a sub-sample of fish will be analyzed for proximate composition using standard AOAC procedures and the date used to determine apparent net protein, phosphorus and iron retention. Meanwhile, the intestinal morphology will be analyzed, including the dimensions of both jejunum wall thickness and villus height in different groups.

TABLE 6

Aquaria Trials

| | Channel Catfish (US) | | Southern Catfish (China) | |
|---|---|---|---|---|
| | | B. amyloliquefaciens | | |
| Treatment | Diet type | AP193 | Diet type | B. amyloliquefaciens |
| 1 | Basal diet (BD) | | Basal diet (BD) | |
| 2 | BD + 0.05% pectin | | BD + 0.05% pectin | |
| 3 | BD + 0.10% pectin | | BD + 0.10% pectin | |
| 4 | BD + 0.50% pectin | | BD + 0.50% pectin | |
| 5 | Basal diet (BD) | $10^6$ CFU/g | Basal diet (BD) | $10^6$ CFU/g |
| 6 | BD + 0.05% pectin | $10^6$ CFU/g | BD + 0.05% pectin | $10^6$ CFU/g |
| 7 | BD + 0.10% pectin | $10^6$ CFU/g | BD + 0.10% pectin | $10^6$ CFU/g |
| 8 | BD + 0.50% pectin | $10^6$ CFU/g | BD + 0.50% pectin | $10^6$ CFU/g |

Disease Challenge with Virulent *A. hydrophila* ML09-119:

All fish will be transferred to the disease challenge laboratory maintaining fish within each replicate aquaria. Fish will be allowed to acclimate for one week while being offered the same treatment diet as above. The fish will then be challenged by immersion with vAh using an immersion protocol developed by the USDA-ARS in which fish have their adipose fin clipped and are then immersed in $10^7$ CFU/ml vAh for 1 hr, typically resulting in ~50% mortality within 24 hrs. The percent mortality in each treatment group will be determined and confirmed with representative vAh cases using a vAh-specific diagnostic tests. Statistical comparisons among treatment groups will be conducted with one-way ANOVAs with significance assessed at P<0.05.

Timeline of Events:

At about 0-5 months, the growth and disease experimental trial will be performed. At about 4-9 months, tissue and histological preparation and evaluation will be performed. At about 10-12 months, data analysis and report preparation will be performed Expected Results and Outcomes As pectin levels are increased within diets containing the probiotic, we expect higher growth rates and feed conversion efficiency, along with better survival after pathogen challenge as a result of increased proliferation of the probiotic and increased production of probiotic-derived secondary metabolites (e.g. difficidin) within the intestines. We do not anticipate any affect on growth performance or survival upon bacterial challenge due to pectin being in diet alone. Additionally, we do not anticipate any adverse affects in the intestinal lining due to the increased levels of beneficial bacteria, being consistent with previous studies conducted in our laboratories.

REFERENCES

Adesemoye A O, Torbert H A, & Kloepper J W (2009) Plant Growth-Promoting Rhizobacteria Allow Reduced Application Rates of Chemical Fertilizers. Microbial Ecology 58(4):921-929.

APHIS. (2003) Off-flavor in U. S. catfish operations. USDA: Animal and Plant Health Inspection Service. Veterinary Services.

Askelson, T. E., Campasino, A., Lee, J. T., Duong, T. (2014) Evaluation of phytate-degrading *Lactobacillus* culture administration to broiler chickens. Appl. Environ. Microbiol., 80, 943-950.

Balcazar, J. L., de Blas, I., Ruiz-Zarzuela, I., Cunningham, D., Vendrell, D. and Muzquiz, J. L. (2006) The role of probiotics in aquaculture. Vet Microbiol 114, 173-186.

Benson D. A., Karsch-Mizrachi I., Lipman D. J., Ostell J., Sayers E. W. (2009) GenBank. Nucleic Acids Res. 2009 January; 37(Database issue):D26-31. Epub 2008 Oct. 21.

Bower, C. E., Holm-Hansen, T., (1980) A Salicylate-hypochlorite Method for Determining Ammonia in Seawater. Can. J. Fish. Aquat. Sci. 37, 794-798.

Boyd, C. E. (2015) Water Quality, An Introduction, $2^{nd}$ Edition. Springer, New York, N.Y., USA.

Boyd, C. E., Tucker C. S. (1992) Water Quality and Pond Soil Analyses for Aquaculture. Alabama Agricultural Experiment Station, Auburn University: Auburn University, Alabama.

Cao, L., Wang, W., Yang, C., Yang, Y., Diana, J., Yakupitiyage, A., Luo, Z., Li, D. (2007) Application of microbial phytase in fish feed. Enzyme and Microbial Technology: 40: 4.

Caporaso J. G., Bittinger K., Bushman F. D., DeSantis T. Z., Andersen G. L., Knight R. (2010) PyNAST: a flexible tool for aligning sequences to a template alignment. Bioinformatics 26:266-267.

Caporaso J. G., Kuczynski J., Stombaugh J., Bittinger K., Bushman F. D., Costello E. K., Fierer N., Gonzalez Pena A., Goodrich J. K., Gordon J. I., Huttley G. A., Kelley S. T., Knights D., Koenig J. E., Ley R. E., Lozupone C. A., McDonald D., Muegge B. D., Pirrung M., Reeder J., Sevinsky J. R., Turnbaugh P. J., Walters W. A., Widmann J., Yatsunenko T., Zaneveld J., Knight R. (2010) QIIME allows analysis of high-throughput community sequencing data. Nature Methods 7(5): 335-336.

Casula G., Cutting S. M. (2002) *Bacillus* probiotics: spore germination in the gastrointestinal tract. Appl Environ Microbiol 68: 2344-2352.

Cole, J. R., Chai, B., Marsh, T. L., Farris, R. J., Wang, Q., Kulam, S. A., Tiedje, J. M. (2003) The Ribosomal Database Project (RDP-II): previewing a new autoaligner that allows regular updates and the new prokaryotic taxonomy. *Nucleic Acids Research,* 31(1), 442-443.

DeSantis T. Z., Hugenholtz P., Larsen N., Rojas M., Brodie E. L., Keller K., et al. (2006) Greengenes, a chimera-checked 16S rRNA gene database and workbench compatible with ARB. Appl Environ Microb 72(7): 5069-5072.

Diana, J. S. (2009) Aquaculture and biodiversity conservation. Bioscience, 59(1): 27-38.

Eaton, A. d., Clesceri, L. S., Rice, R. W., Greenberg, A. E. (2005) Standard Methods for the Examination of Water and Wastewater, 21$^{st}$ edition. American Public Health Association, Washington, D C, USA.

Edgar R. C. (2010) Search and clustering orders of magnitude faster than BLAST. Bioinformatics 26(19):2460-2461.

FDA (2011) Aquaculture Drugs. In Fish and Fishery Products Hazards and Controls Guide ed. U. S. Department of Health and Human Services pp. 183-207. Washington, D C: FDA, Center for Food Safety and Applied Nutrition, Office of Food Safety.

FDA (2012) Animal Husbandry and Disease Control: Aquaculture. Silver Spring, Md.: U. S. Food and Drug Administration.

Garcia, S. M., Rosenberg, A. A. (2010) Food security and marine capture fisheries: characteristics, trends, drivers and future perspectives. Phil. Trans. R. Soc. B 2010 365 2869-2880; DOI: 10.1098/rstb.2010.0171.

Gross, A., Boyd, C. E., Seo, J. (1999) Evaluation of the ultraviolet spectrophotometric method for the measurement of total nitrogen in water. Journal of the World Aquaculture Society 30:388-393.

Hong H. A., Duc L. H., Cutting S. M. (2005) The use of bacterial spore formers as probiotics. FEMS Microbiol Rev 29: 813-835.

Hossain M J, Waldbieser G C, Sun D W, Capps N K, Hemstreet W B, Carlisle K, Griffin M J, Khoo L, Goodwin A E, Sonstegard T S, Schroeder S, Hayden K, Newton J C, Terhune J S, Liles M R (2013) Implication of Lateral Genetic Transfer in the Emergence of *Aeromonas hydrophila* Isolates of Epidemic Outbreaks in Channel Catfish. PLoS One 8.

Hossain M J, Ran C, Liu K, Ryu C M, Rasmussen-Ivey C R, Williams M A, Hassan M K, Choi S K, Jeong H, Newman M, Kloepper J W, Liles M R (2015) Deciphering the conserved genetic loci implicated in plant disease control through comparative genomics of *Bacillus amyloliquefaciens* subsp *plantarum*. Front Plant Sci 6.

Hyronimus B., Le Marrec C., Hadji Sassi A., Deschamps A. (2000) Acid and bile tolerance of spore-forming lactic acid bacteria. Int J Food Microbiol 61: 193-197.

Kenney, D. S. and Couch, T. L. (1981) Mass production of biological agents for plant disease, weed and insect control. In: Papavizas G C, editors. Biological Control in Crop Production BARC Symposium No. 5. Totowa, N.J.: Allenheld and Osmum. 143-150.

Kumar, V., Sinha, A. K., Makkar, H. P. S., Boeck, G. D., Becker, K. (2012) Phytate and phytase in fish nutrition. J. Anim. Physiol. Anim. Nutr., 96, 335-364.

Lazzari, R., Baldisserotto, B. (2008) Nitrogen and phosphorous waste in fish farming. B. Inst. Pesca, Sao Paulo, 34(4): 591-600.

Le, P. T. T., Boyd, C. E. (2012) Comparison of Phenate and Salicylate Methods for Determination of Total Ammonia Nitrogen in Freshwater and Saline Water. J. World Aquacult. Soc. 43, 885-889.

Li, M. H., Robinson, E. H. (2008) Feeding catfish in commercial ponds. SRAC, 181.

Macfarlane, G. T., & Cummings, J. H. (1999). Probiotics and prebiotics: can regulating the activities of intestinal bacteria benefit health? BMJ: British Medical Journal, 318(7189), 999-1003.

Merino, G., Barange, M., Blanchard, J. L. et al. (2012) Can marine fisheries and aquaculture meet fish demand from a growing human population in a changing climate? Global Environmental Change 22, 795-806.

Naylor, R. L., Hardy, R. W., Bureau, A. C. et al. (2009) Feeding aquaculture in an era of finite resources. PNAS, 106(36), 15103-15110

NRC. (2011) Nutrient requirements of fish and shrimp. Washington, D C: The National Academies Press.

Ran, C., Carrias A., Williams M. A., Capps N., Dan B. C. T., Newton, J. C., Kloepper, J. W., Ooi, E. L., Browdy, C. L., Terhune, J. S., Liles, M. R. (2012) Identification of *Bacillus* Strains for Biological Control of Catfish Pathogens. PLoS ONE 7(9): e45793. doi:10.1371/journal.pone.0045793

Rasmussen-Ivey, C., Hossain, M. J., Odom, S. E., Terhune, J. S., Hemstreet, W. G., Shoemaker, C. A., Zhang, D., Xu, D., Griffin, M. J., Liu, Y., Figueras, M. J., Santos, S. R., Newton, J. C. and Liles, M. R. Classification of a hypervirulent *Aeromonas hydrophila* pathotype responsible for epidemic outbreaks in warm-water fishes. Accepted for publication in Frontiers in Microbiology Rodgers, J. H. (2008) Algal Toxins in Pond Aquaculture. SRAC. 4605

Sales, J. (2009) The effect of fish meal replacement by soyabean products on fish growth: a meta-analysis. Brit J Nutr 102: 1709-1722.

Sayers E. W., Barrett T., Benson D. A., Bryant S. H., Canese K., Chetvernin V., Church D. M., DiCuccio M., Edgar R., Federhen S., Feolo M., Geer L. Y., Helmberg W., Kapustin Y., Landsman D., Lipman D. J., Madden T. L., Maglott D. R., Miller V., Mizrachi I., Ostell J., Pruitt K. D., Schuler G. D., Sequeira E., Sherry S. T., Shumway M., Sirotkin K., Souvorov A., Starchenko G., Tatusova T. A., Wagner L., Yaschenko E., Ye J. (2009) Database resources of the National Center for Biotechnology Information. Nucleic Acids Res. 2009 January; 37(Database issue):D5-15. Epub 2008 Oct. 21.

Shaw, G. R., Moore, D., Garnett, C. M. (2003) Eutrophication and algal blooms. In Aleksandar Sabljic (Ed.), Encyclopedia of Life Support Systems (EOLSS) (pp. 1-21) Oxford, UK: Eolss Publishers.

Storebakken, T., Shearer, K. D., Roem, A. J. (1998) Availability of protein, phosphorus and other elements in fish meal, soy-protein concentrate and phytase-treated soy-protein-concentrate-based diets to Atlantic salmon, *Salmo salar*. Aquacultue: 161: 1-4.

Tacon, A. G. J. (1987) The nutrition and feeding of farmed fish and shrimp—a training manual 1. the essential nutrients. FAO, GCP/RLA/075/ITA, Field Document 5/E Tucker, C. S., Ploeg, M. (1999) Managing off-flavor problems in pond-raised catfish. SRAC. 192

US Department of Agriculture, USDA (2003a) Part I: Reference of Fingerling Catfish Health and Production Practices in the United States. Fort Collins, Colo., USA: National Health Monitoring System.

US Department of Agriculture, USDA (2003b) Part II: Reference of Foodsize Catfish Health and Production Practices in the United States. Fort Collins, Colo., USA: National Health Monitoring System.

Van Rijn, J. (1993) Methods to Evaluate Water Quality in Aquaculture. Faculty of Aquaculture, The Hebrew University of Jerusalem, Rehovot, Israel (in Hebrew).

Wang Y. B., Li J. R., Lin J. (2008) Probiotics in aquaculture: challenges and outlook. Aquaculture 281: 1-4.

Zhu, Y., X. Qiu, Q. Ding, M. Duan and C. Wang, 2014. Combined effects of dietary phytase and organic acid on growth and phosphorus utilization of juvenile yellow catfish Pelteobagrus fulvidraco. Aquaculture. 430: 1-8.

It will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. An inoculant for a plant comprising: (a) *Bacillus velezensis* (BV), and (b) a saccharide comprising pectin or a pectin-related saccharide, wherein the pectin-related saccharide is a heteropolysaccharide comprising D-galacturonate monomers which represent at least 50% of all monomers of the heteropolysaccharide.

2. The inoculant of claim 1, wherein the saccharide is pectin having an average molecular weight of at least about 30000 g/mol.

3. The inoculant of claim 1, further comprising a nitrogen-fixing bacteria.

4. A plant seed coated with the inoculant of claim 1.

5. The plant seed of claim 4, wherein the seed comprises at least two layers, the two layers comprising at least: (i) a first layer comprising the Bacillus velezensis (BV), and at least (ii) a second layer comprising the pectin or the pectin-related saccharide, wherein the second layer is interior relative to the first layer.

6. A method for increasing nodulation in a legume, the method comprising: (a) treating the legume, seeds of the legume, or soil surrounding the legume with *Bacillus velezensis* (BV) and (b) treating the legume, the seeds of the legume, or the soil surrounding the legume with a saccharide comprising pectin or a pectin-related saccharide, wherein the pectin-related saccharide is a heteropolysaccharide comprising D-galacturonate monomers which represent at least 50% of all monomers of the heteropolysaccharide.

7. The method of claim 6, wherein the legume, the seeds of the legume, or the soil surrounding the legume are treated concurrently with the (BV) and the saccharide.

8. The method of claim 6, wherein the legume, the seeds of the legume, or the soil surrounding the legume are treated first with the (BV) and subsequently the legume, the seeds of the legume, or the soil surrounding the legume are treated with the saccharide.

9. The method of claim 6, wherein the legume, the seeds of the legume, or the soil surrounding the legume are treated first with the saccharide and subsequently the legume, the seeds of the legume, or the soil surrounding the legume are treated with the (EV).

10. The method of claim 6, comprising administering a composition comprising the (EV) to the soil surrounding the legume at a rate that delivers $10^3$—$10^5$ CFU per gram soil.

11. A method for improving growth or health of a plant, the method comprising: (a) treating the plant, seeds of the plant, or soil surrounding the plant with *Bacillus velezensis* (BV) and (b) treating the plant, the seeds of the plant, or the soil surrounding the plant with a saccharide comprising pectin or a pectin-related saccharide, wherein the pectin-related saccharide is a heteropolysaccharide comprising D-galacturonate monomers which represent at least 50% of all monomers of the heteropolysaccharide.

* * * * *

SEQUENCE LISTING

```
<160> NUMBER OF SEQ ID NOS: 26

<210> SEQ ID NO 1
<211> LENGTH: 759
<212> TYPE: DNA
<213> ORGANISM: Bacillus Amyloliquefaciens

<400> SEQUENCE: 1
atgaaagagg tcataaaaat ccataaaaac gataacgtgc ttctcgccat gcgccatttt        60
aacaaggggg agcggctgca tacagacgga ctgacgattg aagtgaagga ccctgtaaag       120
cgggggcata aaatcgcgct gcaaaccatt gaagaaaacg gcagcatcat taaatacggt       180
ttttcaatcg ggcgtgcgac aaggcggatt tcggccggcg agcatattca tacccataat       240
ctgcaaacga atttatccga tgtgcaagaa tacacgtatt caccgcgctt cgaggacaat       300
ccttttacaa atgagaaccg gacatttaaa ggctacagaa gagaaaacgg tacatccggc       360
gttcggaatg aactgtggat cgtgcctaca gtcggctgcg taaacggcgt cgctgagaaa       420
atcctgcagc gtttcgtaaa agaggcgaaa gacattgcgc cctttgacaa tgtgctggtt       480
ttaaagcacc aatacggctg ctcccagctt ggcgatgatc atgaaaatac gaaacaaatg       540
ctgatgaacg ccatccgtca tccaaatgcg ggcggtgtgc tggttttagg gctcggctgt       600
gaaaataatg agctggcggc gattagggaa acgctttctg aagtgaacgg agatcgggtg       660
aaatttctcg aatcacaagc tgtcacagct gagactgaca gcagatcaac tcgaaatgcg       720
tctaagactt cttggcattt caaatataaa cacaattaa                              759

<210> SEQ ID NO 2
<211> LENGTH: 252
<212> TYPE: PRT
<213> ORGANISM: Bacillus Amyloliquefaciens

<400> SEQUENCE: 2

Met Lys Glu Val Ile Lys Ile His Lys Asn Asp Asn Val Leu Leu Ala
1               5                   10                  15

Met Arg His Phe Asn Lys Gly Glu Arg Leu His Thr Asp Gly Leu Thr
            20                  25                  30

Ile Glu Val Lys Asp Pro Val Lys Arg Gly His Lys Ile Ala Leu Gln
        35                  40                  45

Thr Ile Glu Glu Asn Gly Ser Ile Ile Lys Tyr Gly Phe Ser Ile Gly
    50                  55                  60

Arg Ala Thr Arg Arg Ile Ser Ala Gly Glu His Ile His Thr His Asn
65                  70                  75                  80
```

```
Leu Gln Thr Asn Leu Ser Asp Val Gln Glu Tyr Thr Tyr Ser Pro Arg
                85                  90                  95

Phe Glu Asp Asn Pro Phe Thr Asn Glu Asn Arg Thr Phe Lys Gly Tyr
            100                 105                 110

Arg Arg Glu Asn Gly Thr Ser Gly Val Arg Asn Glu Leu Trp Ile Val
        115                 120                 125

Pro Thr Val Gly Cys Val Asn Gly Val Ala Glu Lys Ile Leu Gln Arg
    130                 135                 140

Phe Val Lys Glu Ala Lys Asp Ile Ala Pro Phe Asp Asn Val Leu Val
145                 150                 155                 160

Leu Lys His Gln Tyr Gly Cys Ser Gln Leu Gly Asp Asp His Glu Asn
                165                 170                 175

Thr Lys Gln Met Leu Met Asn Ala Ile Arg His Pro Asn Ala Gly Gly
            180                 185                 190

Val Leu Val Leu Gly Leu Gly Cys Glu Asn Asn Glu Leu Ala Ala Ile
        195                 200                 205

Arg Glu Thr Leu Ser Glu Val Asn Gly Asp Arg Val Lys Phe Leu Glu
    210                 215                 220

Ser Gln Ala Val Thr Ala Glu Thr Asp Ser Arg Ser Thr Arg Asn Ala
225                 230                 235                 240

Ser Lys Thr Ser Trp His Phe Lys Tyr Lys His Asn
                245                 250

<210> SEQ ID NO 3
<211> LENGTH: 1446
<212> TYPE: DNA
<213> ORGANISM: Bacillus Amyloliquefaciens

<400> SEQUENCE: 3
ttgcggaagc tgaataaaaa gatgtgcggt gaatacaatc aatatcctga aaaagtcctt      60
cagttcggcg aaggcaactt tttgcgggcc ttcgcagact ggcagatcga tcaattgaat     120
caactgacgg attttaacgg aagcgttgtc gccgtacagc cgagaggctc tgagaaaatc     180
aaacgtttaa cgagcagga cggtttattt acgctttttt tgcaggggat aaaggacgga     240
aaaccggctg aagaacacat gatcgtcaaa tccatcagcc gcggcattga tcttttttct     300
gactatgatt cctttaaacg gctggcagca caagaggagc ttcgttttat catttccaat     360
acgacagaag cgggaatcac gtttgagaaa ggcgaccggc ttgaggatag acctcaaaaa     420
acattccccg ggaaattagc ggcgttcctt tatttccgct ataatgcatt tgcgggtgac     480
gccgagaaag ggtgcattgt gcttccatgt gaactggtcg aagaaacgg acggaaactg     540 aaggcggccg tgcttcaata tgccgggctg tgggagctgg aacctggttt tactcaatgg     600
attcatgacg cgaacatctt ctgcaatacc ctcgtggatc ggattgttcc cggatttcct     660
gttgataccg cggaagaact taccgatttt ctcggatacg aagaccgtct gctggtggtt     720
ggtgagcatt attatttgtg ggtgatagaa gggccggaac agcttcagaa tgagcttcct     780
tttgctgagg ccgggctgaa cgcactgatc acgtctgacc ttacgtctta caggacaaaa     840
aaggtgagaa tcttaaacgg cgctcacacg gcattggcgc cagtggcttt actatacgga     900
ctgcaaaccg tccgggaagc ggctgagcac gaggtgacgg gcagattcat tgaagagctg     960
atcaatgaag aaatcctccc tgtgctgcaa atggagggtg tcacccaata cgcggcagat    1020
gtgttacagc ggtttaaaaa cccttatatc caccattatc tgcaaagcat tacccttaac    1080
gccgccgcga aattcaaaac aagaaacctg ccgacgctga aggcttatat cgaacaggag    1140
```

```
ggccggctac ctgagaagct ggtatttcg ttcagcgcca tgatctattc atactggaac    1200
ggaccgaaca aaccggctga cggcgagggg gttcttaacc gttttcaaat ggcgcgtcc    1260 cgttgcaaag atgatatgtt tcaagcggca tctgccatat taggagaaga ccggttgtgg    1320
ggaaagaatc tgaaccatct tccggggctg actgaacgaa cggcttttt tctgtctgtc    1380 attcataagc ggggtatgaa gcatgcgtta catgaatgct gcggaaaaaa gggggaagtg    1440
aaatga                                                              1446
```

<210> SEQ ID NO 4
<211> LENGTH: 481
<212> TYPE: PRT
<213> ORGANISM: Bacillus Amyloliquefaciens

<400> SEQUENCE: 4

```
Met Arg Lys Leu Asn Lys Lys Met Cys Gly Glu Tyr Asn Gln Tyr Pro
1               5                   10                  15

Glu Lys Val Leu Gln Phe Gly Glu Gly Asn Phe Leu Arg Ala Phe Ala
            20                  25                  30

Asp Trp Gln Ile Asp Gln Leu Asn Gln Leu Thr Asp Phe Asn Gly Ser
        35                  40                  45

Val Val Ala Val Gln Pro Arg Gly Ser Glu Lys Ile Lys Arg Leu Asn
    50                  55                  60

Glu Gln Asp Gly Leu Phe Thr Leu Phe Leu Gln Ile Lys Asp Gly
65                  70                  75                  80

Lys Pro Ala Glu Glu His Met Ile Val Lys Ser Ile Ser Arg Gly Ile
                85                  90                  95

Asp Leu Phe Ser Asp Tyr Asp Ser Phe Lys Arg Leu Ala Ala Gln Glu
            100                 105                 110

Glu Leu Arg Phe Ile Ile Ser Asn Thr Thr Glu Ala Gly Ile Thr Phe
        115                 120                 125

Glu Lys Gly Asp Arg Leu Glu Asp Arg Pro Gln Lys Thr Phe Pro Gly
    130                 135                 140

Lys Leu Ala Ala Phe Leu Tyr Phe Arg Tyr Asn Ala Phe Ala Gly Asp
145                 150                 155                 160

Ala Glu Lys Gly Cys Ile Val Leu Pro Cys Glu Leu Val Glu Glu Asn
                165                 170                 175

Gly Arg Lys Leu Lys Ala Ala Val Leu Gln Tyr Ala Gly Leu Trp Glu
            180                 185                 190

Leu Glu Pro Gly Phe Thr Gln Trp Ile His Asp Ala Asn Ile Phe Cys
        195                 200                 205

Asn Thr Leu Val Asp Arg Ile Val Pro Gly Phe Pro Val Asp Thr Ala
    210                 215                 220

Glu Glu Leu Thr Asp Phe Leu Gly Tyr Glu Asp Arg Leu Leu Val Val
225                 230                 235                 240

Gly Glu His Tyr Tyr Leu Trp Val Ile Glu Gly Pro Glu Gln Leu Gln
                245                 250                 255

Asn Glu Leu Pro Phe Ala Glu Ala Gly Leu Asn Ala Leu Ile Thr Ser
            260                 265                 270

Asp Leu Thr Ser Tyr Arg Thr Lys Lys Val Arg Ile Leu Asn Gly Ala
        275                 280                 285

His Thr Ala Leu Ala Pro Val Ala Leu Leu Tyr Gly Leu Gln Thr Val
    290                 295                 300

Arg Glu Ala Ala Glu His Glu Val Thr Gly Arg Phe Ile Glu Glu Leu
```

| | | | | | 305 | | | | | 310 | | | | | 315 | | | | | 320 |

Ile Asn Glu Glu Ile Leu Pro Val Leu Gln Met Glu Gly Val Thr Gln
                    325                 330                 335

Tyr Ala Ala Asp Val Leu Gln Arg Phe Lys Asn Pro Tyr Ile His His
                340                 345                 350

Tyr Leu Gln Ser Ile Thr Leu Asn Ala Ala Lys Phe Lys Thr Arg
            355                 360                 365

Asn Leu Pro Thr Leu Lys Ala Tyr Ile Glu Gln Glu Gly Arg Leu Pro
        370                 375                 380

Glu Lys Leu Val Phe Ser Phe Ser Ala Met Ile Tyr Ser Tyr Trp Asn
385                 390                 395                 400

Gly Pro Asn Lys Pro Ala Asp Gly Glu Gly Val Leu Asn Arg Phe Gln
                405                 410                 415

Met Ala Arg Ser Arg Cys Lys Asp Asp Met Phe Gln Ala Ala Ser Ala
                420                 425                 430

Ile Leu Gly Glu Asp Arg Leu Trp Gly Lys Asn Leu Asn His Leu Pro
            435                 440                 445

Gly Leu Thr Glu Arg Thr Ala Phe Phe Leu Ser Val Ile His Lys Arg
        450                 455                 460

Gly Met Lys His Ala Leu His Glu Cys Cys Gly Lys Lys Gly Glu Val
465                 470                 475                 480

Lys

<210> SEQ ID NO 5
<211> LENGTH: 1206
<212> TYPE: DNA
<213> ORGANISM: Bacillus Amyloliquefaciens

<400> SEQUENCE: 5

```
atgagggcca acggcattga agagcgctgc attaccggaa acgcttcaga tgaagagaag    60
ttttcgcct gggcaaaaac ggtgccgatg gcgataggca atccgctgta cagctggacg   120
catttagagc tgcagcgctg gttcggcatt tatgacgtat tgaatgaaaa acggccgcg   180
gcaatttgga aaaaaacgaa tgagctcctg cagggagacg ggtttggcgc aagggatctc   240
attctgaaat caaaagtcaa agtcatttgc acaaccgacg atcctgccga tgcgctgaca   300
taccacgaac tgttgaaaga agtgattttt ccggttcaag tgctgcccgg atttcggcct   360
gacaaaggac tggacatcag cagcccgggt tttgccgatt gggtccgttc gctggagagc   420
gcttccggaa tagctgtcac cacctaccaa tcgtatttag atgcgttaga atcccgcgtc   480
cgcttttttc acaatgccgg gggaagagtg tcggatcatg cgttagatca aatggtttat   540
gccgagacga ccgaagagga gcggcccgg attttttgccg ccggattaag cggagagcat   600
gtgtcttttg aagatgaaaa gaaattcaaa acacggacgc tgcaatatct ttgcggtctt   660
tacgccgaac tggactgggc gatgcagttc catattaacg cgttaagaaa taccaataca   720
aataagttca gcagcctcgg tcctgatacg ggatatgact caattaatga tgaacgtatc   780
gcaaagccgc ttgcccggct gttagattcc gccgaaaaaa agcggcaatt gcctaaaacg   840
atttttgtatt ctttgaatcc gaatgacaac tatattatcg ccagcatgat caacagcttt   900
caggatggga aaacaccggg gaaaattcaa ttcggcacag cctggtggtt caatgacacg   960
aaagatggaa tgcttcagca aatgaaagcg ttatcaaaca tgggcctgtt cagccgtttt  1020
atcgggatgc tgacggattc aagaagtttc ctgtcctacc cccgccatga atacttcagg  1080
cggcttgtct gcacgctgat cggcggctgg gcggaacaag gcgaagcgcc ttacgatatg  1140
```

```
gagcttttag gaaggattgt cgagggaatt tgttaccgga atgctgagga atatttccgc    1200
ttttaa                                                               1206
```

<210> SEQ ID NO 6
<211> LENGTH: 401
<212> TYPE: PRT
<213> ORGANISM: Bacillus Amyloliquefaciens

<400> SEQUENCE: 6

```
Met Arg Ala Asn Gly Ile Glu Glu Arg Cys Ile Thr Gly Asn Ala Ser
1               5                   10                  15

Asp Glu Glu Lys Phe Phe Ala Trp Ala Lys Thr Val Pro Met Ala Ile
            20                  25                  30

Gly Asn Pro Leu Tyr Ser Trp Thr His Leu Glu Leu Gln Arg Trp Phe
        35                  40                  45

Gly Ile Tyr Asp Val Leu Asn Glu Lys Thr Ala Ala Ile Trp Lys
    50                  55                  60

Lys Thr Asn Glu Leu Leu Gln Gly Asp Gly Phe Gly Ala Arg Asp Leu
65              70                  75                  80

Ile Leu Lys Ser Lys Val Lys Val Ile Cys Thr Thr Asp Asp Pro Ala
                85                  90                  95

Asp Ala Leu Thr Tyr His Glu Leu Leu Lys Glu Ser Asp Phe Pro Val
            100                 105                 110

Gln Val Leu Pro Gly Phe Arg Pro Asp Lys Gly Leu Asp Ile Ser Ser
        115                 120                 125

Pro Gly Phe Ala Asp Trp Val Arg Ser Leu Glu Ser Ala Ser Gly Ile
130                 135                 140

Ala Val Thr Thr Tyr Gln Ser Tyr Leu Asp Ala Leu Glu Ser Arg Val
145                 150                 155                 160

Arg Phe Phe His Asn Ala Gly Gly Arg Val Ser Asp His Ala Leu Asp
                165                 170                 175

Gln Met Val Tyr Ala Glu Thr Thr Glu Glu Ala Ala Arg Ile Phe
            180                 185                 190

Ala Ala Gly Leu Ser Gly Glu His Val Ser Phe Glu Asp Glu Lys Lys
        195                 200                 205

Phe Lys Thr Arg Thr Leu Gln Tyr Leu Cys Gly Leu Tyr Ala Glu Leu
    210                 215                 220

Asp Trp Ala Met Gln Phe His Ile Asn Ala Leu Arg Asn Thr Asn Thr
225                 230                 235                 240

Asn Lys Phe Ser Ser Leu Gly Pro Asp Thr Gly Tyr Asp Ser Ile Asn
                245                 250                 255

Asp Glu Arg Ile Ala Lys Pro Leu Ala Arg Leu Leu Asp Ser Ala Glu
            260                 265                 270

Lys Lys Arg Gln Leu Pro Lys Thr Ile Leu Tyr Ser Leu Asn Pro Asn
        275                 280                 285

Asp Asn Tyr Ile Ile Ala Ser Met Ile Asn Ser Phe Gln Asp Gly Lys
    290                 295                 300

Thr Pro Gly Lys Ile Gln Phe Gly Thr Ala Trp Trp Phe Asn Asp Thr
305                 310                 315                 320

Lys Asp Gly Met Leu Gln Gln Met Lys Ala Leu Ser Asn Met Gly Leu
                325                 330                 335

Phe Ser Arg Phe Ile Gly Met Leu Thr Asp Ser Arg Ser Phe Leu Ser
            340                 345                 350
```

```
Tyr Pro Arg His Glu Tyr Phe Arg Arg Leu Val Cys Thr Leu Ile Gly
            355                 360                 365

Gly Trp Ala Glu Gln Gly Glu Ala Pro Tyr Asp Met Glu Leu Leu Gly
        370                 375                 380

Arg Ile Val Glu Gly Ile Cys Tyr Arg Asn Ala Glu Glu Tyr Phe Arg
385                 390                 395                 400

Phe

<210> SEQ ID NO 7
<211> LENGTH: 1077
<212> TYPE: DNA
<213> ORGANISM: Bacillus Amyloliquefaciens

<400> SEQUENCE: 7
atgaatatca cgtttcgctg gtacggccaa ggtaatgata cggtgactct tgaacatgtc      60
agacaaattc ccggggtcaa aggcatcgtc tgggctcttc accagaagca cgcgggcgaa     120
gtatgggaaa aggaggacat tgaagcggaa gtcagataca ttcaatccta tgggtttcat     180
gcagaggtcg tggaaagcgt gaatgttcat gaagccatta aactcggtca tgaagaacgc     240
ggacaatata ttgagcacta taaacagacc attcgcaatc tgtccgaatt cggcgtgaaa     300
gtcatctgct acaatttcat gccgatattt gactggacgc gtaccgatat gttccgcgcg     360
ctggaggatg ggtcaaccgc actgttttt gaaaaagcga agtgaaaag tctccctccg       420 gaggaactga tccgcacggt tgaagaatct tctgatttga cgcttcccgg gtgggagccg     480
gagaaaatgg ccaggatcaa ggaactgttt gaggcctatc aaacggttga tgaaaaacag     540
ctttgggcca atcttgagtt cttttttacat gaaatccttc ctgtagcgga ggaacacggc     600
attcaaatgg ccattcatcc ggatgatccg ccctggtcaa ttttttggcct gccccgtatt     660 atcaccggtg agaaaagtta tgaaaagctg caagagattt cagattcacc cgccaactgt     720
attacgttgt gcacggggtt cgatgggagcg atcccgcca atgatatggt gaagatcacc     780
aaacactatg cgggagctgc gccgtttgcc catatacgaa atgtgaaaat ctgcgataac     840
ggtgatttta cggaaacttc gcatcttacc agtgatgggt ccattgatat taccggtgtt     900
gtaaaagaat tgcacggcca agactataaa ggatatgtac ggcctgatca cggccgtcat     960
atctggggcg aacaatgccg gccgggttat ggtttatatg atcgtgcatt aggaattatg    1020
tatttgaacg gactgtggga tgcgttttcg tctcatgaga aagggggtgaa gagatga      1077

<210> SEQ ID NO 8
<211> LENGTH: 358
<212> TYPE: PRT
<213> ORGANISM: Bacillus Amyloliquefaciens

<400> SEQUENCE: 8

Met Asn Ile Thr Phe Arg Trp Tyr Gly Gln Gly Asn Asp Thr Val Thr
1               5                   10                  15

Leu Glu His Val Arg Gln Ile Pro Gly Val Lys Gly Ile Val Trp Ala
            20                  25                  30

Leu His Gln Lys His Ala Gly Glu Val Trp Glu Lys Glu Asp Ile Glu
        35                  40                  45

Ala Glu Val Arg Tyr Ile Gln Ser Tyr Gly Phe His Ala Glu Val Val
    50                  55                  60

Glu Ser Val Asn Val His Glu Ala Ile Lys Leu Gly His Glu Glu Arg
65                  70                  75                  80

Gly Gln Tyr Ile Glu His Tyr Lys Gln Thr Ile Arg Asn Leu Ser Glu
```

```
                    85                  90                  95
Phe Gly Val Lys Val Ile Cys Tyr Asn Phe Met Pro Ile Phe Asp Trp
            100                 105                 110

Thr Arg Thr Asp Met Phe Arg Ala Leu Glu Asp Gly Ser Thr Ala Leu
        115                 120                 125

Phe Phe Glu Lys Ala Lys Val Glu Ser Leu Pro Pro Glu Glu Leu Ile
    130                 135                 140

Arg Thr Val Glu Glu Ser Ser Asp Leu Thr Leu Pro Gly Trp Glu Pro
145                 150                 155                 160

Glu Lys Met Ala Arg Ile Lys Glu Leu Phe Glu Ala Tyr Gln Thr Val
                165                 170                 175

Asp Glu Lys Gln Leu Trp Ala Asn Leu Glu Phe Phe Leu His Glu Ile
            180                 185                 190

Leu Pro Val Ala Glu Glu His Gly Ile Gln Met Ala Ile His Pro Asp
        195                 200                 205

Asp Pro Pro Trp Ser Ile Phe Gly Leu Pro Arg Ile Ile Thr Gly Glu
    210                 215                 220

Lys Ser Tyr Glu Lys Leu Gln Glu Ile Ser Asp Ser Pro Ala Asn Cys
225                 230                 235                 240

Ile Thr Leu Cys Thr Gly Ser Met Gly Ala Asp Pro Ala Asn Asp Met
                245                 250                 255

Val Lys Ile Thr Lys His Tyr Ala Gly Ala Ala Pro Phe Ala His Ile
            260                 265                 270

Arg Asn Val Lys Ile Cys Asp Asn Gly Asp Phe Thr Glu Thr Ser His
        275                 280                 285

Leu Thr Ser Asp Gly Ser Ile Asp Ile Thr Gly Val Val Lys Glu Leu
    290                 295                 300

His Gly Gln Asp Tyr Lys Gly Tyr Val Arg Pro Asp His Gly Arg His
305                 310                 315                 320

Ile Trp Gly Glu Gln Cys Arg Pro Gly Tyr Gly Leu Tyr Asp Arg Ala
                325                 330                 335

Leu Gly Ile Met Tyr Leu Asn Gly Leu Trp Asp Ala Phe Ser Ser His
            340                 345                 350

Glu Lys Gly Val Lys Arg
        355

<210> SEQ ID NO 9
<211> LENGTH: 477
<212> TYPE: DNA
<213> ORGANISM: Bacillus Amyloliquefaciens

<400> SEQUENCE: 9
atggacgaaa cggggttttc cagcgtattt tcaaccaact ttaccggtgc atttctggca    60
tcgcaagtgt ttggaaaaga cctttttgaag gcggaatgtc ccgcgattat taatatttct   120
tctatgagtg cgtatacacc gatgacaaag gtgcccgcct acagcgcggc caaggcggcg   180
gttcagaatt ttacgatgtg gatggctgtt catttcgcaa aaaaagggct gcgggtgaat   240
gccatcgctc cgggtttctt tttgacagcg caaaaccgtg agttgttatt acaggaagat   300
ggaagtctga cagaccgatc caataagatt atggcacata caccgatgaa cgtttcgggg   360
aaaccggaag accttctggg aacgctcctg tggctttcgg atgattcatg ctcaggcttc   420
gtcaccgggg tcaccgttcc cgtcgacgga ggttttatgg cttattccgg agtgtga      477

<210> SEQ ID NO 10
```

<211> LENGTH: 158
<212> TYPE: PRT
<213> ORGANISM: Bacillus Amyloliquefaciens

<400> SEQUENCE: 10

```
Met Asp Glu Thr Gly Phe Ser Ser Val Phe Ser Thr Asn Phe Thr Gly
1               5                   10                  15

Ala Phe Leu Ala Ser Gln Val Phe Gly Lys Asp Leu Leu Lys Ala Glu
                20                  25                  30

Cys Pro Ala Ile Ile Asn Ile Ser Ser Met Ser Ala Tyr Thr Pro Met
            35                  40                  45

Thr Lys Val Pro Ala Tyr Ser Ala Lys Ala Ala Val Gln Asn Phe
        50                  55                  60

Thr Met Trp Met Ala Val His Phe Ala Lys Lys Gly Leu Arg Val Asn
65                  70                  75                  80

Ala Ile Ala Pro Gly Phe Phe Leu Thr Ala Gln Asn Arg Glu Leu Leu
                85                  90                  95

Leu Gln Glu Asp Gly Ser Leu Thr Asp Arg Ser Asn Lys Ile Met Ala
                100                 105                 110

His Thr Pro Met Lys Arg Phe Gly Lys Pro Glu Asp Leu Leu Gly Thr
            115                 120                 125

Leu Leu Trp Leu Ser Asp Asp Ser Cys Ser Gly Phe Val Thr Gly Val
130                 135                 140

Thr Val Pro Val Asp Gly Gly Phe Met Ala Tyr Ser Gly Val
145                 150                 155
```

<210> SEQ ID NO 11
<211> LENGTH: 636
<212> TYPE: DNA
<213> ORGANISM: Bacillus Amyloliquefaciens

<400> SEQUENCE: 11

```
atgctgccta agtacgccat ttacgaaaaa cttctgcatg cacaagtggt ggctgtcata    60
aggggacaaa acagccaaga ggcgcttgaa gtttcaaaag cggccatttc aggaggtatc   120
agcgccattg agcttacata cacaactcct gaagtggaag atgtctttaa ggaactccgg   180
catcaagata ttcttcttgg agccggctct gtaatggata cagaaacggc gagacacgcc   240
attttatcag gcgcctcatt tatcgtcagc tctcattttg taaagagat agcatctcta   300 tgcaaccagt acagcgtacc gtatcttccg ggatgcatga gtgtgtctga tatggctttg   360
gcgctcgaag ccggatgtga tgtggtaaag ctgttccccg ctaattcgtt tgacccttca   420
tttatcaagt cggtcaacgg ccctctgccg aatgtccgca ttatgccgac cggggggtatc   480 tcattaaaca gcatgaatga ctggctctct gccggagcgg tcgcggtcgg tgtgggaagc   540
gacttgacaa aagcatatca aaagggcggc tatgaggctg ccgtatccct cagcaaagaa   600
tacgtctgcc gaaaaacga atatacgggg gtgtaa                             636
```

<210> SEQ ID NO 12
<211> LENGTH: 211
<212> TYPE: PRT
<213> ORGANISM: Bacillus Amyloliquefaciens

<400> SEQUENCE: 12

```
Met Leu Pro Lys Tyr Ala Ile Tyr Glu Lys Leu Leu His Ala Gln Val
1               5                   10                  15

Val Ala Val Ile Arg Gly Gln Asn Ser Gln Glu Ala Leu Glu Val Ser
                20                  25                  30
```

Lys Ala Ala Ile Ser Gly Gly Ile Ser Ala Ile Glu Leu Thr Tyr Thr
            35                  40                  45

Thr Pro Glu Val Glu Asp Val Phe Lys Glu Leu Arg His Gln Asp Ile
 50                  55                  60

Leu Leu Gly Ala Gly Ser Val Met Asp Thr Glu Thr Ala Arg His Ala
 65                  70                  75                  80

Ile Leu Ser Gly Ala Ser Phe Ile Val Ser Ser His Phe Val Lys Glu
                 85                  90                  95

Ile Ala Ser Leu Cys Asn Gln Tyr Ser Val Pro Tyr Leu Pro Gly Cys
                100                 105                 110

Met Ser Val Ser Asp Met Ala Leu Ala Leu Glu Ala Gly Cys Asp Val
                115                 120                 125

Val Lys Leu Phe Pro Ala Asn Ser Phe Asp Pro Ser Phe Ile Lys Ser
130                 135                 140

Val Asn Gly Pro Leu Pro Asn Val Arg Ile Met Pro Thr Gly Gly Ile
145                 150                 155                 160

Ser Leu Asn Ser Met Asn Asp Trp Leu Ser Ala Gly Ala Val Ala Val
                165                 170                 175

Gly Val Gly Ser Asp Leu Thr Lys Ala Tyr Gln Lys Gly Tyr Glu
                180                 185                 190

Ala Ala Val Ser Leu Ser Lys Glu Tyr Val Cys Arg Lys Asn Glu Tyr
                195                 200                 205

Thr Gly Val
    210

<210> SEQ ID NO 13
<211> LENGTH: 957
<212> TYPE: DNA
<213> ORGANISM: Bacillus Amyloliquefaciens

<400> SEQUENCE: 13
gtggcttctg attatggcat ttttacgatc ggtgatgcga tgatcacctt aaatcccgca      60
agcacaggac ctttgcgttt tgttacccat tttgaacgaa aagcaggagg agctgaactg     120
aattttgcga ttgcatgcgc cagattgaat ctgcactcaa agtgggtcag cagactgggg     180
aaggatgagt tcggcagagt gatttatcag tttgccagag gagaaggaat tgatgtgact     240
gacgtctcct atgttgaagg cttccctaca tctttaaatg tcaaagagat cagaaatgac     300
ggttcaggca agacgtttta ttatcgtttc aattcaccaa ttctgactct gcaccggaa      360 gatataacag agaatatgtt tgacggcatt cacatcgttc atcttaccgg tgtgttcctc     420
gcgcttgata agaaaaatct tgaaattgct gaaaggtgc tttccatcgc caaagcaagg      480
gggattcccg tatcttttga tccgaatatc aggctgaagc tgtggacgat tgaggaggcg     540
cgtgcggcat tcatcaaat ctttccgcat actgatattc ttctggcggg ccgggacgaa      600
atgaaacagc tgacaggtat aggggaaaat gaagcattag cccggtttgc agagacctat     660
tcaatcagtc agcttgtcat aaaagacggt gaagcaggtt ctgcgctgta tcatgatcat     720
aagtggattc acaaagaggc tttcccggtt gcgcctgttg acacggtagg agcgggtgac     780
ggctttaatg ccggctacct gtacagttat ctgcatggtt ttgaaccgga aaaacgtctg     840
gagtttgcca atgcggtcgg tgcgctcgtc accacagttt ccggtgacaa tgaagggctt     900
ccctatctag aagaggttct gtcatttgta aacaaagaga ctgtgattga acggtag        957

<210> SEQ ID NO 14

<211> LENGTH: 318
<212> TYPE: PRT
<213> ORGANISM: Bacillus Amyloliquefaciens

<400> SEQUENCE: 14

```
Met Ala Ser Asp Tyr Gly Ile Phe Thr Ile Gly Asp Ala Met Ile Thr
1               5                   10                  15
Leu Asn Pro Ala Ser Thr Gly Pro Leu Arg Phe Val Thr His Phe Glu
            20                  25                  30
Arg Lys Ala Gly Gly Ala Glu Leu Asn Phe Ala Ile Ala Cys Ala Arg
        35                  40                  45
Leu Asn Leu His Ser Lys Trp Val Ser Arg Leu Gly Lys Asp Glu Phe
    50                  55                  60
Gly Arg Val Ile Tyr Gln Phe Ala Arg Gly Glu Gly Ile Asp Val Thr
65                  70                  75                  80
Asp Val Ser Tyr Val Glu Gly Phe Pro Thr Ser Leu Asn Val Lys Glu
                85                  90                  95
Ile Arg Asn Asp Gly Ser Gly Lys Thr Phe Tyr Tyr Arg Phe Asn Ser
            100                 105                 110
Pro Ile Leu Thr Leu Ala Pro Glu Asp Ile Thr Glu Asn Met Phe Asp
        115                 120                 125
Gly Ile His Ile Val His Leu Thr Gly Val Phe Leu Ala Leu Asp Lys
    130                 135                 140
Lys Asn Leu Glu Ile Ala Glu Arg Val Leu Ser Ile Ala Lys Ala Arg
145                 150                 155                 160
Gly Ile Pro Val Ser Phe Asp Pro Asn Ile Arg Leu Lys Leu Trp Thr
                165                 170                 175
Ile Glu Glu Ala Arg Ala Ala Phe His Gln Ile Phe Pro His Thr Asp
            180                 185                 190
Ile Leu Leu Ala Gly Arg Asp Glu Met Lys Gln Leu Thr Gly Ile Gly
        195                 200                 205
Glu Asn Glu Ala Leu Ala Arg Phe Ala Glu Thr Tyr Ser Ile Ser Gln
    210                 215                 220
Leu Val Ile Lys Asp Gly Glu Ala Gly Ser Ala Leu Tyr His Asp His
225                 230                 235                 240
Lys Trp Ile His Lys Glu Ala Phe Pro Val Ala Pro Val Asp Thr Val
                245                 250                 255
Gly Ala Gly Asp Gly Phe Asn Ala Gly Tyr Leu Tyr Ser Tyr Leu His
            260                 265                 270
Gly Phe Glu Pro Glu Lys Arg Leu Glu Phe Ala Asn Ala Val Gly Ala
        275                 280                 285
Leu Val Thr Thr Val Ser Gly Asp Asn Glu Gly Leu Pro Tyr Leu Glu
    290                 295                 300
Glu Val Leu Ser Phe Val Asn Lys Glu Thr Val Ile Glu Arg
305                 310                 315
```

<210> SEQ ID NO 15
<211> LENGTH: 1002
<212> TYPE: DNA
<213> ORGANISM: Bacillus Amyloliquefaciens

<400> SEQUENCE: 15

```
atgaaaacca ttacaatttc tgatgtggcg aaatatgcaa acgtatctaa aagcaccgta      60
tctcaatttt taaatcagcg ctatgactat atgagcgaga aaacgaaaca aaaaatagaa     120
gcggccattc aagagctgaa ctatcagccg aatttcgtcg cccgcagctt aaaacagaaa     180
```

```
tcaacattta cggtaggtgt ggtggtggct aatattcttc acacttttc cactcaggtc    240
atcagggcgg tggaagacta ttttcatgaa caaggatttc atattattgt ctgcaatgcg    300
gatgatgaaa cggagaaaga aaagaaatat attgaaatgc tgcgggctaa gcaggtggac    360
ggaattatta ttttccgac gggcgaaaat ctctctttat atgaaaagat gaaacgcgat    420
acgtttccgg ttgtgtttat ggacagaacc attgaagaac tcggaattcc gacagtgatg    480
cttgataatc atcatgcagc cggtcttgcc gttaccggt ttatcgaaag cggcattaag    540
agaatcgcaa ttattacgac gtctattatt cgggaaatca gtccgagggt agaaaggatt    600
gaagggtata aaaaggcgct tgaccgtcac ggaatgatgg tgcgggacga atatatcaaa    660
acagccgatg cggctgatat ttccaatgtt ttgtcagagc tgttctcact tgaggagcct    720
ccgaaagcga tattggcggc aaacgatatc gttcttgttg aggtgctgaa gtatatgaag    780
gagcatgata tgacaattcc ggataaggca gccgtcatcg gaattgatga agttcctttt    840
gcgggttttt ttactcctcc gattacgacg atcgtccagc ctgcggcaga aatggcgcga    900
aaagcgggaa gccttcttct tcgccagata caagaaaaag atggcggtga aaaacggatt    960
caccgctata aaccggcgct gctcgcaagg caatccggat aa                      1002
```

<210> SEQ ID NO 16
<211> LENGTH: 333
<212> TYPE: PRT
<213> ORGANISM: Bacillus Amyloliquefaciens

<400> SEQUENCE: 16

```
Met Lys Thr Ile Thr Ile Ser Asp Val Ala Lys Tyr Ala Asn Val Ser
1               5                   10                  15

Lys Ser Thr Val Ser Gln Phe Leu Asn Gln Arg Tyr Asp Tyr Met Ser
            20                  25                  30

Glu Lys Thr Lys Gln Lys Ile Glu Ala Ala Ile Gln Glu Leu Asn Tyr
        35                  40                  45

Gln Pro Asn Phe Val Ala Arg Ser Leu Lys Gln Lys Ser Thr Phe Thr
    50                  55                  60

Val Gly Val Val Val Ala Asn Ile Leu His Thr Phe Ser Thr Gln Val
65                  70                  75                  80

Ile Arg Ala Val Glu Asp Tyr Phe His Glu Gln Gly Phe His Ile Ile
                85                  90                  95

Val Cys Asn Ala Asp Asp Glu Thr Glu Lys Glu Lys Tyr Ile Glu
            100                 105                 110

Met Leu Arg Ala Lys Gln Val Asp Gly Ile Ile Ile Phe Pro Thr Gly
        115                 120                 125

Glu Asn Leu Ser Leu Tyr Glu Lys Met Lys Arg Asp Thr Phe Pro Val
    130                 135                 140

Val Phe Met Asp Arg Thr Ile Glu Glu Leu Gly Ile Pro Thr Val Met
145                 150                 155                 160

Leu Asp Asn His His Ala Ala Gly Leu Ala Val Asp Arg Phe Ile Glu
                165                 170                 175

Ser Gly Ile Lys Arg Ile Ala Ile Ile Thr Thr Ser Ile Ile Arg Glu
            180                 185                 190

Ile Ser Pro Arg Val Glu Arg Ile Glu Gly Tyr Lys Lys Ala Leu Asp
        195                 200                 205

Arg His Gly Met Met Val Arg Asp Glu Tyr Ile Lys Thr Ala Asp Ala
    210                 215                 220
```

```
Ala Asp Ile Ser Asn Val Leu Ser Glu Leu Phe Ser Leu Glu Glu Pro
225                 230                 235                 240

Pro Lys Ala Ile Leu Ala Ala Asn Asp Ile Val Leu Val Glu Val Leu
                245                 250                 255

Lys Tyr Met Lys Glu His Asp Met Thr Ile Pro Asp Lys Ala Ala Val
                260                 265                 270

Ile Gly Ile Asp Glu Val Pro Phe Ala Gly Phe Phe Thr Pro Pro Ile
            275                 280                 285

Thr Thr Ile Val Gln Pro Ala Ala Glu Met Ala Arg Lys Ala Gly Ser
            290                 295                 300

Leu Leu Leu Arg Gln Ile Gln Glu Lys Asp Gly Gly Glu Lys Arg Ile
305                 310                 315                 320

His Arg Tyr Lys Pro Ala Leu Leu Ala Arg Gln Ser Gly
                325                 330

<210> SEQ ID NO 17
<211> LENGTH: 489
<212> TYPE: DNA
<213> ORGANISM: Bacillus Amyloliquefaciens

<400> SEQUENCE: 17
atgttctcaa aagatagatt ccctattatt cttctttat tttcagccgg ggtgattaac      60
tatttagacc gctcagcgct gtctattgca gcgccgttca tacagcagga tctcacattg     120
tctgcaaccc aaatggggct gattttcagc agttttctg tcggatacgc tgtgtttaac     180
tttctcggcg gtgttgcatc tgaccggtat ggggctaaat tgacattgtg tacggcgatg    240
atcgtttggt ctcttttcag cggagcggtt gcgcttgctt tcggatttgt aagtcttttg    300
attatccgtg ttttattcgg tatgggagag gggccgctgt cggctgccat aagcaaaatg    360
gtcaacaatt ggtttcctcc gtctcagcgc gccacggtca tcggcctgac aaacagcggc    420
acgccgctcg gccggttttg gattgatgct tggttaattg gatggcggag cttggcagtg    480
ccgcgatga                                                             489

<210> SEQ ID NO 18
<211> LENGTH: 162
<212> TYPE: PRT
<213> ORGANISM: Bacillus Amyloliquefaciens

<400> SEQUENCE: 18

Met Phe Ser Lys Asp Arg Phe Pro Ile Ile Leu Leu Leu Phe Ser Ala
1               5                   10                  15

Gly Val Ile Asn Tyr Leu Asp Arg Ser Ala Leu Ser Ile Ala Ala Pro
                20                  25                  30

Phe Ile Gln Gln Asp Leu Thr Leu Ser Ala Thr Gln Met Gly Leu Ile
            35                  40                  45

Phe Ser Ser Phe Ser Val Gly Tyr Ala Val Phe Asn Phe Leu Gly Gly
        50                  55                  60

Val Ala Ser Asp Arg Tyr Gly Ala Lys Leu Thr Leu Cys Thr Ala Met
65                  70                  75                  80

Ile Val Trp Ser Leu Phe Ser Gly Ala Val Ala Leu Ala Phe Gly Phe
                85                  90                  95

Val Ser Leu Leu Ile Ile Arg Val Leu Phe Gly Met Gly Glu Gly Pro
                100                 105                 110

Leu Ser Ala Ala Ile Ser Lys Met Val Asn Asn Trp Phe Pro Pro Ser
            115                 120                 125
```

-continued

```
Gln Arg Ala Thr Val Ile Gly Leu Thr Asn Ser Gly Thr Pro Leu Gly
        130                 135                 140
Arg Phe Trp Ile Asp Ala Trp Leu Ile Gly Trp Arg Ser Leu Ala Val
145                 150                 155                 160
Pro Arg

<210> SEQ ID NO 19
<211> LENGTH: 1266
<212> TYPE: DNA
<213> ORGANISM: Bacillus Amyloliquefaciens

<400> SEQUENCE: 19
atgaaaaaaa tgttatttat gctggcggtt tgtttatgta tgatccctgc ggacgtctat      60
gccgctgatc tgggacggca gacgttagga acaaatgacg gctggggagc cgcttccggc     120
gggacaaccg gcggcgcgaa agcctcttca tcgaatgtat acaccgtatc aaacagacag     180
cagctcgttt ctgcattagg gggaagcgcc aacagcacac gaagattat ttacatacaa      240 ggcacaatca atatgaatac ggacgaccgc aataaaacgc tcggctttga tgattataaa     300
gatccggcat atgatccgaa cgcctatttg aaggcgtacg acccggacaa tggggtaaa      360 aaagcgccgt caggcaccca ggaagacgcc agacagcgat cgcaaaaaaa ccagaaggca     420
cgggtcgtgg ttgacattcc ttcaaatacg acgatcatcg gctcgggttc aaatgccaaa     480
gtgacaggcg ggaattttaa tattaagaac ggcgtcgaca atgtcatcat ccgcaacatt     540
gaatttcaag acgcttacga ctattttccg caatgggacc cgacggacgg cagcagcggc     600
aactggaact cggaatatga caatatcacc attaacggcg cgacgcacat ctggatcgat     660
cattgcacct ttaatgacgg atcgaatccc gacagcagtt ttccctacta ttacgggaga     720
aaatatcagc accatgacgg ccagacggat atagccaacg gggcgaatta tattacattg     780
tcctataata aatatcatga ccatgacaaa ggctccgtca tcggaaacag cgacagcaag     840
acgtcggatg aaggaaaact gaaggtgacc attcaccata actattacca gaacatcgtc     900
cagcgcgcac cgcgggtccg gtacgggcag gttcatattt ataataattt ttacgcaggc     960
tctaaaagcg ccgcatatccc gttcagctat gcgtggggcg cgggacacgc gtcaaaaata    1020
tatgctcaga taatgtcttt gaagtgccgg ggtctggctg ctgataaggt catcagcgtc    1080
ttcagcggcg gaaaagcgct tcatgaagac ggcactcttt taaacggcgc cgccattaac    1140
gcgtcagccg ccaacggatt aagtcagtcc gtcggctgga caccgtcatt gcacggttct    1200
atcggctcat catcaaatgt aaaatcagat gttatatcta agccggagc gggcatatta    1260 aaataa                                                              1266

<210> SEQ ID NO 20
<211> LENGTH: 421
<212> TYPE: PRT
<213> ORGANISM: Bacillus Amyloliquefaciens

<400> SEQUENCE: 20

Met Lys Lys Met Leu Phe Met Leu Ala Val Cys Leu Cys Met Ile Pro
1               5                   10                  15
Ala Asp Val Tyr Ala Ala Asp Leu Gly Arg Gln Thr Leu Gly Thr Asn
                20                  25                  30
Asp Gly Trp Gly Ala Ala Ser Gly Thr Thr Gly Gly Ala Lys Ala
            35                  40                  45
Ser Ser Ser Asn Val Tyr Thr Val Ser Asn Arg Gln Gln Leu Val Ser
        50                  55                  60
```

Ala Leu Gly Gly Ser Ala Asn Ser Thr Pro Lys Ile Ile Tyr Ile Gln
 65                  70                  75                  80

Gly Thr Ile Asn Met Asn Thr Asp Asp Arg Asn Lys Thr Leu Gly Phe
                 85                  90                  95

Asp Asp Tyr Lys Asp Pro Ala Tyr Asp Pro Asn Ala Tyr Leu Lys Ala
            100                 105                 110

Tyr Asp Pro Asp Lys Trp Gly Lys Lys Ala Pro Ser Gly Thr Gln Glu
        115                 120                 125

Asp Ala Arg Gln Arg Ser Gln Lys Asn Gln Lys Ala Arg Val Val Val
130                 135                 140

Asp Ile Pro Ser Asn Thr Thr Ile Ile Gly Ser Gly Ser Asn Ala Lys
145                 150                 155                 160

Val Thr Gly Gly Asn Phe Asn Ile Lys Asn Gly Val Asp Asn Val Ile
                165                 170                 175

Ile Arg Asn Ile Glu Phe Gln Asp Ala Tyr Asp Tyr Phe Pro Gln Trp
            180                 185                 190

Asp Pro Thr Asp Gly Ser Ser Gly Asn Trp Asn Ser Glu Tyr Asp Asn
        195                 200                 205

Ile Thr Ile Asn Gly Ala Thr His Ile Trp Ile Asp His Cys Thr Phe
210                 215                 220

Asn Asp Gly Ser Asn Pro Asp Ser Ser Phe Pro Tyr Tyr Gly Arg
225                 230                 235                 240

Lys Tyr Gln His His Asp Gly Gln Thr Asp Ile Ala Asn Gly Ala Asn
                245                 250                 255

Tyr Ile Thr Leu Ser Tyr Asn Lys Tyr His Asp His Lys Gly Ser
            260                 265                 270

Val Ile Gly Asn Ser Asp Ser Lys Thr Ser Asp Glu Gly Lys Leu Lys
        275                 280                 285

Val Thr Ile His His Asn Tyr Tyr Gln Asn Ile Val Gln Arg Ala Pro
        290                 295                 300

Arg Val Arg Tyr Gly Gln Val His Ile Tyr Asn Asn Phe Tyr Ala Gly
305                 310                 315                 320

Ser Lys Ser Ala Ala Tyr Pro Phe Ser Tyr Ala Trp Gly Ala Gly His
                325                 330                 335

Ala Ser Lys Ile Tyr Ala Gln Asn Asn Val Phe Glu Val Pro Gly Leu
            340                 345                 350

Ala Ala Asp Lys Val Ile Ser Val Phe Ser Gly Gly Lys Ala Leu His
        355                 360                 365

Glu Asp Gly Thr Leu Leu Asn Gly Ala Ala Ile Asn Ala Ser Ala Ala
        370                 375                 380

Asn Gly Leu Ser Gln Ser Val Gly Trp Thr Pro Ser Leu His Gly Ser
385                 390                 395                 400

Ile Gly Ser Ser Ser Asn Val Lys Ser Asp Val Ile Ser Lys Ala Gly
                405                 410                 415

Ala Gly Ile Leu Lys
            420

<210> SEQ ID NO 21
<211> LENGTH: 1407
<212> TYPE: DNA
<213> ORGANISM: Bacillus Amyloliquefaciens

<400> SEQUENCE: 21
atgaaaataa aattatcgat tttatccgct gcggttctgg ccgcaggcat taccgccttt     60

```
gtctggccaa aaacagaggc caatgaaaaa acgcagacgg acgccgtgta tgtttctccc      120
gcaggcagcg accaaaatga aggaacgtta gaaaagccgt tccgcacatt aaaacatgcg      180
gctgaaaagg cagaggccgg aacaaccgta ttgattcggg aagggacgta cgatgaaacg      240
tttgaagtaa agcacagcgg cacggccgaa aagccgatta catttcggaa ctatcagaat      300
gagcatgtct caatcagcgg caaatctgcg ccaaaaagcg attctgaaac tccgttaatt      360
caaatccgca ataaacagta cattaccatt acggcgtta cgcttgagaa cctctccgta      420
tcatcagaag atgcgactgc catggggatc tgcgtcaccg gatcaagcag tcatatcaat      480
attgagggca accatatccg aaacattaaa accacggctg atgagggaaa tgcacacggc      540
atcgcgtttt acggcacagg cgccatgaag gatgtcagca tcacaaataa tacggttgaa      600
aaactgacgc tcggcgcaag cgaagcggtc gtgctgaacg ggaatgttga cggatttaag      660
attgccggca ataccattcg ggacaataac aatatcggga ttgacgtgat cggatacgaa      720
ggaacgtcca agcaaaacga ctatgcgcga acggcgtca ttgaaaacaa tacggtgagc       780
cataactctt cttacggaaa tcccgcttac ggagatgaat attcagcggg cggtatttac      840
gttgacggcg cagaacatgt ggacattaag aagaacaccg tttacaacaa tgacctcggc      900
attgaagcca cttccgaaca tagagggaaa tacgcacgag atatccggat tacggataac      960
aaggtgtacg gcaatgctta caccggtatt tcaatcggag ctatgacac gaaacgcggc      1020
ggcaccatca attcggtgat cgctcataac attatgtatc gaaatgacac gaaggacctt     1080
gacggcggcc agctgctgct gcagtacggc acaaaaggga cacgatcga aaaaaacatc     1140
atgacggcaa gcggttcacg gattttatc gcaaatgatt atacgaaaaa cgaaggcaat     1200
actgttaatc ataacgtcta tcacaaagaa gccggaaaag acggcatttg gaattggaag     1260
aacagagaat acgactcatt ctctgcttac cgaaaaggaa cggcaaacga ttcggattcc     1320
atttatgcgg acccgatgta ccgtgacgaa tcgtcttatg actttacatt aaagcccgga     1380
tcaccggccc tgcccgtcat tcagtaa                                         1407
```

<210> SEQ ID NO 22
<211> LENGTH: 468
<212> TYPE: PRT
<213> ORGANISM: Bacillus Amyloliquefaciens

<400> SEQUENCE: 22

Met Lys Ile Lys Leu Ser Ile Leu Ser Ala Ala Val Leu Ala Ala Gly
1               5                   10                  15

Ile Thr Ala Phe Val Trp Pro Lys Thr Glu Ala Asn Glu Lys Thr Gln
                20                  25                  30

Thr Asp Ala Val Tyr Val Ser Pro Ala Gly Ser Asp Gln Asn Glu Gly
            35                  40                  45

Thr Leu Glu Lys Pro Phe Arg Thr Leu Lys His Ala Ala Glu Lys Ala
        50                  55                  60

Glu Ala Gly Thr Thr Val Leu Ile Arg Glu Gly Thr Tyr Asp Glu Thr
65                  70                  75                  80

Phe Glu Val Lys His Ser Gly Thr Ala Glu Lys Pro Ile Thr Phe Arg
                85                  90                  95

Asn Tyr Gln Asn Glu His Val Ser Ile Ser Gly Lys Ser Ala Pro Lys
                100                 105                 110

Ser Asp Ser Glu Thr Pro Leu Ile Gln Ile Arg Asn Lys Gln Tyr Ile
        115                 120                 125

```
Thr Ile His Gly Val Thr Leu Glu Asn Leu Ser Val Ser Ser Glu Asp
        130                 135                 140
Ala Thr Ala Met Gly Ile Cys Val Thr Gly Ser Ser Ser His Ile Asn
145                 150                 155                 160
Ile Glu Gly Asn His Ile Arg Asn Ile Lys Thr Thr Ala Asp Glu Gly
                165                 170                 175
Asn Ala His Gly Ile Ala Phe Tyr Gly Thr Gly Ala Met Lys Asp Val
                180                 185                 190
Ser Ile Thr Asn Asn Thr Val Glu Lys Leu Thr Leu Gly Ala Ser Glu
                195                 200                 205
Ala Val Val Leu Asn Gly Asn Val Asp Gly Phe Lys Ile Ala Gly Asn
        210                 215                 220
Thr Ile Arg Asp Asn Asn Asn Ile Gly Ile Asp Val Ile Gly Tyr Glu
225                 230                 235                 240
Gly Thr Ser Lys Gln Asn Asp Tyr Ala Arg Asn Gly Val Ile Glu Asn
                245                 250                 255
Asn Thr Val Ser His Asn Ser Ser Tyr Gly Asn Pro Ala Tyr Gly Asp
                260                 265                 270
Glu Tyr Ser Ala Gly Gly Ile Tyr Val Asp Gly Ala Glu His Val Asp
                275                 280                 285
Ile Lys Lys Asn Thr Val Tyr Asn Asn Asp Leu Gly Ile Glu Ala Thr
        290                 295                 300
Ser Glu His Arg Gly Lys Tyr Ala Arg Asp Ile Arg Ile Thr Asp Asn
305                 310                 315                 320
Lys Val Tyr Gly Asn Ala Tyr Thr Gly Ile Ser Ile Gly Gly Tyr Asp
                325                 330                 335
Thr Lys Arg Gly Gly Thr Ile Asn Ser Val Ile Ala His Asn Ile Met
                340                 345                 350
Tyr Arg Asn Asp Thr Lys Asp Leu Asp Gly Gly Gln Leu Leu Leu Gln
                355                 360                 365
Tyr Gly Thr Lys Gly Asn Thr Ile Glu Lys Asn Ile Met Thr Ala Ser
                370                 375                 380
Gly Ser Arg Ile Phe Ile Ala Asn Asp Tyr Thr Lys Asn Glu Gly Asn
385                 390                 395                 400
Thr Val Asn His Asn Val Tyr His Lys Glu Ala Gly Lys Asp Gly Ile
                405                 410                 415
Trp Asn Trp Lys Asn Arg Glu Tyr Asp Ser Phe Ser Ala Tyr Arg Lys
                420                 425                 430
Gly Thr Ala Asn Asp Ser Asp Ser Ile Tyr Ala Asp Pro Met Tyr Arg
                435                 440                 445
Asp Glu Ser Ser Tyr Asp Phe Thr Leu Lys Pro Gly Ser Pro Ala Leu
        450                 455                 460
Pro Val Ile Gln
465

<210> SEQ ID NO 23
<211> LENGTH: 1065
<212> TYPE: DNA
<213> ORGANISM: Bacillus Amyloliquefaciens

<400> SEQUENCE: 23
atgataaaga agacgcgtca tctcgctttc ttggctgcac tcggctttgc gctttgtctg      60
gccatcgtat gttccgcatc aaagcaggca gaagcggcag cggcttatcc ggatgtgatg     120
cagggactta ccggattcgc gggaaatgcg aaggatcata acggaaaagc aaaatccgcc     180
```

-continued

```
gtaacgggag gccagggcgg ccccgtcgtc tacgtcagca atctcaatga tttgaaaaac    240
aatgcgggcg gaacggaccg caaaaccatc gtcatcacaa gtgatatttc ttccccgggt    300
aaagccgtcg tgacagtcgg cgccaataaa accatcgtcg gctcttatac cagccacagg    360
ctgaccaaca tctatctgac caccggctcc ggctcaaaca atgtgatttt caaaaatctc    420
attatcagcc atagtgccgc cattacgggc aacaacgaca ttccgatgta catagcgaac    480
ggacagaatt actggattga ccacgtgtgg tttgaaggac acagctacaa tccgaacagc    540
cacagtgatt tgggaaagct tctgtatgtc ggcgccaaag cggattttgt gacgctgtct    600
aactctaaat tcacagacca tctgtacggg ctgattctcg gttatccgaa tgatgataac    660
gaaggacgca attatatcgg ctatccgcat atgacgatca ccaacaacta ttttaataac    720
gtctatgtgc gttcaccggg cctgatgaga tacggctatt tcacgcgaa aaacaactat    780 gtgaccaatt tcaatttagg attcaccatt catacaaacg cgactgtctt ctcagaagcc    840
aactatttcg gtaacggaaa tgaaaaaggc ggaatgatag acgactacgg gacggcccaa    900
ttcaccgaca ccggttcatt cccgtcgctc aaggccccga atcaccgcg caccggctgg    960 aatccgagat caaattacag ctacggcacc ctttcagccc aggacgccaa aaacttcgcc    1020
caatcttacg cgggagcgca aaatacaaat ctccgctatc cataa                   1065
```

<210> SEQ ID NO 24
<211> LENGTH: 354
<212> TYPE: PRT
<213> ORGANISM: Bacillus Amyloliquefaciens

<400> SEQUENCE: 24

```
Met Ile Lys Lys Thr Arg His Leu Ala Phe Leu Ala Ala Leu Gly Phe
1               5                   10                  15

Ala Leu Cys Leu Ala Ile Val Cys Ser Ala Ser Lys Gln Ala Glu Ala
            20                  25                  30

Ala Ala Ala Tyr Pro Asp Val Met Gln Gly Leu Thr Gly Phe Ala Gly
        35                  40                  45

Asn Ala Lys Asp His Asn Gly Lys Ala Lys Ser Ala Val Thr Gly Gly
    50                  55                  60

Gln Gly Gly Pro Val Val Tyr Val Ser Asn Leu Asn Asp Leu Lys Asn
65                  70                  75                  80

Asn Ala Gly Gly Thr Asp Arg Lys Thr Ile Val Ile Thr Ser Asp Ile
                85                  90                  95

Ser Ser Pro Gly Lys Ala Val Val Thr Val Gly Ala Asn Lys Thr Ile
            100                 105                 110

Val Gly Ser Tyr Thr Ser His Arg Leu Thr Asn Ile Tyr Leu Thr Thr
        115                 120                 125

Gly Ser Gly Ser Asn Asn Val Ile Phe Lys Asn Leu Ile Ile Ser His
    130                 135                 140

Ser Ala Ala Ile Thr Gly Asn Asn Asp Ile Pro Met Tyr Ile Ala Asn
145                 150                 155                 160

Gly Gln Asn Tyr Trp Ile Asp His Val Trp Phe Glu Gly His Ser Tyr
                165                 170                 175

Asn Pro Asn Ser His Ser Asp Leu Gly Lys Leu Leu Tyr Val Gly Ala
            180                 185                 190

Lys Ala Asp Phe Val Thr Leu Ser Asn Ser Lys Phe Thr Asp His Leu
        195                 200                 205

Tyr Gly Leu Ile Leu Gly Tyr Pro Asn Asp Asp Asn Glu Gly Arg Asn
```

```
              210                 215                 220
Tyr Ile Gly Tyr Pro His Met Thr Ile Thr Asn Asn Tyr Phe Asn Asn
225                 230                 235                 240

Val Tyr Val Arg Ser Pro Gly Leu Met Arg Tyr Gly Tyr Phe His Ala
                245                 250                 255

Lys Asn Asn Tyr Val Thr Asn Phe Asn Leu Gly Phe Thr Ile His Thr
                260                 265                 270

Asn Ala Thr Val Phe Ser Glu Ala Asn Tyr Gly Asn Gly Asn Glu
            275                 280                 285

Lys Gly Gly Met Ile Asp Asp Tyr Gly Thr Ala Gln Phe Thr Asp Thr
            290                 295                 300

Gly Ser Phe Pro Ser Leu Lys Ala Pro Lys Ser Pro Arg Thr Gly Trp
305                 310                 315                 320

Asn Pro Arg Ser Asn Tyr Ser Tyr Gly Thr Leu Ser Ala Gln Asp Ala
                325                 330                 335

Lys Asn Phe Ala Gln Ser Tyr Ala Gly Ala Gln Asn Thr Asn Leu Arg
                340                 345                 350

Tyr Pro
```

<210> SEQ ID NO 25
<211> LENGTH: 1577
<212> TYPE: DNA
<213> ORGANISM: Bacillus Amyloliquefaciens

<400> SEQUENCE: 25

```
gatcctggct caggacgaac gctggcggcg tgcctaatac atgcaagtcg agcggacaga      60
tgggagcttg ctccctgatg ttagcggcgg acgggtgagt aacacgtggg taacctgcct     120
gtaagactgg gataactccg ggaaaccggg gctaataccg gatggttgtc tgaaccgcat     180
ggttcagaca taaaaggtgg cttcggctac cacttacaga tggacccgcg gcgcattagc     240
tagttggtga ggtaacggct caccaaggcg acgatgcgta gccgacctga gagggtgatc     300
ggccacactg ggactgagac acggcccaga ctcctacggg aggcagcagt agggaatctt     360
ccgcaatgga cgaaagtctg acggagcaac gccgcgtgag tgatgaaggt tttcggatcg     420
taaagctctg ttgttaggga agaacaagtg ccgttcaaat agggcggcac cttgacggta     480
cctaaccaga aagccacggc taactacgtg ccagagccgc gggtaatacg taggtggcaa     540
gcgttgtccg gaattattgg gcgtaaaggg ctcgcaagcg tttctcttaag tctgatgtga     600
aaccccggg ctcaaccggg gagggtcatt ggaaaccgag gaacttgagt gcagaagagg     660
agagtggaat tccacgtgta gcggtgaaat gcgtagagat gtggaggaac accagtggcg     720
aaggcgactc tctgttctgt aactgacgct gagagagcga agcgtgggga gcaacagaa      780
ttagataccc tggtagtcca cgccgtaaac gatgagtgct aagtgttagg gggtttccgc     840
cccttagtgc tgcagctaac gcattaagca ctccgcctgg ggagtacggt cgcaagactg     900
aaactcaaag gaattgacgg gggcccgcac aagcggtgga gcatgtggtt taattcgaag     960
caacgcgaag aaccttacca ggtcttgaca tcctctgaca atcctagaga taggacgtcc    1020
ccttcgggg cagagtgaca ggtggtgcat ggttgtcgtc agctcgtgtc gtgagatgtt    1080
gggttaagtc ccgcaacgag cgcaacccctt gatcttagtt gccagcattc agttgggcac    1140
tctaaggtga ctgccggtga caaaccggag gaaggtgggg atgacgtcaa atcatcatgc    1200
cccttatgac ctgggctaca cacgtgctac aatggacaga acaaagggca gcgaaaccgc    1260
gaggttaagc caatcccaca aatctgttct cagttcggat cgcagtctgc aactcgactg    1320
```

```
cgtgaagctg gaatcgctag taatcgcgga tcagcatgcc gcggtgaata cgttcccggg    1380
ccttgtacac accgcccgtc acaccacgag agtttgtaac acccgaagtc ggtgaggtaa    1440
cctttatgga gccagccgcc gaaggtggga cagatgattg gggtgaagtc gtaacaaggt    1500
agccgtatcg gaaggtgcgg ctggatcacc tcctttctaa ggattttaac ggaatataag    1560
accttgggtc ttataac                                                   1577

<210> SEQ ID NO 26
<211> LENGTH: 1836
<212> TYPE: DNA
<213> ORGANISM: Bacillus Amyloliquefaciens

<400> SEQUENCE: 26
atgtacatcg atcaactaa cagcaaaggc cttcaccact ggtgtgggaa aatcgtcgac      60
aacagtattg acgaagccct ggccggttat tgtacagata ttaacatcga gattgaaaaa    120
gataacagca ttaccgttaa ggacaacggg cgcggaattc cggtcggtat ccaggagaag    180
atgggccgcc ctgcggttga agtcatcatg accgttctcc acgccggcgg taaatttgac    240
ggaagcggat ataaagtatc cggcggtctt cacggtgtag gggcatctgt cgtaaacgcc    300
ttgtcgacca ctcttgacgt tacgcttcat cgtgacggaa aaatccacta tcaggcgtac    360
gagcgcggtg tacctgtggc cgatcttgaa gtgatcggtg atactgataa gaccggaacg    420
attacgcact tcgttccgga tccggaaatc ttcaaagaaa caatcgtata cgactatgat    480
ctgctttcaa accgtgtccg ggaattggcc ttcctgacaa aaggcgtaaa catcacgatt    540
gaagacaaac gtgatggaca agaacggaaa aacgagtacc actacgaagg cggaatcaaa    600
agctatgttg agtacttaaa ccgttccaaa gaagtcgttc atgaagagcc gatttatatc    660
gaaggcgaga aagacggcat aacggttgaa gttgcattgc aatacaacga cagctataca    720
agcaacattt attctttcac aaataatatc aacacttacg aaggcgggac gcacgaagcc    780
ggatttaaaa ccgtctgac ccgtgtcata acgactatg caagaagaaa agggattttc    840
aaagaaaatg atccgaactt aagcggggat gatgtgagag aagggctgac tgccattatt    900
tcaattaagc accctgatcc gcaattcgaa gggcagacga aaaccaagct cggcaactcc    960
gaagcgagaa cgatcactga tacgctgttt tcttctgcgc tggaaacatt ccttcttgaa   1020
aatccggact cagcccgcaa aattgttgaa aaaggtttaa tggccgcaag agcgcggatg   1080
gcagcgaaaa aagcacggga attgacccgg cgcaaaagtg cgcttgagat ttccaatctg   1140
ccgggcaaac tggcggactg ttcttctaaa gatccgagca tttccgagct gtatatcgta   1200
gagggtgact ctgcgggcgg atcagcgaaa caggacgggg accgtcattt ccaagctatt   1260
ctgccgctgc gcggtaagat tctgaacgtt gagaaagcca gacttgataa gattctctca   1320
aacaatgagg tcagatcaat gatcacggcc tccggaacag gaatcggaga agattttaat   1380
cttgaaaaag cccgttatca taaagtggtc atcatgacgg atgccgatgt tgacggcgcc   1440
cacatcagaa cgctttttatt aacgttcttc tacagataca tgcgggaaat catcgaaaac   1500
ggctatgtct acattgccca gccgccgctt tataaagtgc agcagggaaa acgggtggaa   1560
tacgcttata cgataagca gcttgatgag ctgttaaaag aacttccgca atcacctaag   1620
cccggcctcc agcgttataa aggtcttgga gaaatgaacg cgactcagct ttgggaaacg   1680
```

```
acaatggacc ctgcgaccag aacgcttctg caagtcaatc ttgaagatgc aatggacgct    1740
gacgagactt ttgaaatgct gatgggtgac aaagtagaac cgcggagaaa cttcatagaa    1800
gcaaacgcca gatacgtgaa aaaccttgat atttaa                              1836
```